US006492123B1

(12) United States Patent
Holliger et al.

(10) Patent No.: US 6,492,123 B1
(45) Date of Patent: *Dec. 10, 2002

(54) MULTIVALENT AND MULTISPECIFIC BINDING PROTEINS AND THEIR USE

(75) Inventors: Kaspar-Philip Holliger, Cambridge (GB); Andrew David Griffiths, Cambridge (GB); Hendricus Renerus Jacobus Matheus Hoogenboom, Hasselt (BE); Magnus Malmqvist, Uppsala (SE); James David Marks, Kensington, CA (US); Brian Timothy McGuinness, Cambridge (GB); Anthony Richard Pope, Cambridge (GB); Terence Derek Prospero, Cambridge (GB); Gregory Paul Winter, Cambridge (GB)

(73) Assignee: Medical Research Council, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/146,979

(22) Filed: Sep. 3, 1998

Related U.S. Application Data

(63) Continuation of application No. 08/448,418, filed as application No. PCT/GB93/02492 on Dec. 3, 1993, now Pat. No. 5,837,242.

(30) Foreign Application Priority Data

Dec. 4, 1992 (GB) .............................................. 9225453

(51) Int. Cl.[7] .............................................. G01N 33/53
(52) U.S. Cl. .................. 435/7.1; 530/387.1; 530/387.3; 424/135.1
(58) Field of Search ................................. 435/7.1, 69.1, 435/69.7, 69.8, 320.1, 328; 514/2; 530/387.1, 412, 413, 387.3; 536/23.4, 23.53, 24.1; 424/133.1, 136.1, 135.1

(56) References Cited

U.S. PATENT DOCUMENTS

| | | | |
|---|---|---|---|
| 4,844,613 A | | 7/1989 | Batchelder et al. |
| 4,946,778 A | | 8/1990 | Ladner et al. |
| 5,196,320 A | | 3/1993 | Gillies |
| 5,292,668 A | | 3/1994 | Paulus |
| 5,434,066 A | | 7/1995 | Bebee et al. |
| 5,534,254 A | | 7/1996 | Huston et al. |
| 5,763,733 A | | 6/1998 | Whitlow et al. |
| 5,767,260 A | | 6/1998 | Whitlow et al. |
| 5,837,242 A | * | 11/1998 | Holliger et al. |
| 5,844,094 A | | 12/1998 | Hudson et al. |
| 5,856,456 A | | 1/1999 | Whitlow et al. |
| 5,869,620 A | | 2/1999 | Whitlow et al. |
| 5,885,793 A | | 3/1999 | Griffiths et al. |
| 5,990,275 A | | 11/1999 | Whitlow et al. |
| 6,025,165 A | | 2/2000 | Whitlow et al. |
| 6,027,725 A | | 2/2000 | Whitlow et al. |
| 6,103,889 A | | 8/2000 | Whitlow et al. |
| 6,121,424 A | | 9/2000 | Whitlow et al. |

FOREIGN PATENT DOCUMENTS

| | | |
|---|---|---|
| WO | WO 88/09344 | 1/1988 |
| WO | WO 88/06630 | 9/1988 |
| WO | WO 90/14443 | 11/1990 |
| WO | WO 92/01047 | 1/1992 |
| WO | WO 93/11161 | 6/1993 |
| WO | WO 94/04691 | 3/1994 |

OTHER PUBLICATIONS

Bird et al., "Single chain antibody variable regions," *Trends in Biotechnology*, 9: 132–137 (1991).
Condra et al., "Bacterial Expression of Antibody Fragments That Block Human Rhinovirus Infection of Cultured Cells", *J. Biological Chemistry*, 265 (4):2292–2295 (Feb. 5, 1990).
Garrard et al., "Fab assembly and enrichment in a monovalent phage display system," *Bio/Technology*, 9:1373–1377 (Dec. 1991).
Griffiths et al., "Human anti–self with high specificity from phage display libraries," *EMBO J.*, 12(2):725–734 (1993).
Hoogenboom et al., "Multi–subunit proteins on the surface of filamentous phage: methodologies for displaying antibody (Fab) heavy and light chains," *Nucleic Acids Research*, 19(15):4133–4137 (1991).
Huston et al., "Protein Engineering of Single Chain Fv Analogs and Fusion Proteins," *Methods in Enzymology*, 203:46–88 (1991).
Pantoliano et al., "Conformational stability, folding and ligand–binding affinity of single–chain Fv immunoglobulin fragments expressed in *Echerichia coli*," *Biochemistry*, 30:10117–10125 (1991).
Wels et al., "Construction, bacterial expression and characterization of a bifunctional single–chain antibody–phosphatase fusion protein targeted to the human erB–2 receptor," *Bio/Technology*, 10:1128–1132 (Oct. 1992).
Whitlow et al., "An improved linker for single–chain Fv with reduced aggregation and enhanced proteolytic stabilty," *Protein Engineering*, 6(8):989–995 (1993).

* cited by examiner

Primary Examiner—Sheela Huff
Assistant Examiner—Larry R. Helms
(74) *Attorney, Agent, or Firm*—Nixon & Vanderhye P.C.

(57) ABSTRACT

Polypeptides comprising a first domain, which comprises a binding region of an immunoglobulin heavy chain variable region, and a second domain, which comprises a binding region of an immunoglobulin light chain variable region, the domains being linked but incapable of associating with each other to form an antigen binding site, associate to form antigen binding multimers, such as dimers, which may be multivalent or have multispecificity. The domains may be linked by a short peptide linker or may be joined directly together. Bispecific dimers may have longer linkers. Methods of preparation of the polypeptides and multimers and diverse repertoires thereof, and their display on the surface of bacteriophage for easy selection of binders of interest, are disclosed, along with many utilities.

33 Claims, 28 Drawing Sheets

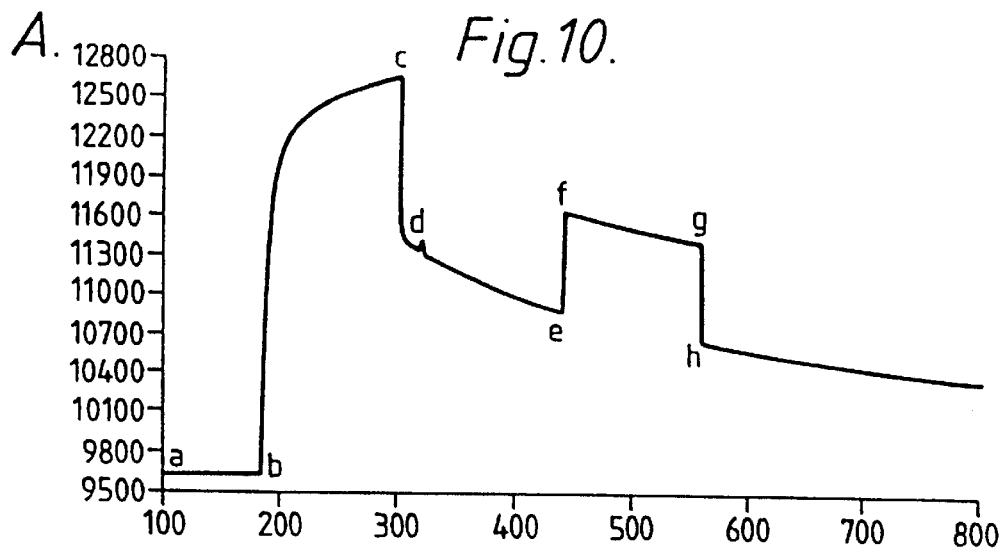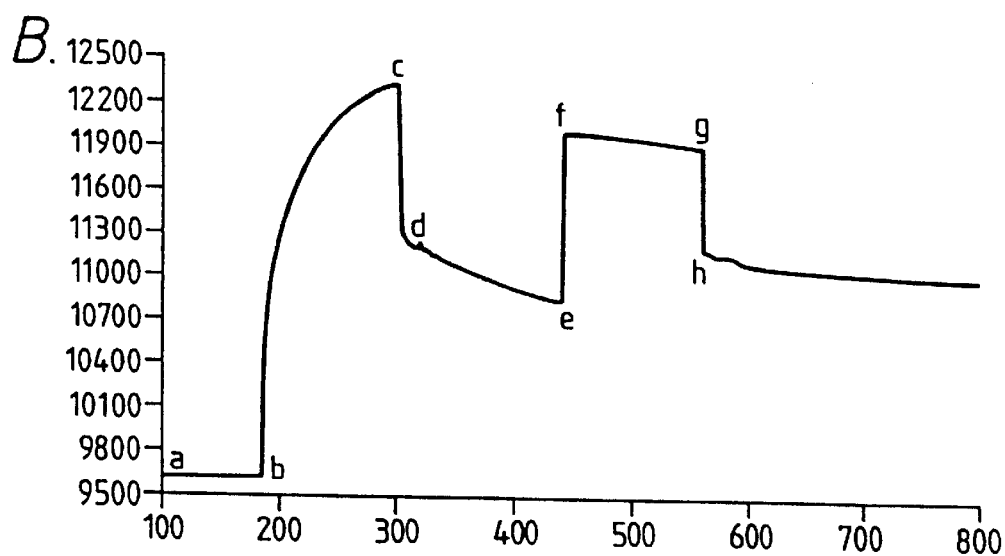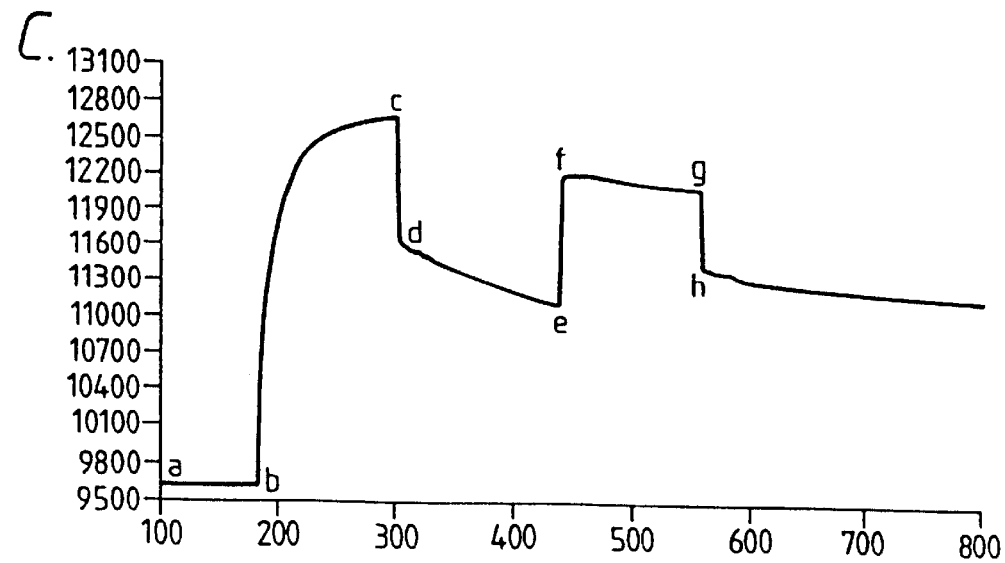
Fig. 10.

Fig.16.
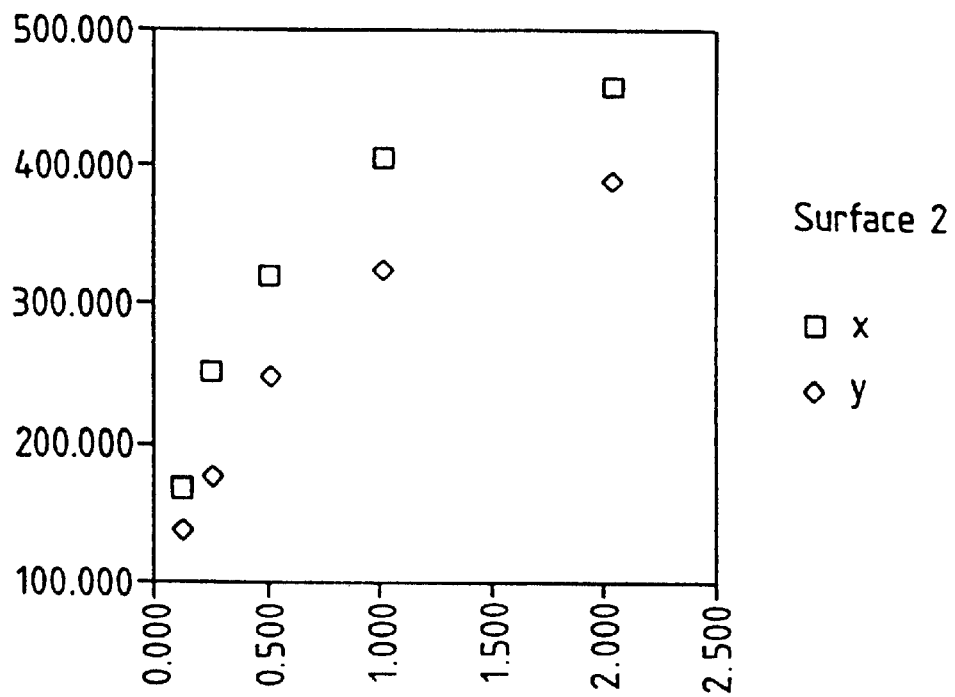
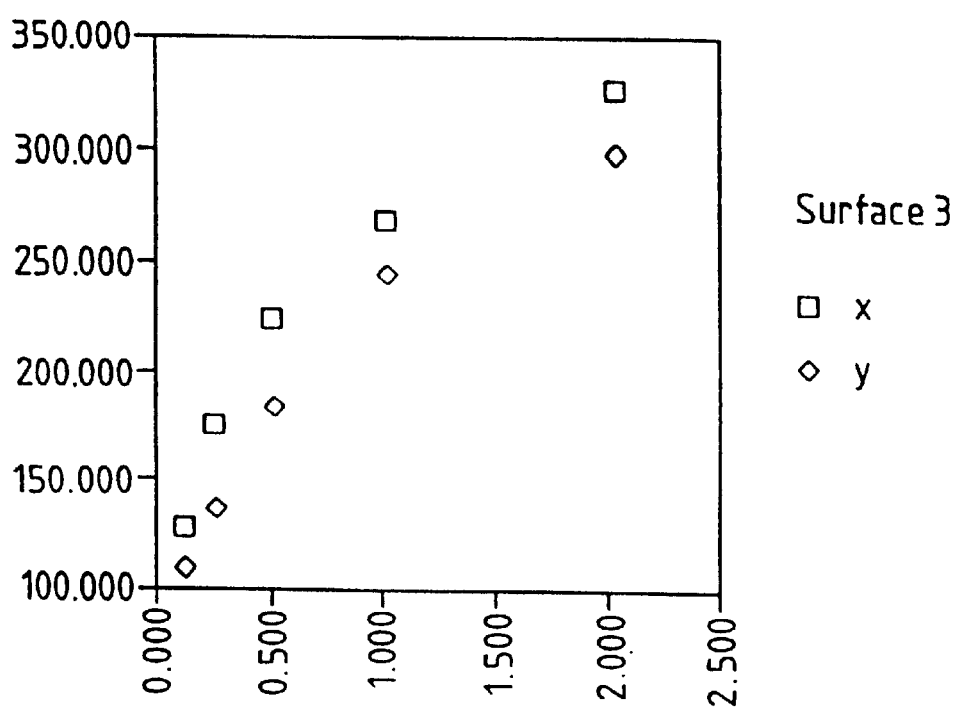

Fig. 17.
A.
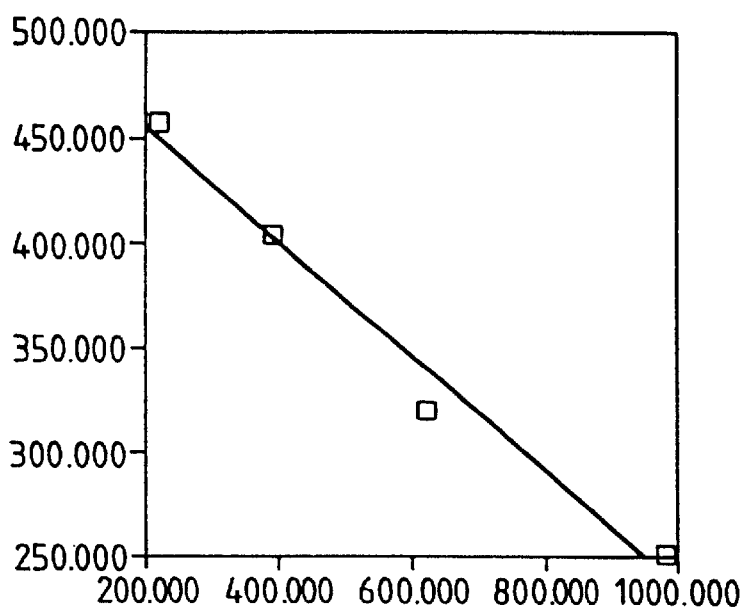
B.
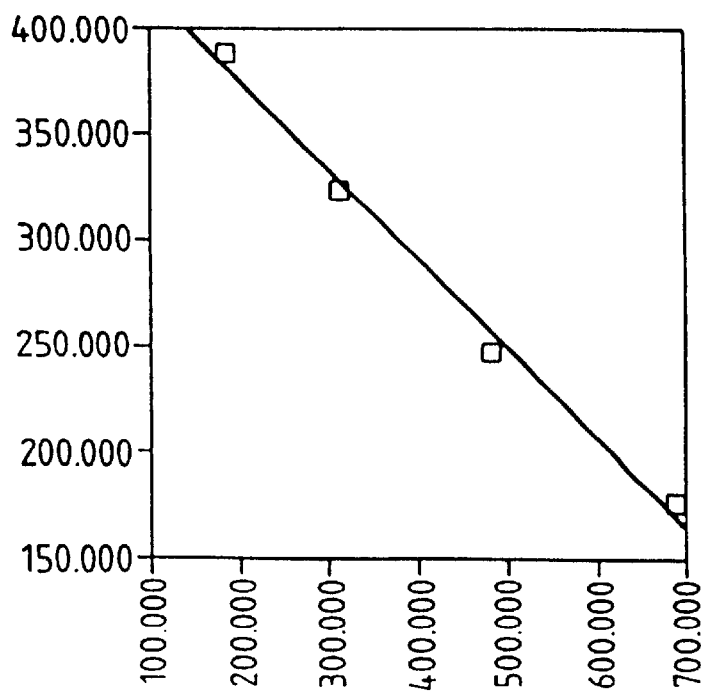

Fig.18.
A.
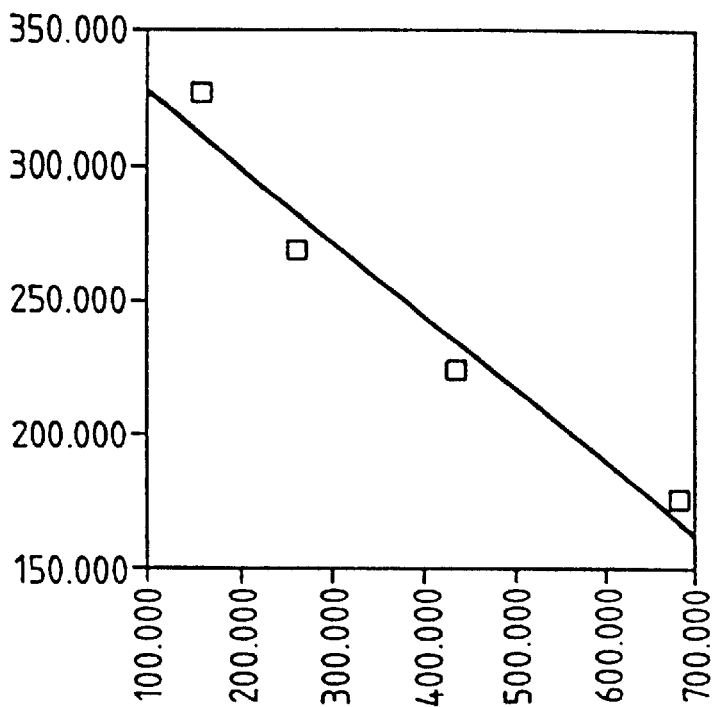
B.
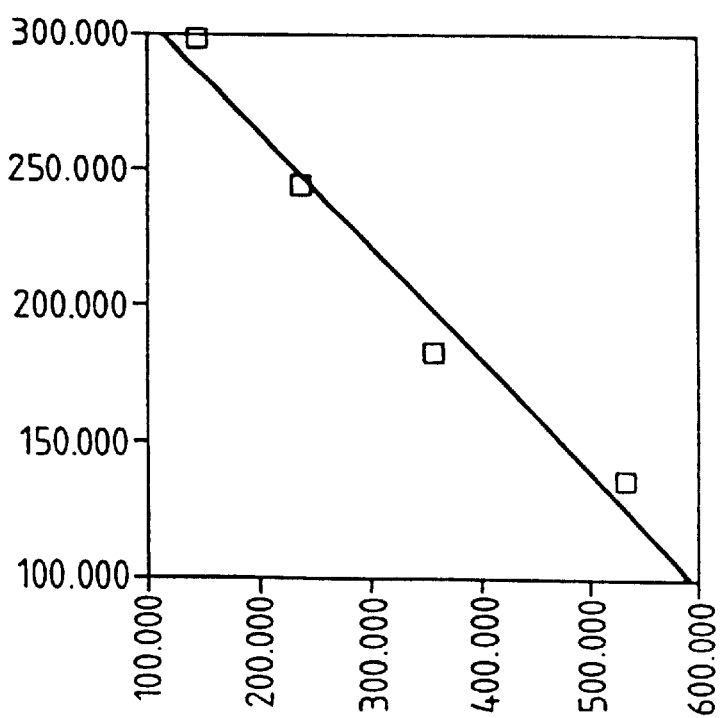

Fig. 20.

HindIII
AAGCTT TGGAGCCTTT TTTTGGAGA TTTTCAAC GTG AAA AAA TTA TTA TTC GCA
                                         V   K   K   L   L   F   A
         signal sequence SfiI
ATT CCT TTA GTT GTT CCT TTC TAT GCG GCC CAG CCG GCC ATG GCC CAG
 I   P   L   V   V   P   F   Y   A   A   Q   P   A   M   A   Q NotI
GTC CAA CTG CAG GTC GAC CTC GAG ATC AAA CGG GCG GCC GCA CAT CAT
 V   Q   L   Q   V   D   L   E   I   K   R   A   A   A   H   H
    HIS tag                                         Myc tag CAT CAC CAT CAC GGG GCC GCA GAA CAA AAA CTC ATC TCA GAA GAG GAT CTG
 H   H   H   H   G   A   A   E   Q   K   L   I   S   E   E   D   L
              Amber
              Gene 3

AAT GGG GCC GCA TAG ACT GTT GAA AGT TGT TTA GCA AAA CCT CAT ACA
 N   G   A   A   *   T   V   E   S   C   L   A   K   P   H   T

GAA AAT TCA TTT ACT AAC GTC TGG
 E   N   S   F   T   N   V

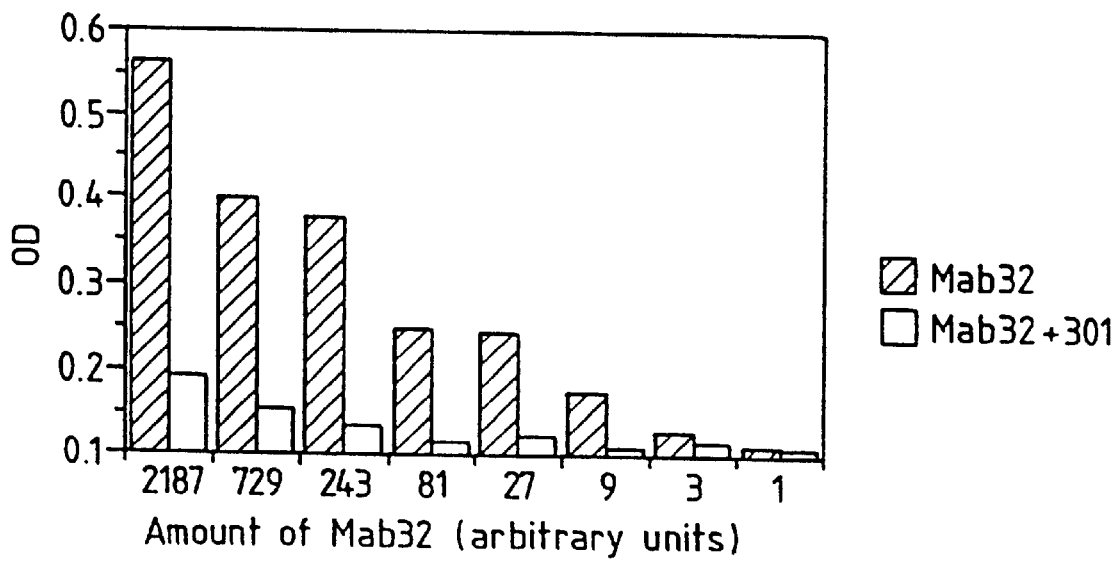
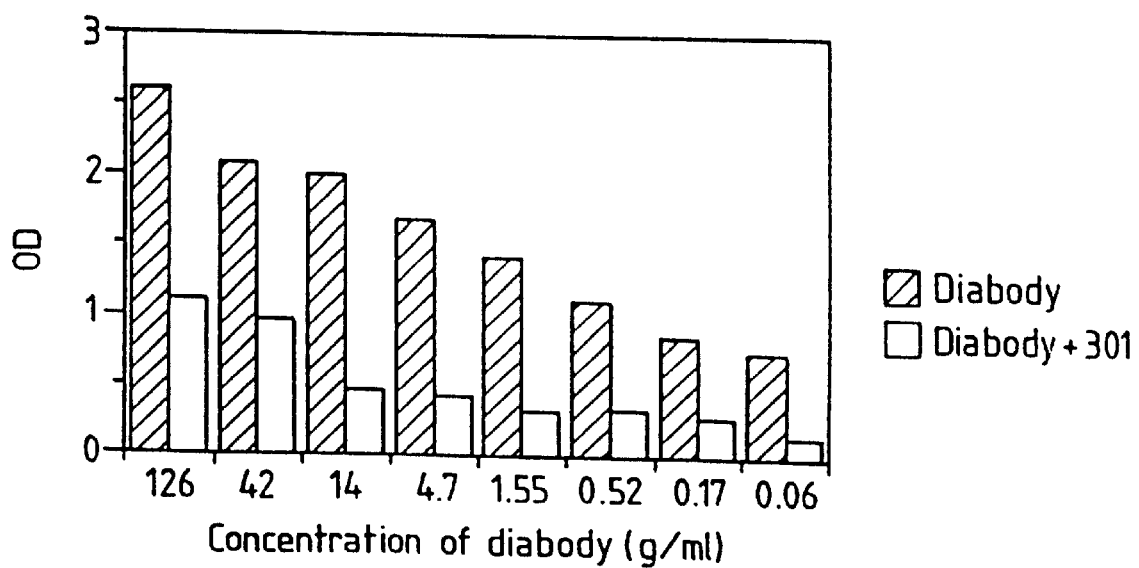
Fig. 29.

| Fig.32a |
| Fig.32b |
| Fig.32c |

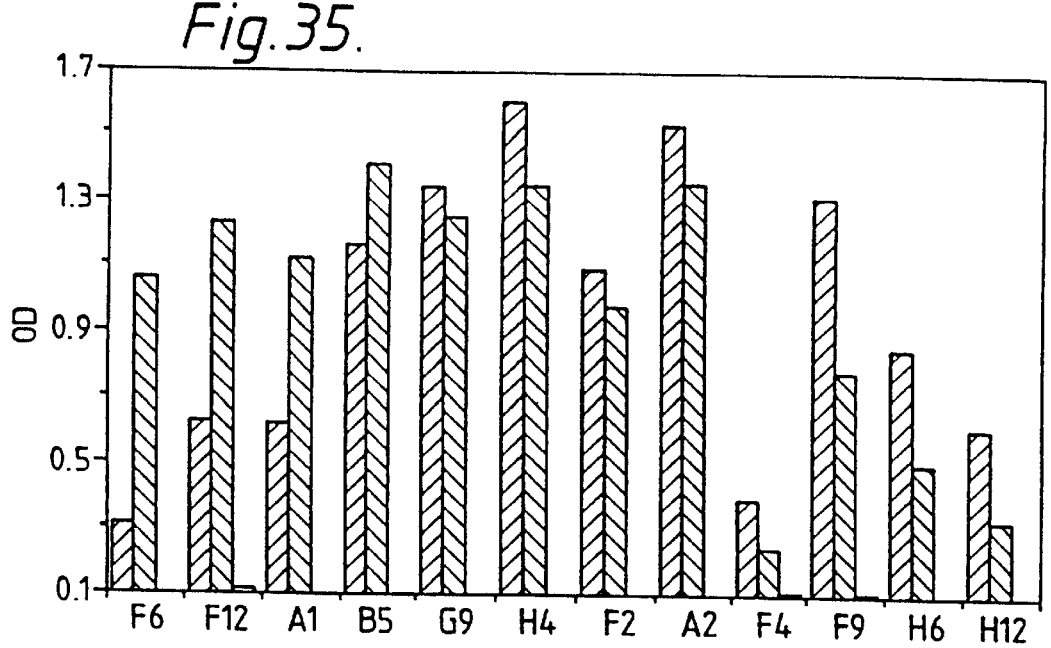
Fig. 35.
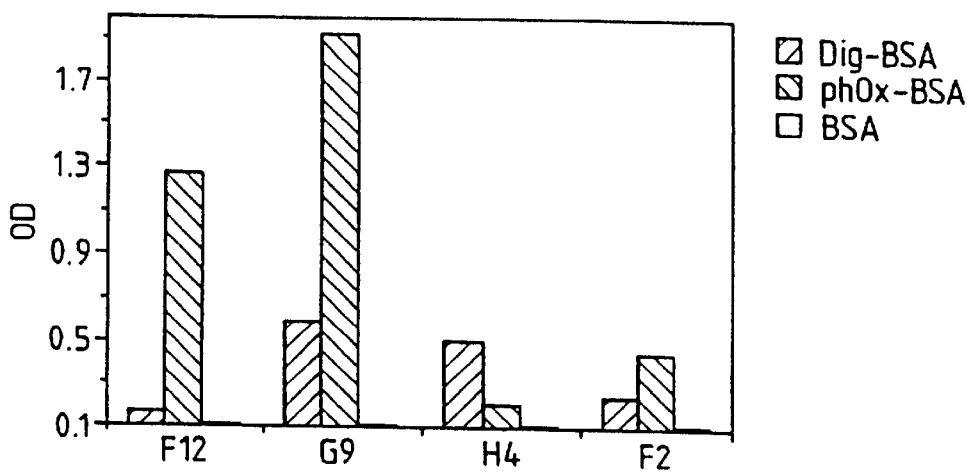
- Dig-BSA
- phOx-BSA
- BSA
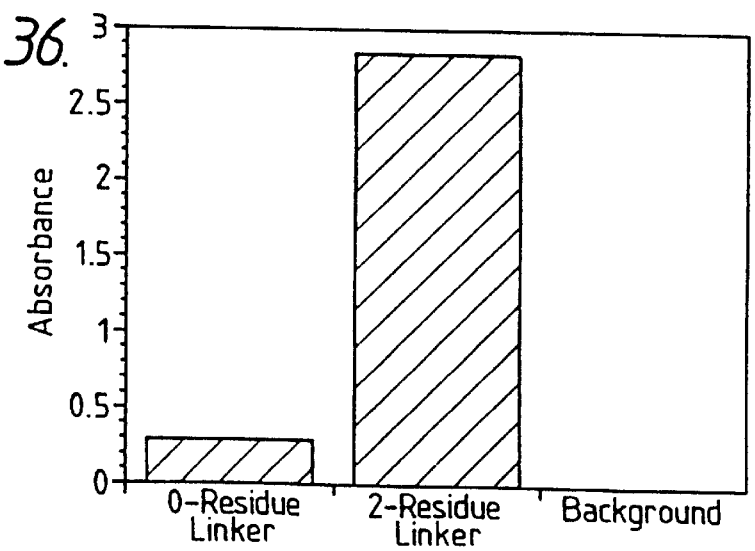
Fig. 36.

MULTIVALENT AND MULTISPECIFIC BINDING PROTEINS AND THEIR USE

CROSS REFERENCE TO RELATED APPLICATION

This application is a continuation of U.S. patent application Ser. No. 08/448,418, filed May 14, 1996, now U.S. Pat. No. 5,837,421 and from which priority is claimed, which in turn is the U.S. national phase of international application PCT/GB93/02492 filed Dec. 3, 1993, from which priority is claimed.

FIELD OF THE INVENTION

The present invention relates to binding proteins, methods of making the proteins, and uses thereof. More particularly, the present invention relates to synthetic binding proteins which comprise immunoglobulin heavy and light chain variable domain binding regions. Polypeptides are provided which form multimers, eg dimers, which may have more than one binding specificity.

Because of the length of the specification, it is appropriate to include here a list of contents to help the reader find passages of interest. In addition to claims, figures and an abstract, the specification includes the following, in order:

Statement of the field of the invention;

Contents;

Brief discussion of prior art and introduction to the invention;

(Background)

Discussion of the invention;

Summary of the Invention

Brief description of the figures;

Discussion of bivalent and bispecific antibodies, preparation and uses;

Preparation of "diabodies", discussion of structure and various utilities;

Figure 1:
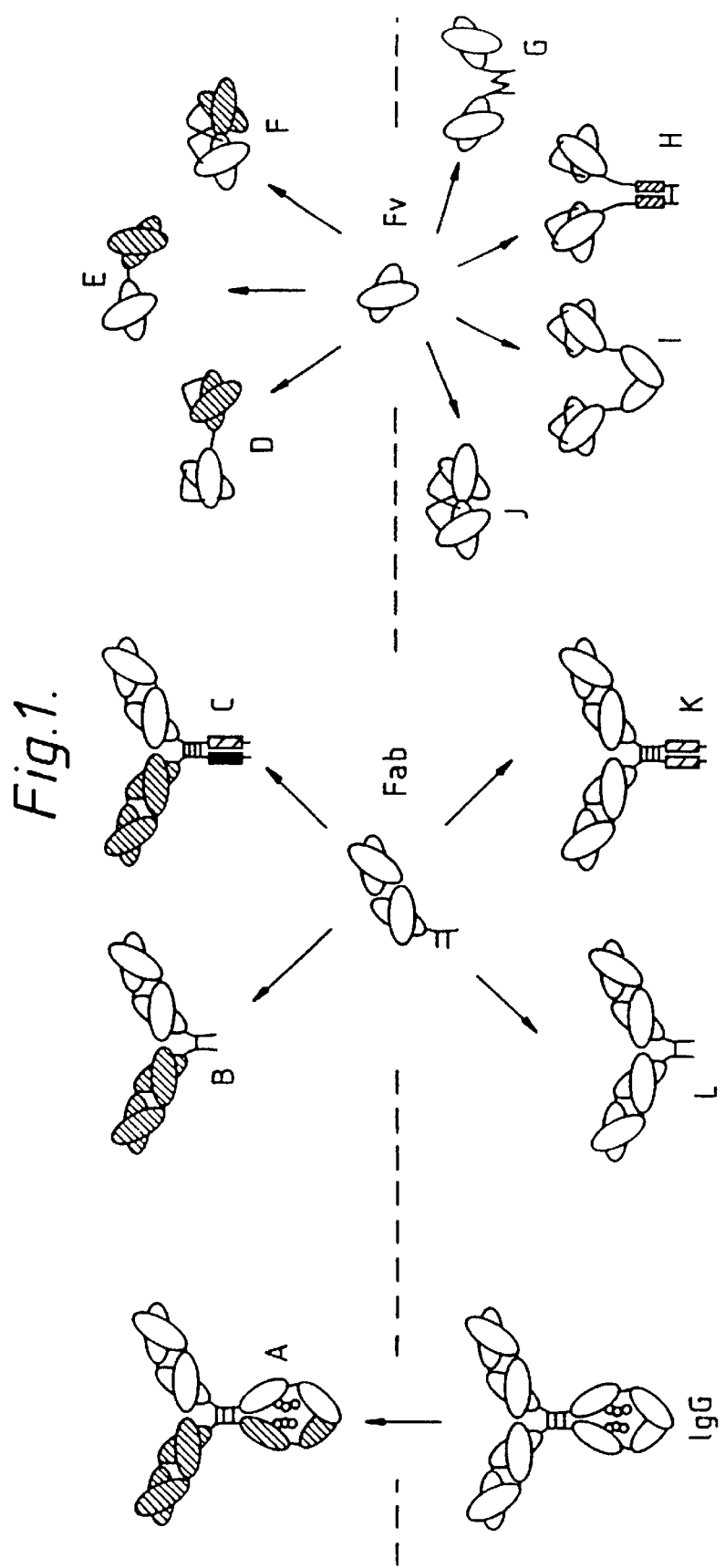

Discussion of construction of repertoires of diabodies and their display on bacteriophage;

Listing of the experimental examples;

Experimental examples and discussion;

All documents mentioned in this text are incorporated herein by reference.

BACKGROUND

Natural antibodies are multivalent, for example Ig G antibodies have two binding sites and IgM antibodies have five binding sites for antigen. The multivalency means that the antibodies can take advantage of multiple interactions in binding to solid phase antigen, and therefore increasing the avidity of binding to the antigen. It is possible to make recombinant bivalent IgG and pentameric decavalent IgM antibodies by expression in mammalian cells. To date, of the various possibilities for multivalency bivalent antibodies have been of greatest interest.

Of further interest are antibodies which are able to bind to two or more different epitopes, those which have multispecificity. Bispecific antibodies have many proven and expected utilities, discussed infra.

Structurally, the simplest antibody (IgG) comprises four polypeptide chains, two heavy (H) chains and two light (L) chains inter-connected by disulphide bonds. The light chains exist in two distinct forms called kappa (K) and lambda (λ). Each chain has a constant region (C) and a variable region (V). Each chain is organised into a series of domains. The light chains have two domains, corresponding to the C region and to the V region. The heavy chains have four domains, one corresponding to the V region and three domains (1, 2 and 3) in the C region.

The antibody has two arms (each arm being a Fab region), each of which has a VL and a VH region associated with each other. It is this pair of V regions that differs from one antibody to another (owing to amino acid sequence variations), and which together are responsible for recognising the antigen and providing an antigen binding site. In even more detail, each V region is made up from three complementarity determining regions (CDR) separated by four framework regions (FR). The CDRs are the most variable part of the variable regions, and they perform the critical antigen binding function.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment which consists of a VH domain; (v) isolated CDR regions; and (vi) F(ab')$_2$ fragments, a bivalent fragment comprising two Fab fragments linked by a disulphide bridge at the hinge region.

The fragments largely represent portions of complete antibodies. However, the term "fragment" is also applied to synthetic molecules which comprise antibody heavy and light chain variable domains, or binding portions of these domains, associated so as to have specific antigen binding capability. A good example of an antibody fragment which is of this type is the "single chain Fv" (scFv) fragment which consists of an antibody heavy chain variable domain linked to an antibody light chain variable domain by a peptide linker which allows the two domains to associate to form a functional antigen binding site (see, for example U.S. Pat. No. 4,946,778, Ladner et al., (Genex); WO 88/09344, Creative Biomolecules, Inc/Huston et al.). WO 92/01047, Cambridge Antibody Technology et al./McCafferty et al., describes the display of scFv fragments on the surface of soluble recombinant genetic display packages, such as bacteriophage.

Some experimental work has been described wherein the length of the peptide linker of scFv molecules was varied. The range of linker lengths has in general been from 12 to 18 amino acids, with 15 amino acids being the most usual, see e.g. M C Whitlow et al., *Protein Engineering* 6: 989–995, 1993. In all cases the linker was long enough for the two domains, one VL, the other VH, to associate to form an antigen binding site, this being a characterising feature of scFv's. Condra et al., for example (*The Journal of Biological Chemistry*, 256:2292–2295, 1990) varied the length of the linker of scFv fragments able to block human rhinovirus attachment to cellular receptors. What the authors describe in this paper as a VL domain includes amino acids from the C domain (as can be seen from reviewing Kabat et al., *Sequences of proteins of Immunological Interest*, US Government Printing Office), and these therefore molecules have "long" linkers between the variable domains, allowing the VL and VH domains in each molecule to associate to form an antigen binding site.

SUMMARY OF THE INVENTION

The present invention contributes further to the field of antibody fragments by providing polypeptides which are able to associate to form multivalent or multispecific multimers, particularly dimers. As discussed in greater detail below, in one aspect the present invention provides a polypeptide which comprises a first domain which comprises a binding region of an immunoglobulin heavy chain variable region, and a second domain which comprises a binding region of an immunoglobulin light chain variable region, the domains being linked but incapable of associating with each other to form an antigen binding site. Such polypeptides are able to associate to form multimers, such as dimers, the heavy chain binding region of one polypeptide associating with the light chain binding region of another polypeptide to form an antigen binding site. In the case of dimerisation two antigen binding sites are formed.

The term "diabody" has been coined to describe dimers according to the present invention. This term has already gained some recognition in the art. When used in the present application, the term is not intended to be construed in general discussion as applying only to dimers, except where context demands so. Trimerisation of the polypeptides is feasible, three antigen binding sites then being formed. Also, the term is used in relation to both multivalent and multispecific multimers.

Each domain of the polypeptide may be a complete immunoglobulin heavy or light chain (as the case may be) variable domain, or it may be a functional equivalent or a mutant or derivative of a naturally occuring domain, or a synthetic domain constructed, for example, in vitro using a technique such as one described in WO 93/11236 (Medical Research Council et al./Griffiths et al.). For instance, it is possible to join together domains corresponding to antibody variable domains which are missing at least one amino acid. The important characterising feature is the ability of each domain to associate with a complementary domain to form an antigen binding site. Accordingly, the terms "immunoglobulin heavy/light chain variable region" should not be construed to exclude variants which do not have a material effect on how the invention works.

A "derivative" is a substance which is related to a polypeptide. The derivative may differ by the addition, deletion, substitution or insertion of one or more amino acids, or by the linkage of another molecule. Changes may be made at the nucleotide or protein level. Markers such as enzymes, fluoresceins etc may be linked to the polypeptide.

The first and second domains may be linked without any intervening amino acid residues. Two such molecules will then associate to form an even smaller dimer. Furthermore, it may be that in certain cases the rigidity of molecules of this type means that the binding of antigen to one antigen binding site of the multimer will cause a conformational chance in another binding site in the multimer, a conformational change which may be useful if it enhances or reduces antigen binding, or even changes a catalytic activity of that other binding site.

In other embodiments, the domains of the polypeptide are linked by a peptide linker. The linker may be "short", consisting of too few amino acids to allow the VL domain of a chain to combine with the VH domain of that chain. This may be less than 10 amino acids, most preferably, 5, 4, 3, 2, or 1. It may be in certain cases that 9, 8, 7 or 6 amino acids are suitable. In some cases it may be "−1", ie with the VH and VL domains linked directly together, but with one of them missing an amino acid. In certain cases, the omission of more than one amino acid from one or both of the domains may be feasible.

In still further embodiments, the linker may consist of 10 or more amino acids so that, without a limiting structural feature, the domains of each chain would be able to associate with one another to form an antigen binding site. For instance, the linker may be 15 amino acids or longer. Suitable structural constraints include having cysteine residues within the linker with disulphide bridges joining them to reduce the effective length of the linker, in terms of how far the V domains are apart, by "looping" of the linker. This is discussed further infra. Those skilled in the art will be aware of other possibilities.

A dimer of two of the polypeptides may be bivalent, ie with each antigen binding site able to bind the same epitope. The binding specificity of the VH and the VL domains is determinable when the respective domain is in association with a complementary VL or VH, as the case may be. If the VH and VL domains of the polypeptide are derived from a parent antibody or antibody fragment (however obtained) then two of the polypeptides (identical, or with modification which may differ) will combine to form a bivalent dimer. Of course, the binding regions of polypeptides which will associate to form bivalent dimers may be derived from two different antibodies which bind the same epitope or may be synthetic, or obtained using any of the ways suggested to those skilled in the art.

In other cases, the binding region of an immunoglobulin heavy chain variable region and the binding region of an immunoglobulin light chain variable region may be, when in association with complementary light or heavy chain binding region respectively, able to bind different epitopes from each other. A dimer of two such molecules will be bispecific.

The polypeptide may be fused to additional amino acid residues. Such residues may be a peptide tag, perhaps to facilitate isolation, or they may be a signal sequence for secretion of the polypeptide from a host cell upon synthesis (for which see below). Suitably, secretory leader peptides are used, being amino acids joined to the N-terminal end of a polypeptide to direct movement of the polypeptide out of the cytosol.

The additional amino acids may be a polypeptide domain, such as antibody C domain and/or a surface component of an organism such as a bacteriophage, perhaps a filamentous bacteriophage such as fd or M13. Preferably, the surface component is GIII of bacteriophage fd or the equivalent from another filamentous phase.

A polypeptide according to the invention may in association with another such polypeptide form a dimer, with the binding region of an immunoglobulin heavy chain variable region of each polypeptide being in association with a binding region of an immunoglobulin light chain variable region of the other polypeptide.

In another embodiment, a three chain construct may be formed, the construct have two antigen binding sites. There, a polypeptide according to the present invention is allowed to associate with "free" VH and VL domains to form two antigen binding sites. For instance the three molecules may be (VHA-VLB), VHB and VLA, forming a bispecific construct, or they may be (VH-VL), VH and VL, to form a bivalent construct. This embodiment would be appropriate where the VH and VL domains could associate stably. The constructs would be more flexible than the standard diabody pairing, though still advantageously small in size.

Dimers, whether bivalent or bispecific are specifically encompassed by the present invention. As discussed the two polypeptides in a dimer may be different from one another or they may be the same. Where they are different, the order of the first and second domains ("VH" and "VL") may conceivably be the same or different. However, most preferably the N-terminal to C-terminal order of the first and second domains is the same in each polypeptide. A bispecifc dimer might then be represented as N-(VHA-VLB)=C/N-(VHB-VLA)-C or N-(VLA-VHB)-C/N-(VLA-VHA)-C.

Also provided by the present invention are diverse repertoires of the polypeptides. Within such a diverse repertoire, different pairings (or trimerisation etc . . . ) of polypeptides may result in the formation of dimers with different binding specificities, either bivalent or bispecific. Diverse repertoires of dimers are encompassed by the present invention.

The present invention also provides nucleic acid comprising a sequence encoding a polypeptide according to the invention, and diverse repertoires of such nucleic acid. The nucleic acid may comprise nucleic acid of an RNA splice site between nucleic acid encoding the first domain and nucleic acid enoding the second domain.

A self splicing group I intron such as that from Tetrahymena (T. R. Cech Ann. Rev. Biochem. 59:543–568, 1990) may be inserted. Splicing out of the intron occurs at the RNA level leaving behind the internal guiding sequence of the intron, which would encode three amino acids between the two domains of the diabody. The self-splicing may be designed so that the number of amino acids remaining is different, for instance, in Example 24, 5 and 6 amino acid linkers are formed.

Other group I introns or group II self splicing introns may be used. Self splicing introns may be used in combination with reconbination, for example, at the loxP site (see below), in the construction of diabody molecules. For example, a loxP site may be included in a self splicing intron between the two antibody domains of a polypeptide chain. This may, for example, be recombined at the DNA level through a loxP site on another replicon carrying another variable domain gene and the appropriate region of a self splicing intron. Self splicing at the RNA level following transcription will now lead to a diabody polypeptide chain with a new combination of variable domains.

The nucleic acid may comprise, between nucleic acid encoding the first domain and nucleic acid encoding the second domain, nucleic acid encoding a site for recombination in vivo or in vitro.

For instance the loxP site, a 34 bp site at which recombination is catalysed by the protein Cre (Hoess et al., *PNAS USA* 79: 3398–3402, 1982, and Stemberg et al., *J. Miol. Biol.*; 150: 467–486, 1981).

This system has been used in the preparation of antibodies displayed on phage (P. Waterhouse et al., *Nuc. Acid Research* 21: 2265–2266, 1993; and WO93/19172).

The invention also provides a vector comprising such nucleic acid. The vector may comprise nucleic acid necessary for expression of the polypeptide. The vector may comprise nucleic acid for secretion of the polypeptide upon expression.

The vector may comprise nucleic acid encoding two of said polypeptides, a first polypeptide and a second polypeptide. There may be, between nucleic acid encoding the first polypeptide and nucleic acid encoding the second polypeptide, nucleic acid comprising a site for recombination in vivo or in vitro.

According to a futher aspect of the present invention there is provided a vector comprising nucleic acid encoding a first polypeptide and nucleic acid encoding a second polypeptide, each of the polypeptides comprising a first domain which comprises a binding region of an immunoglobulin heavy chain variable region, and a second domain which comprises a binding region of an immunoglobulin light chain variable region, the first domain of each polypeptide being linked to the second domain of that polypeptide but incapable of associating with it to form an antigen binding site, the nucleic acid encoding the first polypeptide being linked to nucleic acid encoding a signal sequence for export of the first polypeptide from a host cell upon expression, the nucleic acid encoding the second polypeptide being linked to nucleic acid encoding a signal sequence for export of the second polypeptide from a host cell upon expression and nucleic acid encoding a surface component of a filamentous bacteriophage for display of the second polypeptide on the surface of a bacteriophage particle upon expression, the vector being capable of being packaged within a bacteriophage particle.

Expression from such a vector will produce, on the surface of a bacteriophage particle a dimer of the two first and second polypeptides, one being attached to the particle by means of the surface component, the other being associated with it. This allows selection of displayed diabodies, with encoding nucleic acid, packaged within particles being easily isolated. Techniques of this kind are described in WO 92/01047.

Expression of a repertoire of diabodies and their display on secreted replicable genetic display packages, such as bacteriophage, is valuable for selection of binders for an antigen of interest from among many different possible combinations of heavy and light chain—many different possible binding specificities.

In another aspect the invention provides a vector comprising:

(a) nucleic acid encoding a first polypeptide domain, which comprises a binding region of an immunoglobulin heavy chain variable region, and a second polypeptide domain, which comprises a binding region of an immunoglobulin light chain variable region; and (b) nucleic acid encoding a surface component of a filamentous bacteriophage;

expression of nucleic acid (a) producing a polypeptide ("A") comprising the first and second domains linked but incapable of associating with each other to form an antigen binding site;

expression of nucleic acid (a) together with nucleic acid (b) producing a polypeptide ("B") comprising the first and second domains linked but incapable of associating with each other to form an antigen binding site, fused to a surface component of a filamentous bacteriophage for display of the polypeptide (B) on the surface of bacteriophage particles;

nucleic acid (b) being linked to nucleic acid (a) by nucleic acid including an intervening suppressible stop codon.

A suppressible stop codon allows the translation of nucleotide sequences downstream of the codon in suppressor host cells but in non-suppressor cells translation may end at the codon. Examples of suppressible translational stop codons are the amber, ochre and opal codons. In fact, in most suppressor host cells, such as SupE cells, there is some "slippage" so there is some translation beyond the suppressible stop and some translation stopping at the stop.

This is useful, because it allow a vector according to this aspect of the present invention to be used to express both soluble polypeptides and polypeptides fused to a component of a bacteriophage, or other display package, for association of a dimer on the particle surface. Preferably the nucleic acid of the vector includes nucleic acid encoding secretory leader peptides or other signal sequences, so that the polypeptides are secreted from the cytosol of host cells into the periplasm (Skerra et al., *Science* 240: 1038: 1041, 1988; Better et al., *Science* 240: 1041–1043, 1988; WO92/01047).

The present invention also encompasses host cells transfected with any vector according to the present invention. Where the vector is one which has a suppressible stop codon as described, preferably the host cell is capable of providing conditions for co-expression of both polypeptides A and B (as discussed ie one which is VH-VL and one which is VH-VL fused to a surface component of a bacteriophage or other suitable organism).

The invention also provides a method of making polypeptides, dimers or other multimers according to the invention, which comprises culturing a host cell transfected with a vector under conditions for expression of the polypeptide(s), which may be conditions for co-expresssion of the said polypeptides A and B. The method may involve recovery of the polypeptide(s), dimer(s) etc from the host cell culture, either from the host cell or the medium. Recovery from the host cell may be from the periplasm, following secretion from the cytoplasm, or from inclusion bodies. Refolding from denaturing condition may be needed. The recovery is preferably by selection by binding with antigen of interest.

Many uses of the polypeptides according to the invention are envisaged, some of which are described infra. One use of particular interest is in assay for antigen, either homogeneous assay or heterogeneous assay.

In another aspect of the invention, a bispecific dimer is provided having (i) a first polypeptide which has a first domain, which comprises a binding region of an immunoglobulin heavy chain variable region, a second domain, which comprises a binding region of an immunoglobulin light chain variable region, and a polypeptide linker linking the first and second domains and allowing association of the domains with each other to form an antigen binding site; and (ii) a second polypeptide which has a first domain, which comprises a binding region of an immunoglobulin heavy chain variable region, a second domain, which comprises a binding region of an immunoglobulin light chain variable region, and a polypeptide linker linking the first and second domains and allowing association of the domains with each other to form an antigen binding site. The first domain of the first polypeptide and the second domain of the second polypeptide associate to form an antigen binding site which has a first binding specificity, while the second domain of the first polypeptide and the first domain of the second polypeptide associating to form an antigen binding site which has a second binding specificity.

In another aspect of the present invention there is provided a dimer of
(i) a first polypeptide comprising a first domain which comprises a binding region of an immunoglobulin heavy chain variable region, and a second domain which comprises a binding region of an immunoglobulin light chain variable region, the domains of the first polypeptide being linked but incapable of associating with each other to form an antigen binding site; and
(ii) a second polypeptide which has a first domain, which comprises a binding region of an immunoglobulin heavy chain variable region, a second domain, which comprises a binding region of an immunoglobulin light chain variable region, and a polypeptide linker linking the first and second domains and allowing association of the domains of the second polypeptide with each other to form an antigen binding site;
the first domain of the first polypeptide and the second domain of the second polypeptide associating to form an antigen binding site; and
the second domain of the first polypeptide and the first domain of the second polypeptide associating to form an antigen binding site.

Such dimers may be bivalent or bispecific.

Various modifications to the polypeptides of the dimer may be made, in the same manner as is described supra for other aspects of the invention. Likewise, the present invention encompasses vectors comprising nucleic acid which encodes first and second polypeptides which are able to form a dimer according to this aspect of the invention, host cells transfected with such vectors and methods which comprise culturing host cells under conditions for expression of the first and second polypeptides, and recovery of a dimer which has bispecificity.

Polypeptides, multimers, nucleic acid, vectors, repertoires etc. disclosed by the experimental Examples infra are provided as aspects of the present invention.

instance the present invention also provides molecules which bind any of the following: a cell surface protein, a Fc receptor, a tumour specific marker, CEA, a virus HIV 1, a small chemical molecule, a hormone, a cytokine, TNFα, an antibody, the idiotope of an antibody.

Dimers wherein the binding of an antigen to one antigen binding site of the dimer affects the binding of an antigem to the other binding site of the dimer are provided.

Those dimers wherein alterations of the linker lead to an improvement in antigen binding affintiy of at least one of the binding sites of the dimer are encompassed by the present invention.

Assays, which may be diagnostic, are provided, and may involve crosslinking of antigen or agglutination of cells. They may involve the binding of one antigen on a surface and the binding of an antigen in solution, and may involve detection using surface plasmon resonance. Molucules provided by embodiments of the present invention may bind to antigens on two different cell surfaces.

Additionally, the present invention provides pharmaceuticals comprising the polypeptides or multimers of the present invention, and the use of the polypeptides or multimers in the preparation of medicaments. Methods of treatment using polypeptides or multimers according to the present invention are encompassed.

Many other aspects of the present invention are discussed infra. Others will be apparent to those of ordinary skill in the art.

The present invention will now be discussed further by way of illustration and exemplification, with some comparison with existing art in the field of bivalent and bispecific antibodies and antibody fragments. What follows should not be interpreted as limiting the invention in any way. The following figures are mentioned (additional keys at end of the description):

BRIEF DESCRIPTION OF THE FIGURES

FIG. 1 shows hybrid-hybridoma, designer bisAbs and bivalent antibody fragments. The bisAbs are given above the dotted line and the bivalent Abs below: A: hybrid-hybridoma, B: bispecific Fab'$_2$, C: bispecific F(ab'-zipper)$_2$, D: bispecific scFv$_2$, E: three chain bispecific fragment, F: bispecific diabody, G: bivalent (FvCys)$_2$, H: bivalent (Fvzipper)$_2$, I: scFvCH3$_2$ (P. Holliger, G. Winter unpublished results), J: bivalent diabody, K: bivalent F(ab'-zipper)$_2$, L: bivalent Fab'$_2$.

Figure 2:
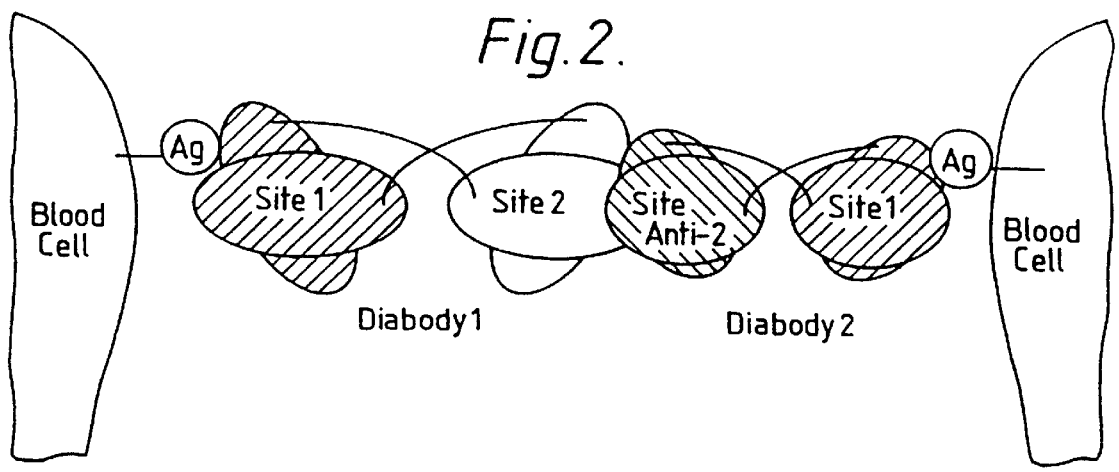

FIG. 2 shows agglutination using two linking diabody molecules:

Diabody 1—with one specificity directed against a blood cell surface antigen (Site 1) and the other specificity directed against an antigen not normally present in blood, so that this binding site (Site 2) is free.

Diabody 2—with one specificity being anti-idiotypic directed against Site 2 on the first diabody (Site Anti-2) and the other specificity directed against the blood cell surface antigen (Site 1). This format will allow agglutination of blood cells with the distance spanned being the length of two diabody molecules as shown.

Figure 3:
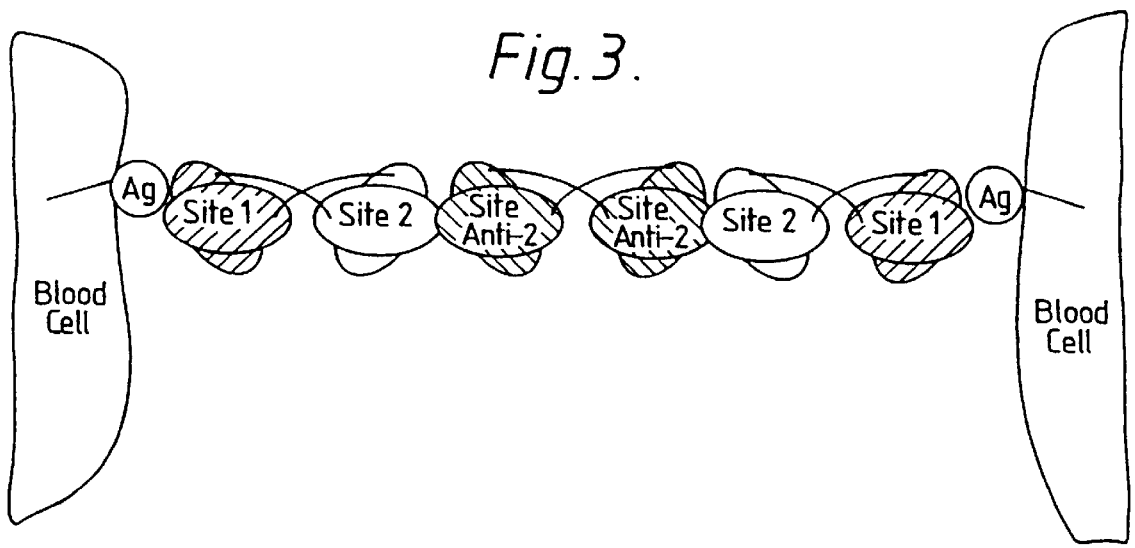

FIG. 3 shows agglutination using three linking diabody molecules:

Diabody 1—with one specificity directed against a blood cell surface antigen (Site 1) and the other specificity directed against an antigen not normally present in blood, so that this binding site (Site 2) is free.

Diabody 2—with both specificities being anti-idiotypic directed against Site 2 on the first diabody (Site Anti-2). In this format when two molecules of diabody 1 bind to different red blood cells diabody 2 can bind to each of these diabody 1 molecules at Site 2 thus forming a complex of three diabody molecules spanning the distance between the two red blood cells as shown.

Figure 4:
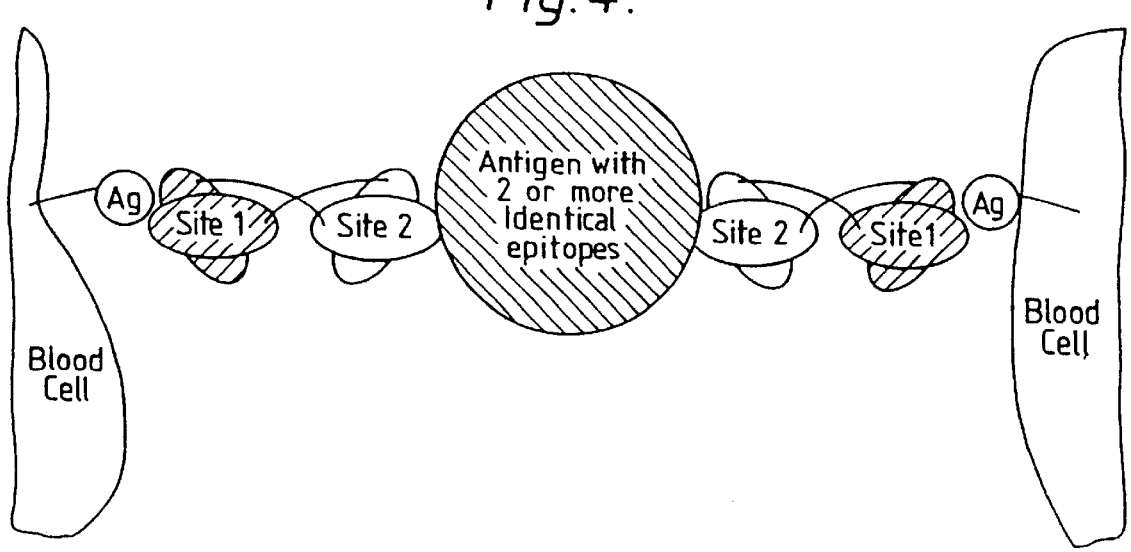

FIG. 4 shows agglutination using two diabody molecules and one non-diabody molecule making link:

Diabody 1—with one specificity directed against a blood cell surface antigen (Site 1) and the other specificity directed against another non-diabody antigen which is to be added to the assay (Site 2).

Non-diabody antigen molecule—this would be a large molecule to which Site 2 of diabody 1 is directed. In this format two molecules of diabody 1 bind to two different cells. The non-diabody molecule will bind to both diabody molecules through Site 2 crosslinking the red blood cells.

Figure 5:
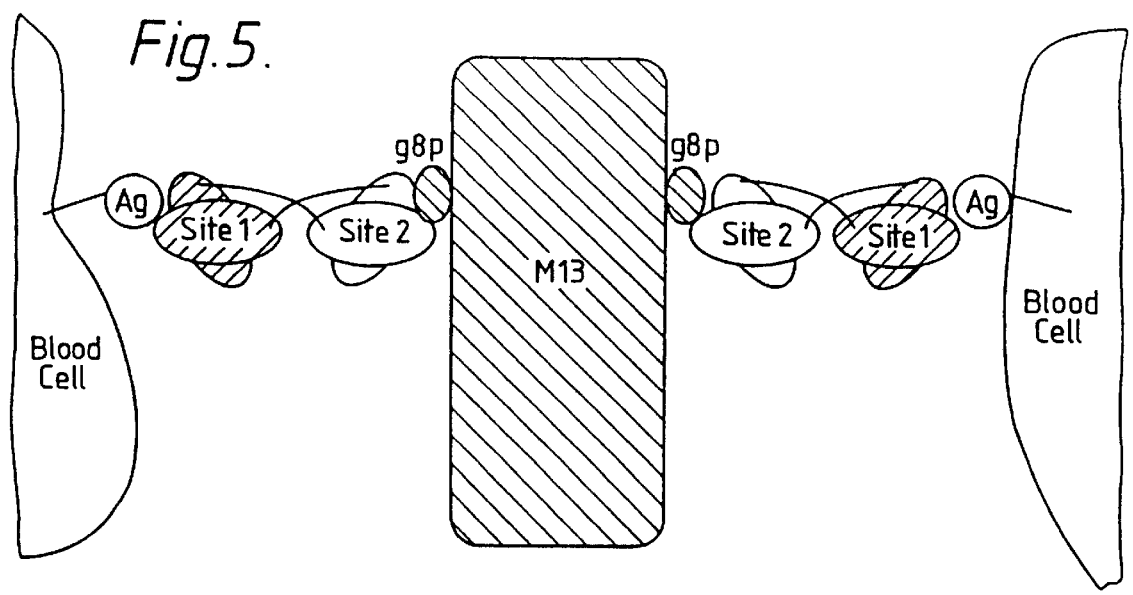

FIG. 5 shows agglutination using a whole organism in the crosslinking reaction. In the above cases the linking molecule for agglutination is a protein molecule. The principle can be extended to the use of organisms to crosslink such as bacteriophage M13 or bacteria such as $E. coli$.

In format (iii) above, Site 1 of diabody 1 could be directed against a cell surface marker and Site 2 directed against a bacteriophage surface molecule such as the gene 8 protein.

Figure 6:
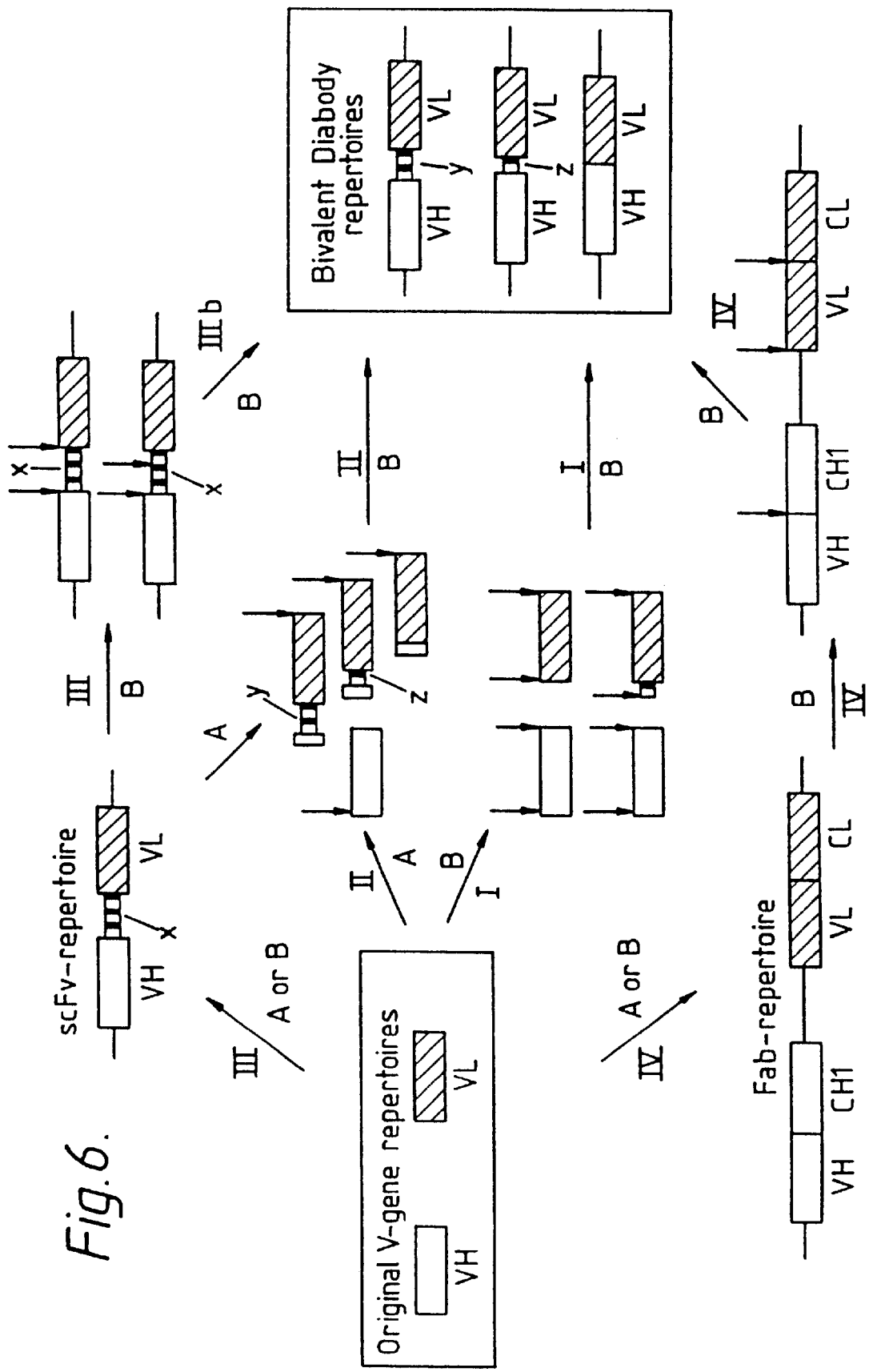

FIG. 6: Construction of bivalent diabody repertoires. Various cloning routes can be used to make bivalent diabody repertoires. Starting points can be diverse repertoires of VH and VL genes or V-gene repertoires already formattted as scFv or Fab fragments (and possibly enriched for binders). Details are explained in the text.

Figure 7:
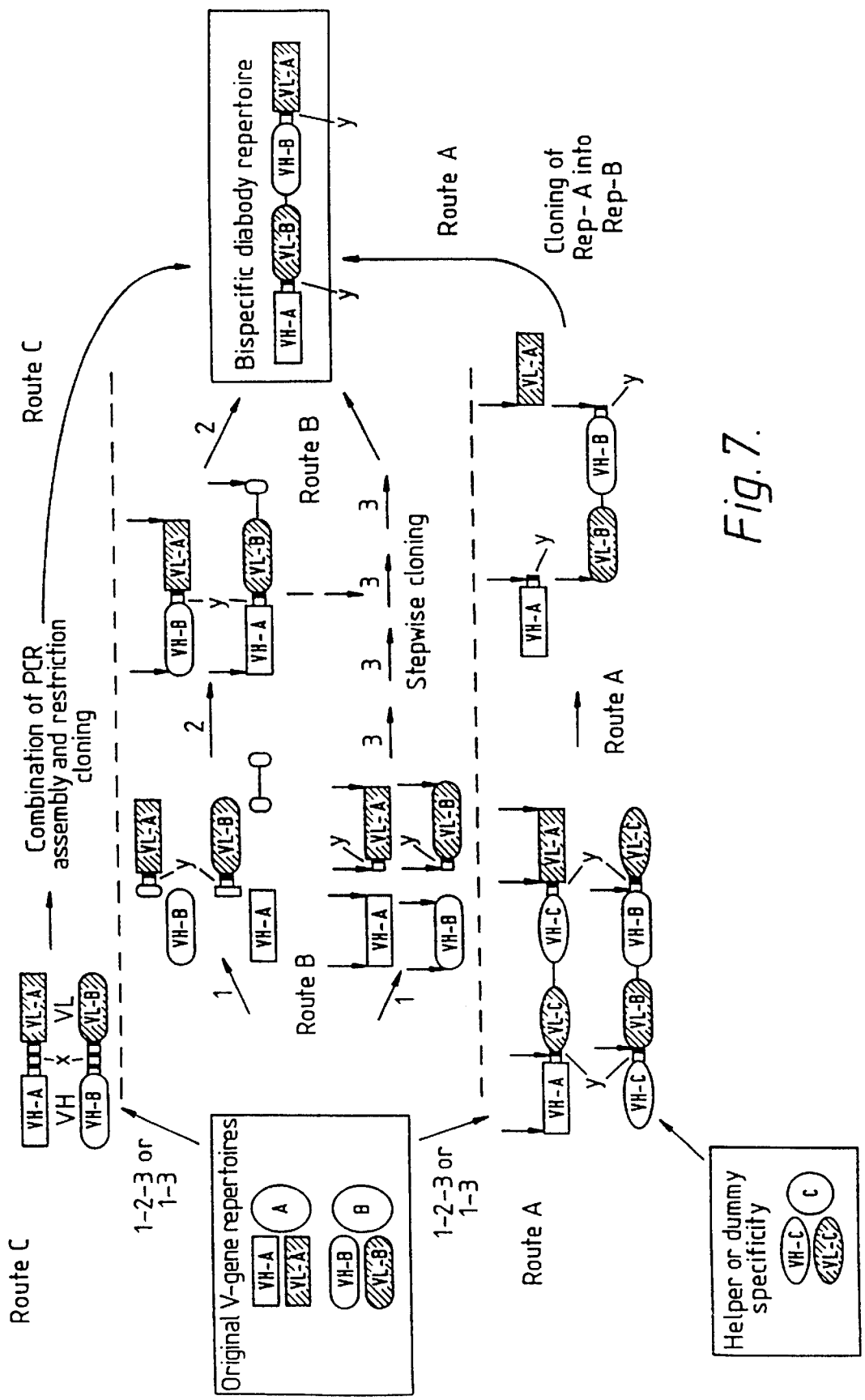

FIG. 7: Construction of bispecific diabody repertoires. Various cloning routes can be used to make bispecific diabody repertoires. Starting points can be diverse repertoires of VH and VL genes (Route B) or V-gene repertoires already formattted as scFv or Fab fragments (and possibly enriched for binders) (Route C). In both routes, V-gene repertoires can be cloned as bispecific diabodies by stepwise restriction cloning or by PCR assembly. Alternatively, a repertoire of diabodies can be made using helper or dummy V-genes (Route A). More details are explained in the text.

Figure 8:
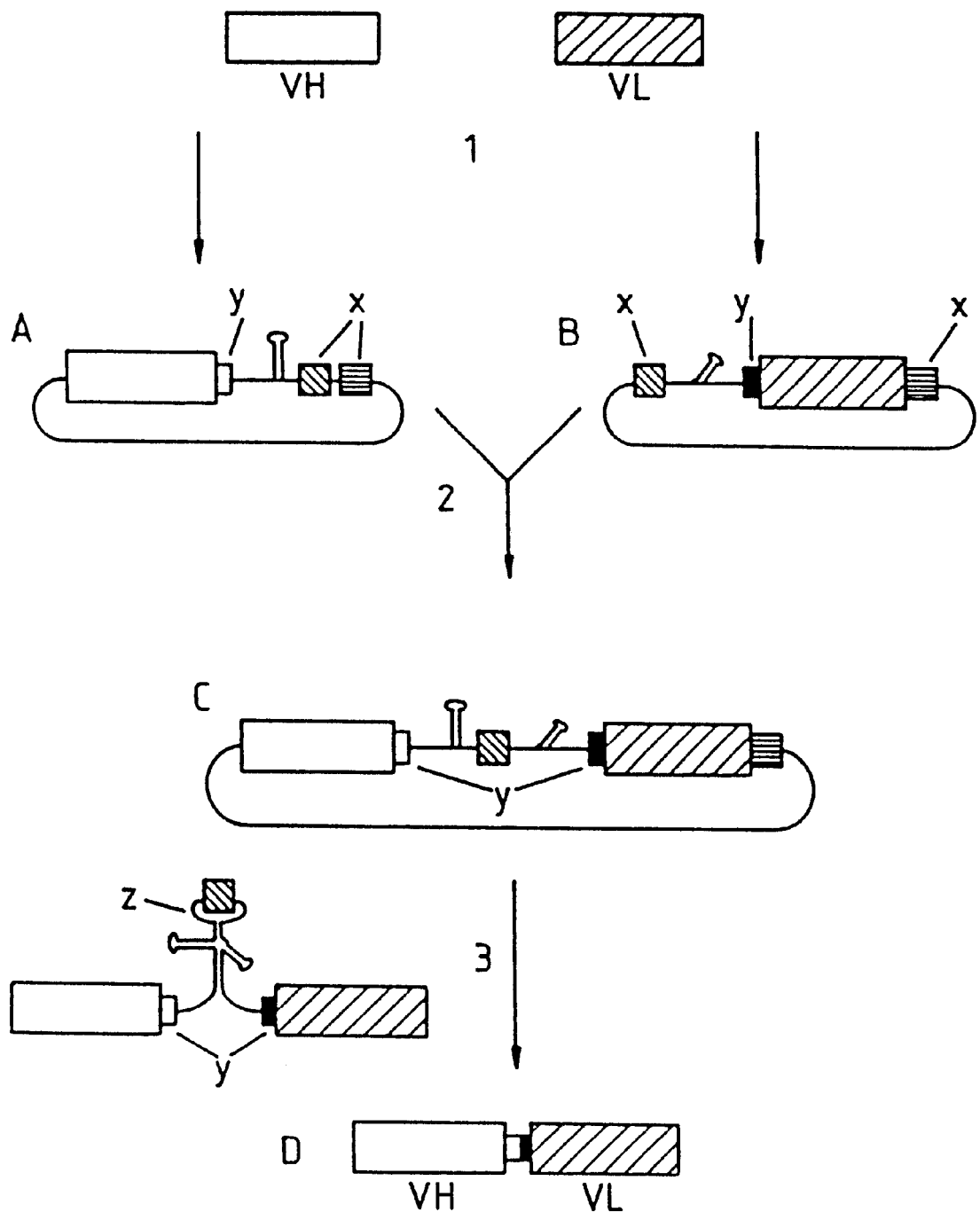

FIG. 8: Construction of large bivalent diabody repertoires. By taking advantage of both the self splicing intron from Tetrahymena, and the loxP recombination system, large bivalent diabody repertoires may be made. The VH-containing replicon is combined with the VL containing replicon via a Cre/loxP mediated recombination. After the recombination, which takes place at the DNA level, the resulting diabody gene is transcribed, and the intron and the loxP site between VH and VL genes are spliced out. See text for more details.

Figure 9:
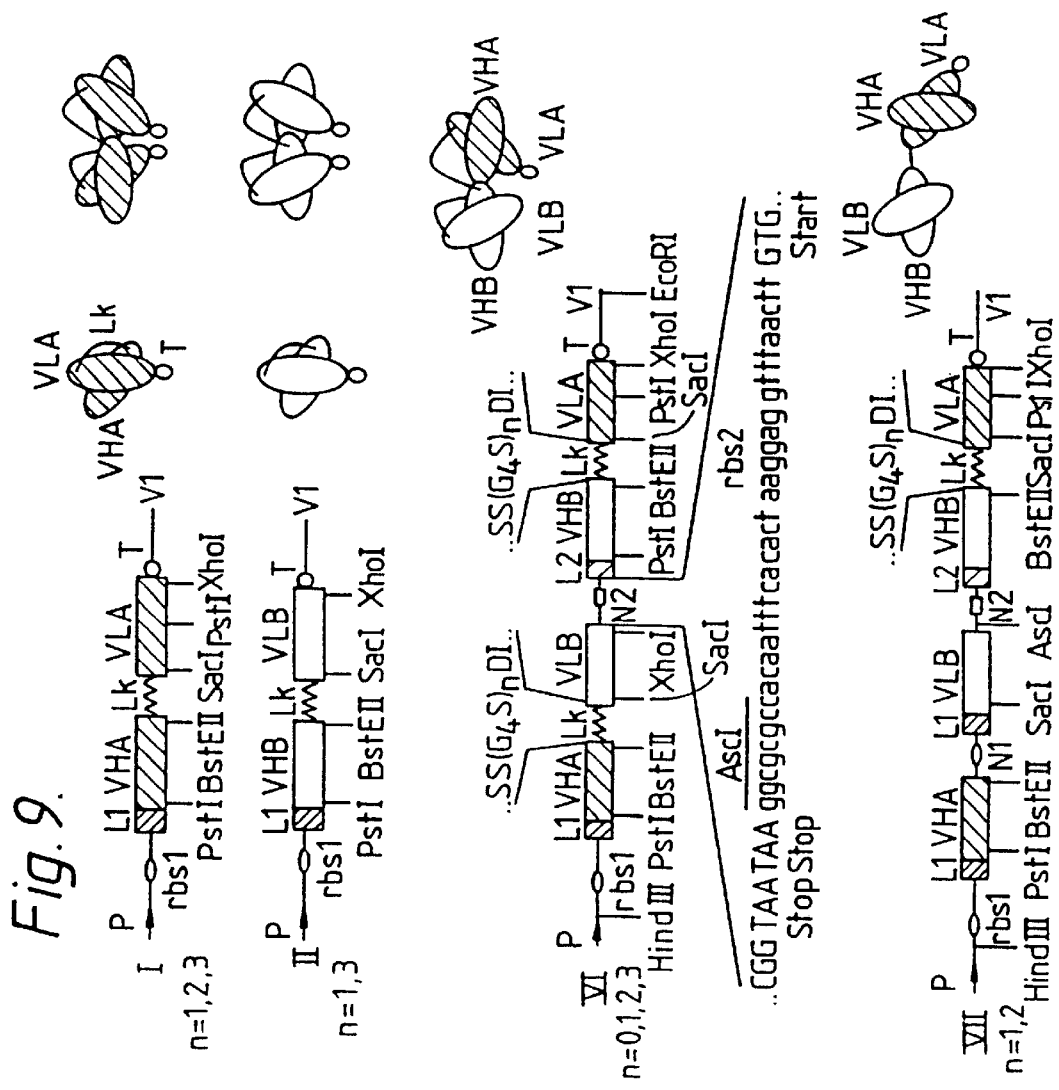

FIG. 9 shows vector constructs from Example 1. A. Constructs (III–V) used to build the expression constructs (I, II, VI, VIII) are illustrated. (Constructs VIII and IX encoding VHB-VLA and VHA-VLB respectively are not shown, but are described in example 1) Constructs III–V were cloned in fd-tet-DOG1 (V2) (H. R. Hoogenboom et al, supra), and the other constructs in a pUC19-derived expression vector (V1) (L. Riechmann et al 1992 supra) under the control of the lac promotor (P) and with a peptide tag (T) (S. Munro & H. R. B. Pelham 1986 supra). The V-genes of antibodies NQ11 (VHA, VLA) and D1.3 (VHB, VLB) have internal PstI, BstEII, SacI and XhoI restriction sites as in (R. Orlandi et al Proc. Natl. Acad. Sci. USA 86: 3833–3837 1989; E. S. Ward et al 1989 supra): in addition VLA has an internal PstI site. The polypeptide linker (Lk) or non-coding region (N1 or N2) between VH and VL of the same chain is marked. Lk consists of a number of repeats (n=0–3) of Gly$_4$Ser (SEQ ID NO: 86. N1 includes a ribosome binding site (rbs1) as described (E. S. Ward et al. 1989 supra) and N2 a consensus ribosome binding site (rbs2) as described (J. McLaughlin et al J. Biol. Chem. 256: 11283–11288 1981). The signal sequences for secretion of fragments into the bacterial periplasm are the pelB signal sequence (L1) (E. S. Ward et al. 1989 supra) and the phage fd gene 3 signal sequence (L2) (A. N. Zacher et al. Gene 9: 127–140 1980). Locations of PCR primers 1–8 are shown in the constructs III–V. Schematic depiction of protein products as deduced from Table 1 are also given.

FIG. 10 shows BIAcore and FPLC analysis of antibody fragments. Lysates from FabD1.3 (panel A) are compared with lysates from construct VI (panel B) or construct VII (panel C) using a BIAcore sensorchip coated with HEL and detecting bound mass as resonance units (RU). a, baseline; b–d injection of fragment; d–e, dissociation of bound fragment; e–h, injection of phOx-BSA. DRU between e and h reflects the amount of phOX-BSA that has been bound.

Figure 11:
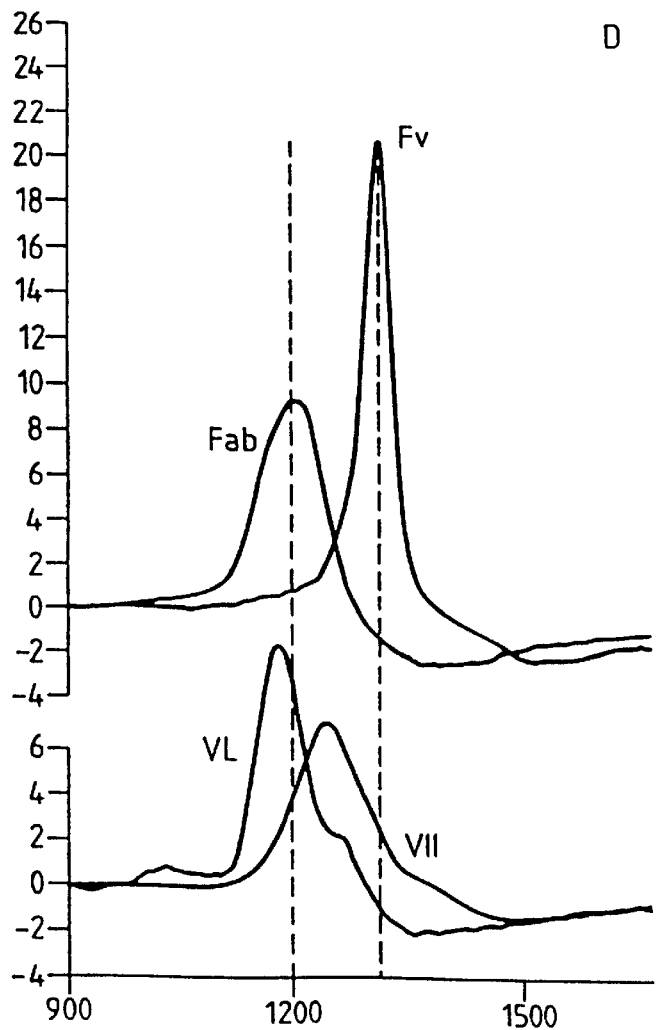

FIG. 11 illustrates on-line detection by BIAcore of several fragments emerging after fractionation of the lysates by FPLC (Superdex S-75 10/30 in PBS buffer with 0.2 mM EDTA, 0.05% sodium azide) with the change in mass bound to the HEL-coated chip plotted against time (–dRu/dt). Points above zero indicate association with HEL, points below zero indicate dissociation. In the top row the traces for chimaeric FabD1.3 (Mr 47.6k) and FvD1.3 (Mr 25.7k) are plotted, and in the bottom row for dimer constructs VI (Mr 53.4k) and VII (Mr 51.7k) (both 15 residue linkers). Mr calculated from the amino acid sequences.

Figure 12:
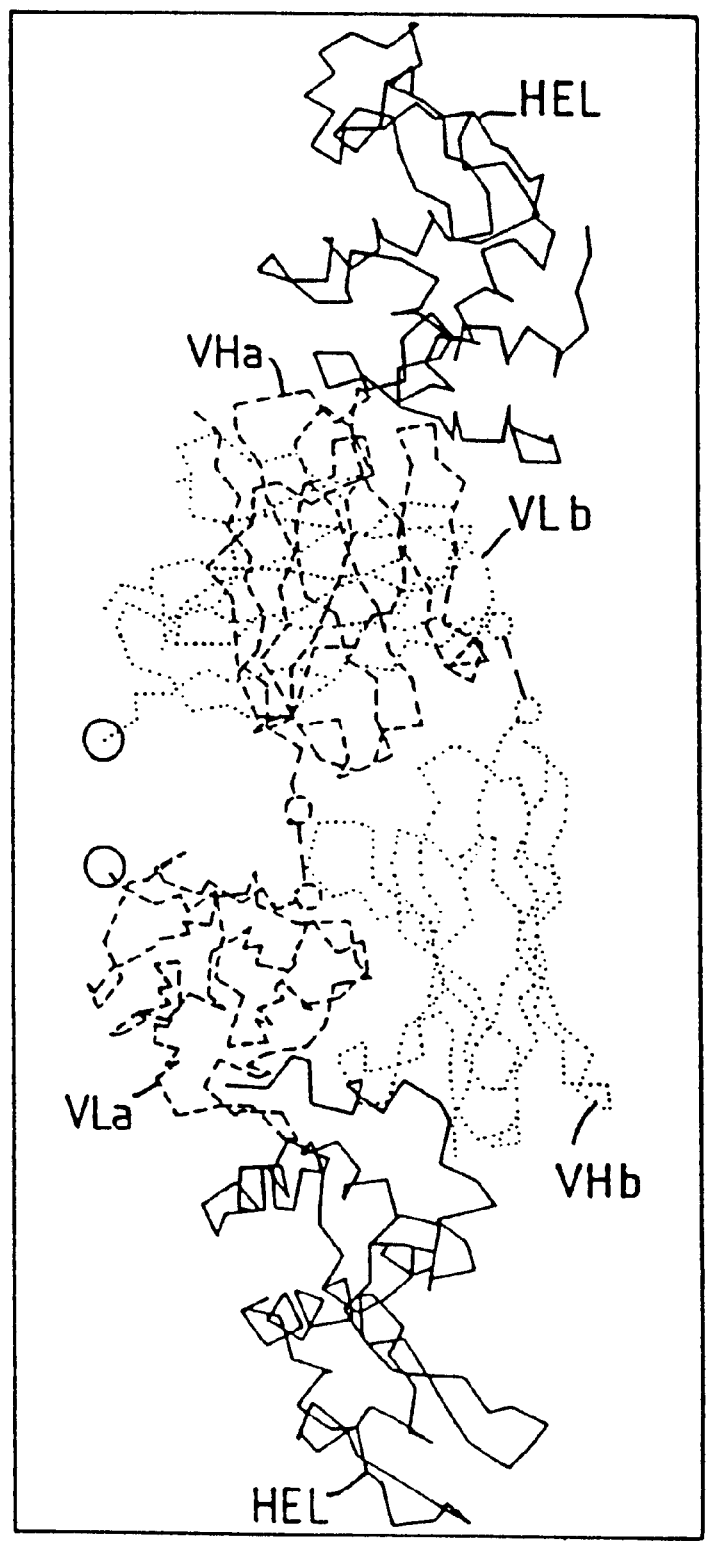

FIG. 12 Modelling. The model of the bivalent D1.3 diabody illustrates the apposition of the N-and C-termini of the linked domains (marked with solid circles and connected by dotted line), the packing of the domains and the proximity of the C-termini of the VL domains (marked with an open circle). The Ca trace for VH and VL domains on the same polypeptide chain (a or b) are thick or thin lines respectively, to show that each antigen binding site is formed from the VH and VL domain of the two different chains a and b. Thus VHa is associated with VLb, and VHb with VLa. The bound antigen hen egg lysozyme (HEL) is shown at the top and bottom of the figure.

Figure 13:
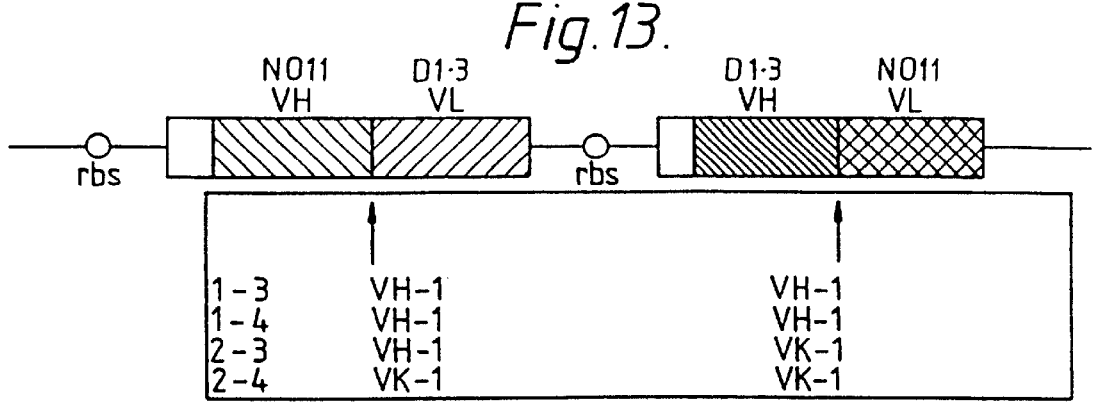

FIG. 13 shows four –1 constructs made by deletions of amino acids at the N-terminus of the VL domain or at the C-terminus of the VH domain of the bispecific diabody NQ11/D1.3 (example 2).

Figure 14:
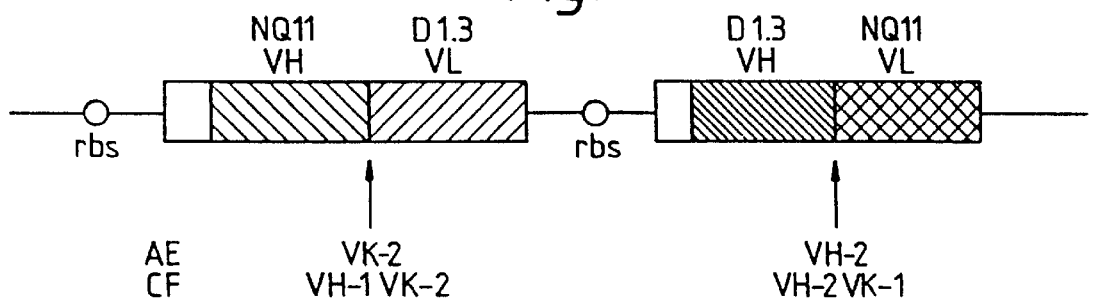

FIG. 14 shows −2 and −3 constructs made by deletion of amino acids at the junction of VH and VL domains in the bispecific diabody NQ11/D1.3 (example 2).

Figure 15:
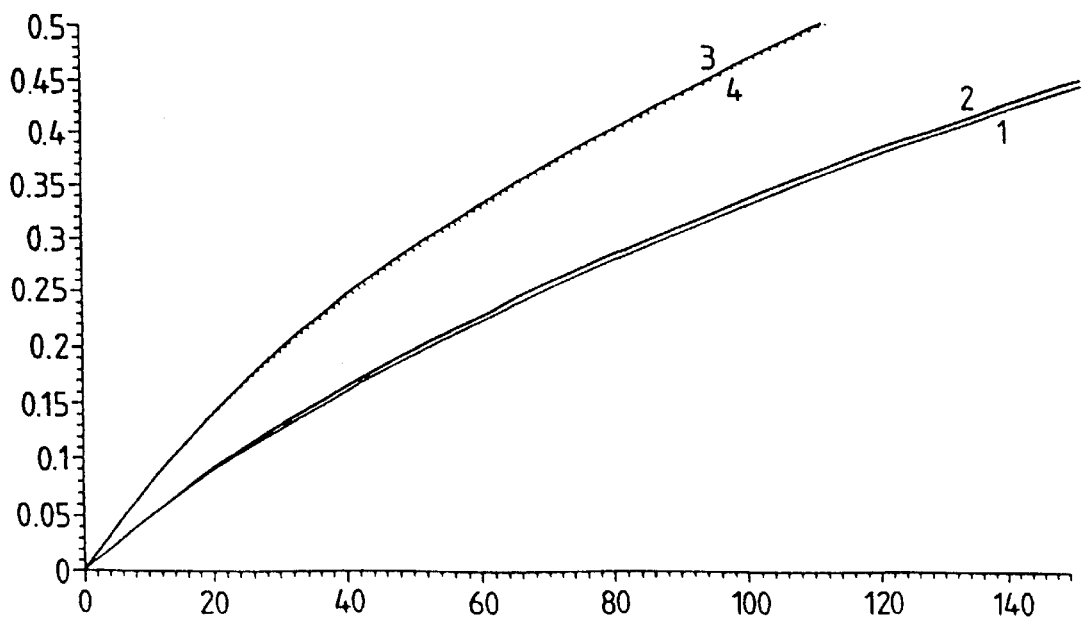

FIG. 15 shows off-rate curves for the dissociation of the NQ11/B1.8 bispecific diabody from the phOx-BSA surface (example 4).

FIG. 16 shows the corrected equilibrium binding (resonance units at equilibrium "Req") curves for binding of NQ11/B1.8 diabody to an Ox-BSA surface in the presence and absence (control) of NIP. The upper portion shows the curve for surface s2 and the lower portion the curve for the surface s3 (example 4)

FIG. 17 shows Scatchard plots for the binding of the NQ11/B1.8 Ox/NIP diabody to s2 phOx-BSA surface upper portion-control; lower portion-plus 1 μM NIP (example 4)

FIG. 18 shows Scatchard plots for the binding of the NQ11/B1.8 Ox/NIP diabody to s3 phOx-BSA surface upper portion-control; lower portion-plus 1 μM NIP (example 4)

Figure 19A:
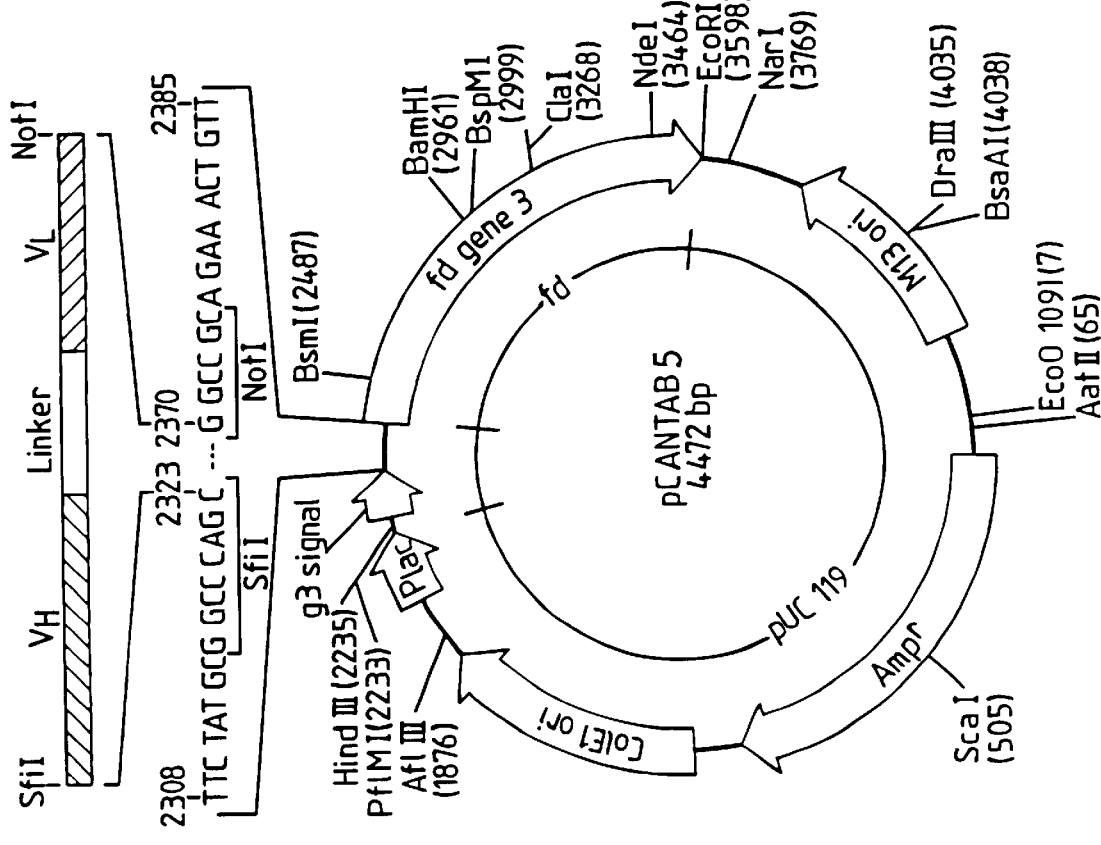
Figure 19B:
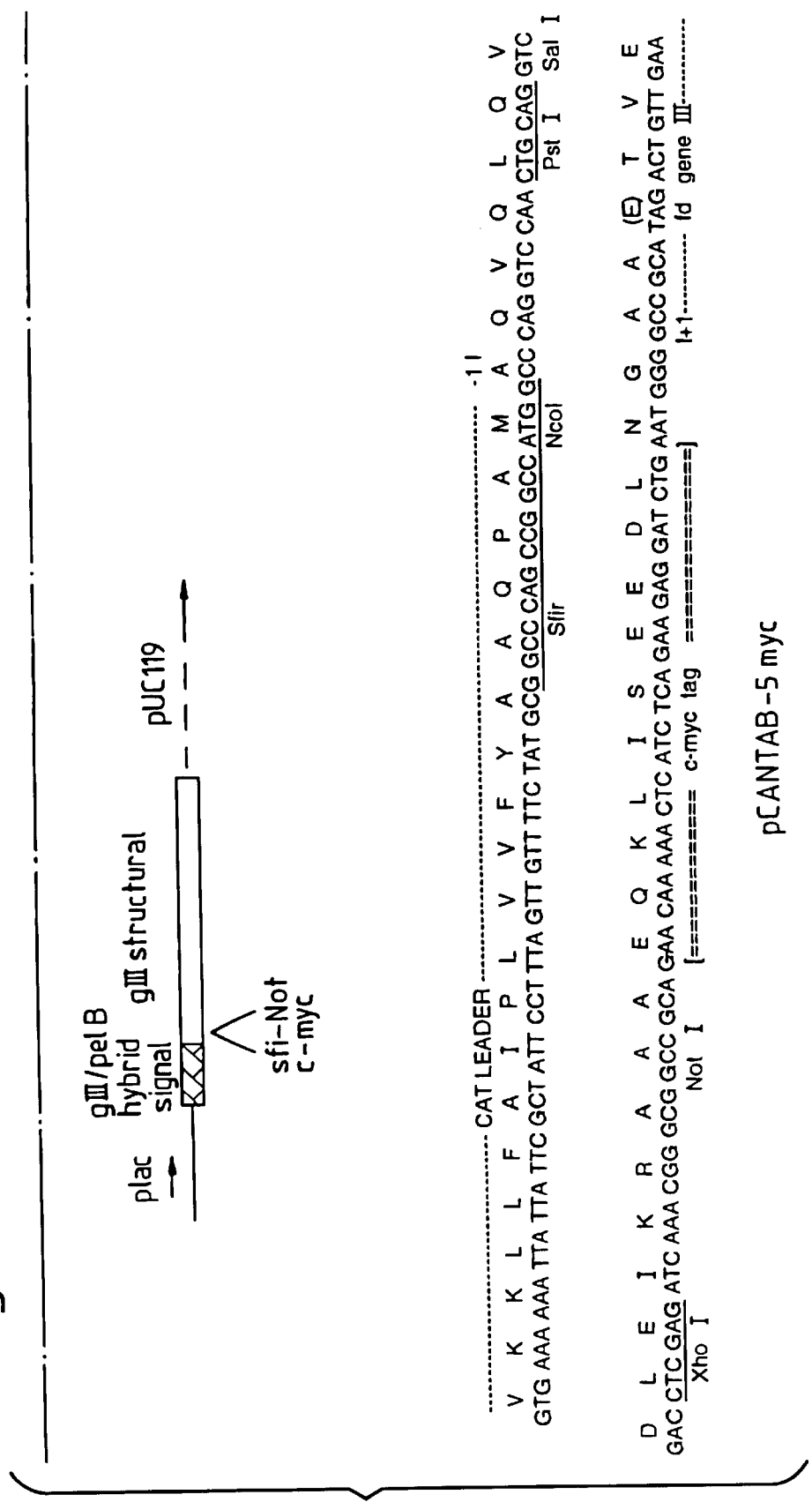

FIGS. 19a and 19b show vector pCANTAB5 and its derivative pCANTAB5-myc.

FIG. 20 shows the polylinker region (SEQ ID NOS: 96 & 97) of the vector pCANTAB6.

Figure 21:
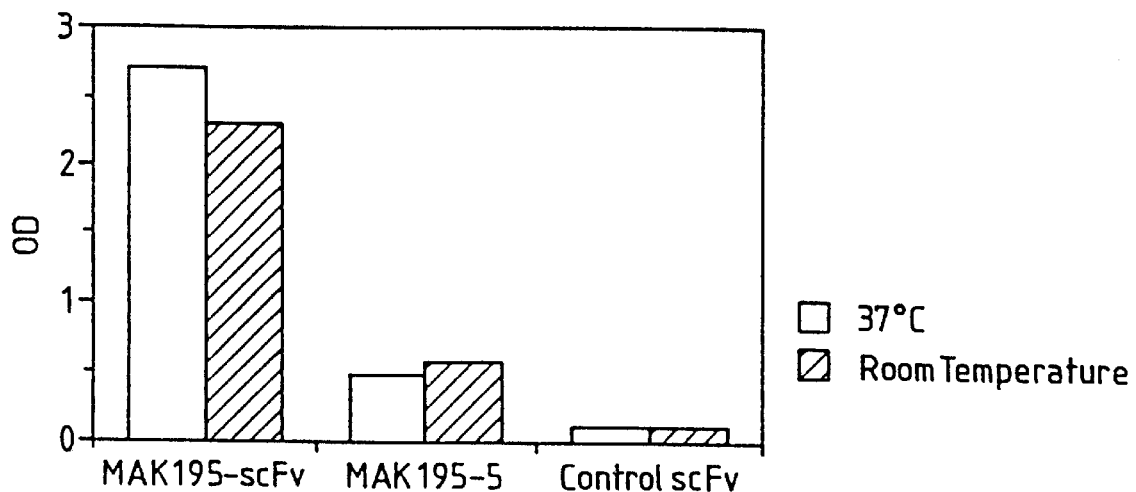

FIG. 21: MAK195 diabody ELISA. MAK195 diabody (5 residue linker) and scFv were prepared by induction as described in the text (using 24° C. for overnigth growth), and samples analysed for binding to human TNF in ELISA done at Room Temperature or 37° C. The control scFv is directed against a different antigen and therefore does not bind TNF.

Figure 22:
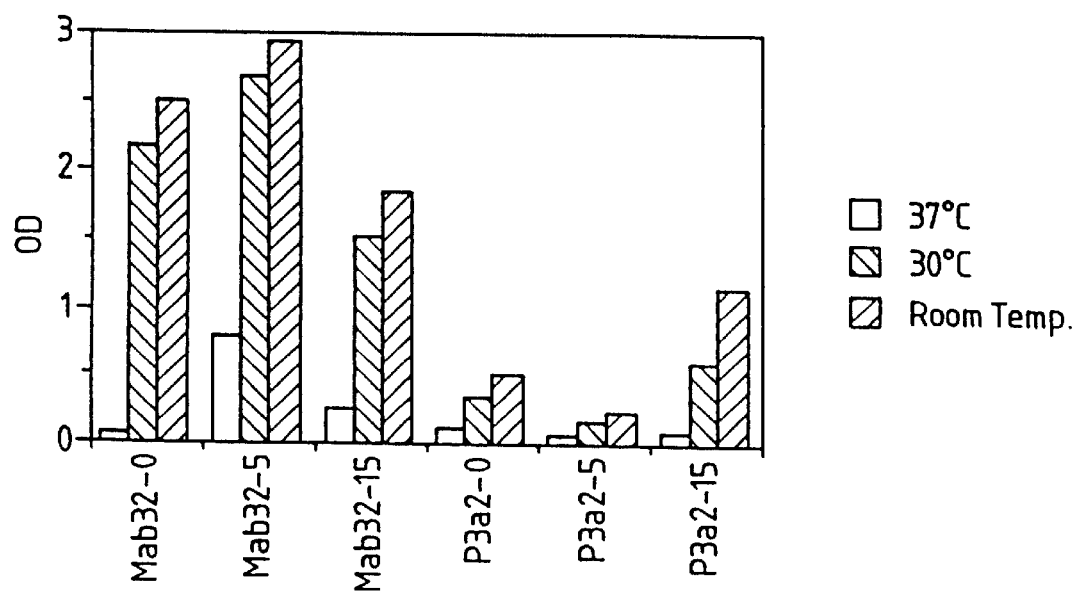

FIG. 22: Mab32 and P3A2 diabody ELISA. Mab32 diabodies (0 and 5 residue linker) and Mab32 scFv fragments were prepared by induction as described in the text, and samples analysed for binding to human TNF in ELISA.

Figure 23:
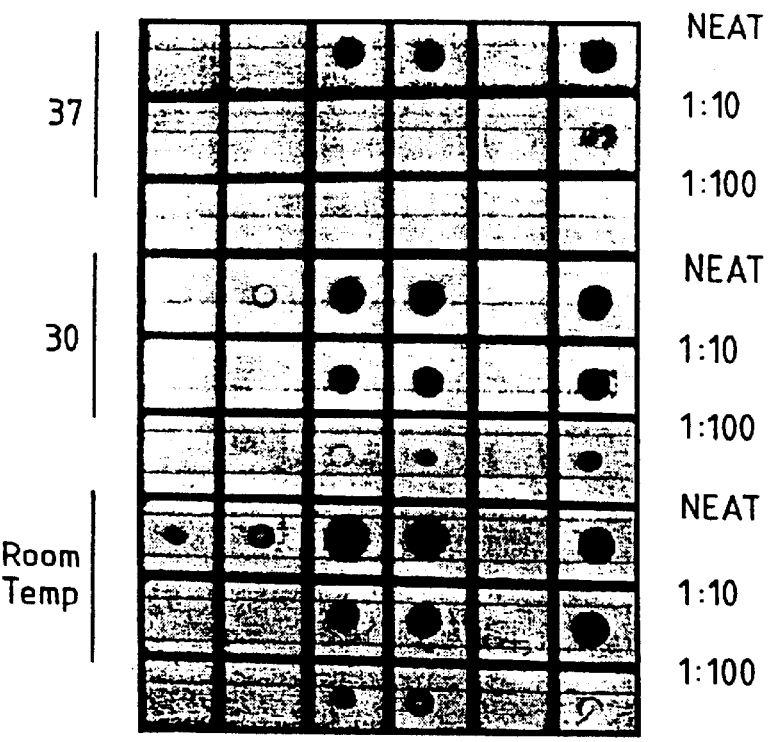

FIG. 23: Mab32 and P3A2 diabody Western blot. Mab32 diabodies (0 and 5 residue linker) and Mab32 scFv fragments were prepared by induction of bacteria carrying the appropriate plasmid using 1 mM IPTG and various temperatures for the overnight growth (indicated on the left). Diabody was detected in the spotted samples (undiluted, neat; and 10-fold dilutions) of the culture supernatant as described in the text.

Figure 24:
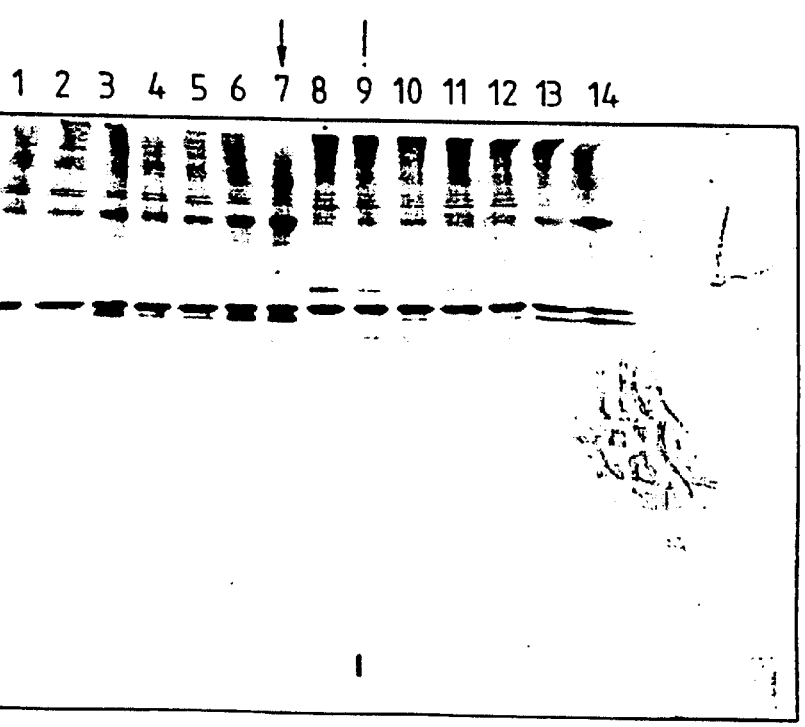

FIG. 24 (gel I) shows a non-reducing SDS-PAGE gel of intracellularly expressed Mab32 diabody preparations refolded under various conditions. Track 7 shows the folded state of material after the cycling procedure and incubation overnight in 50M Tris-HCl, 0.5M NaCl in the absence of added redox cycling agents. Track 9 shows the conditions used in example X for incubation overnight after refolding—50 mM Tris-HCl, 0.5M NaCl with 5 mM GSH, 0.5 mM GSSG.

Figure 25:
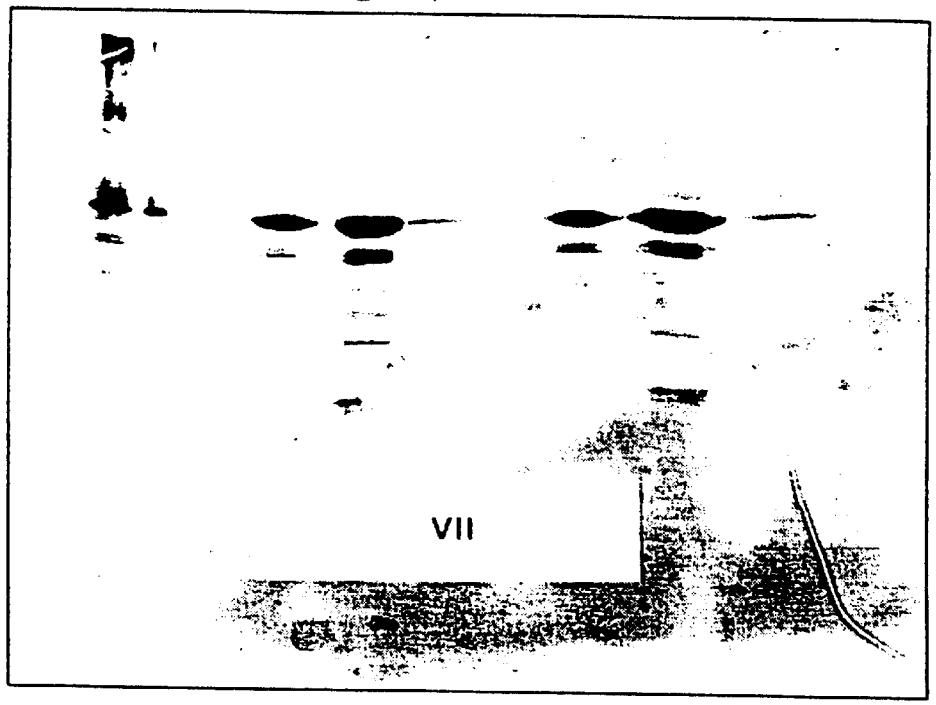
Figure 26:
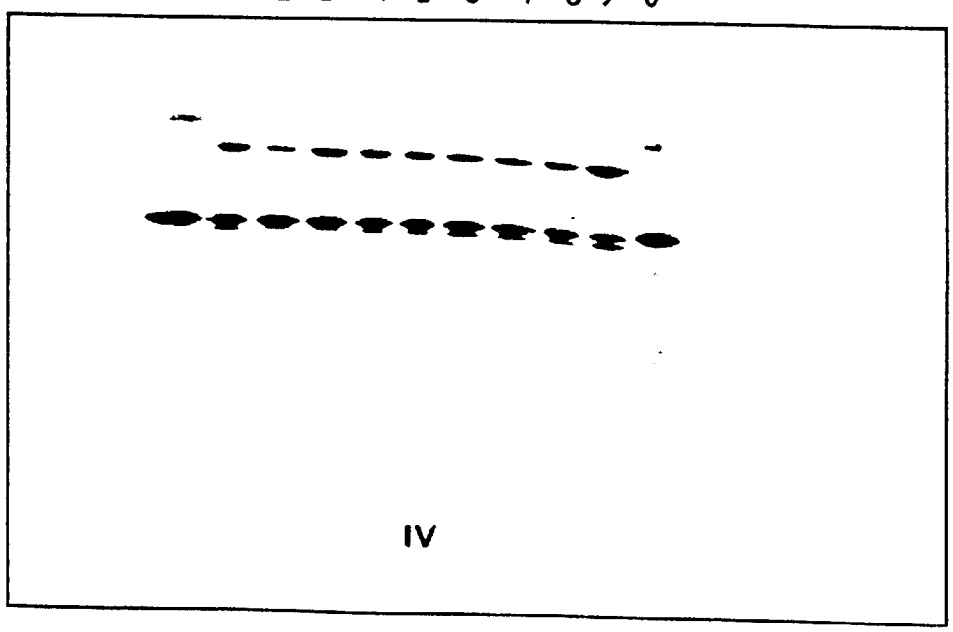

FIG. 25 (gel VII) shows a non-reducing SDS-PAGE gel of intracellularly expressed Mab32 diabody preparations from various stages of the purification.
1. Refolded protein
2. Refolded protein concentrated 50 fold
3. Final product after Superose 12 chromatography
4. Pellet spun down after the concentration step FIG. 26 (gel IV) shows a non-reducing SDS-PAGE gel of a intracellularly expressed Mab32 diabody preparation which has been cleaved with Factor Xa (to remove the his6 tag) for 20 h at 37° C. in the presence of 1 mM $Ni^{2+}$ at varying molar ratios of Factor Xa to diabody. Molar ratios of Factor Xa to diabody—track 1 1:5; track 2 1:2; track 3 1:1.

Figure 27:
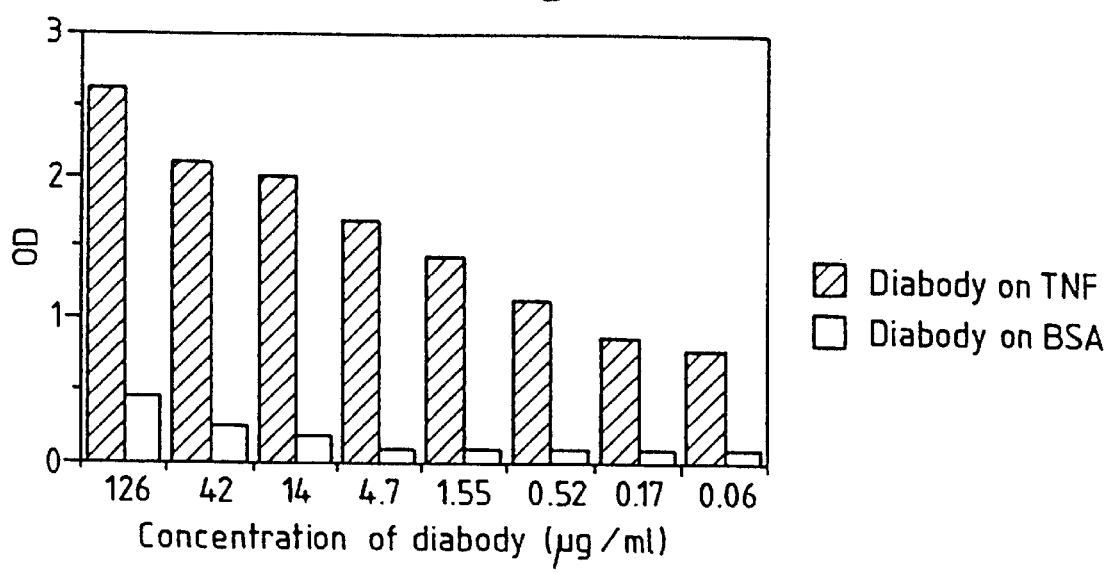

FIG. 27: Mab32 diabody bind specifically to human TNF. ELISA data of Mab32 diabody produced intracellularly and refolded to form a functional bivalent molecule. Binding to human TNF and BSA is assayed as described in the text.

Figure 28:
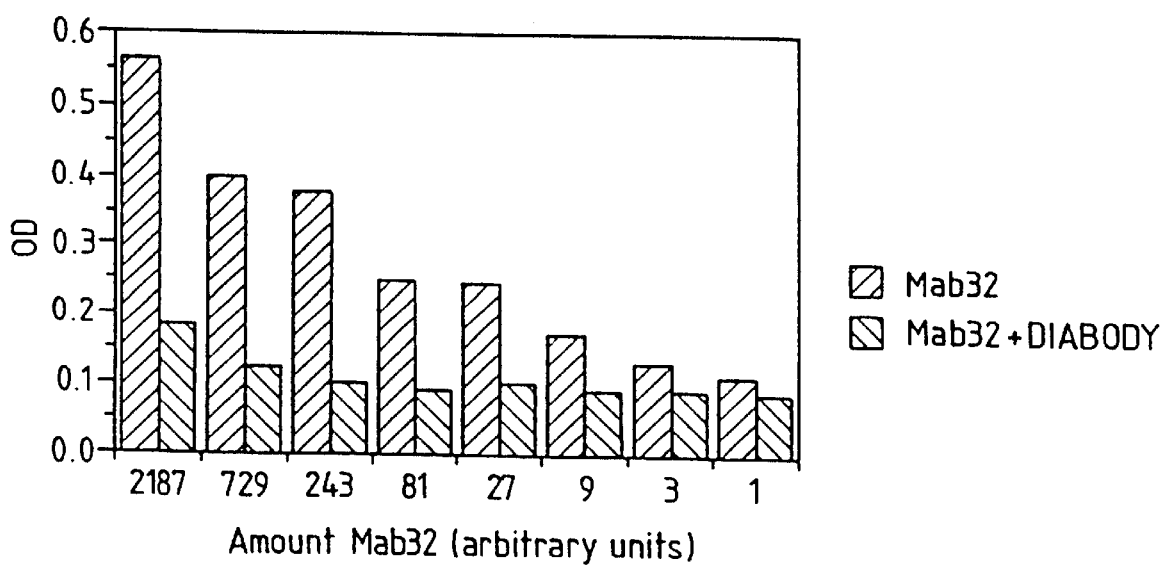

FIG. 28: Mab32 diabody competes with Mab32 whole antibody for binding to TNF. ELISA data of Mab32 diabody produced intracellularly and refolded to form a functional bivalent molecule. Binding to human TNF is assayed as described in the text.

FIG. 29: Anti-301 antiserum competes with binding of Mab32-diabody. ELISA data of Mab32 diabody produced intracellularly and refolded to form a functional bivalent molecule. Binding to human TNF is assayed in the presence of antiserum binding to a competing epitope as described in the text.

Figure 30:
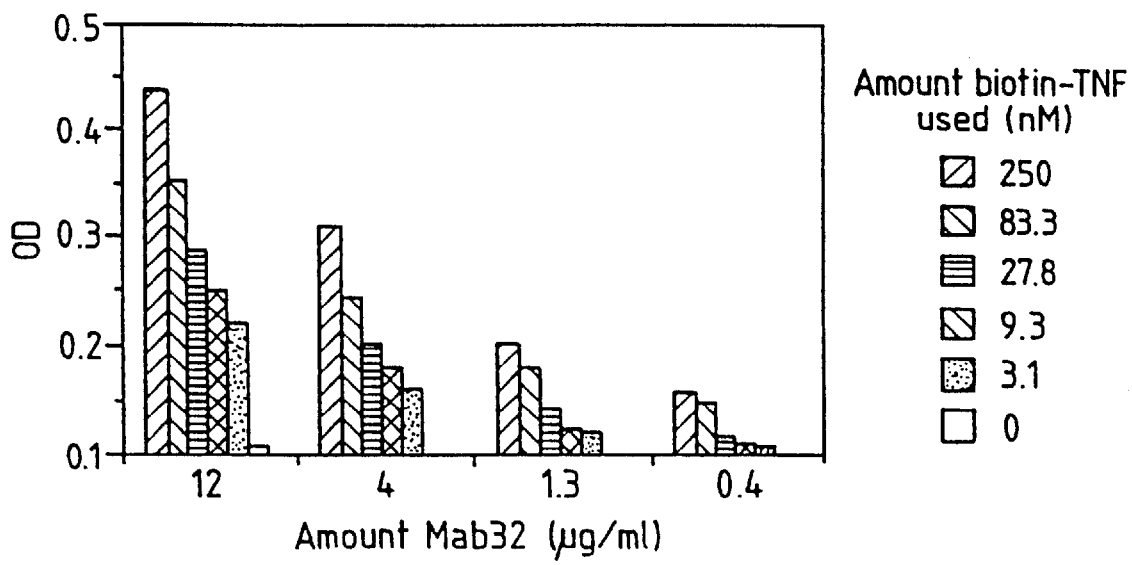

FIG. 30: Mab32 diabody is bivalent. ELISA data of Mab32 diabody produced intracellularly and refolded to form a functional bivalent molecule. Binding to human TNF is assayed as described in the text. Instead of detecting bound diabody by using the 9E10 antibody, biotinylated TNF is used, proving that the diabody is bivalent.

Figure 31:
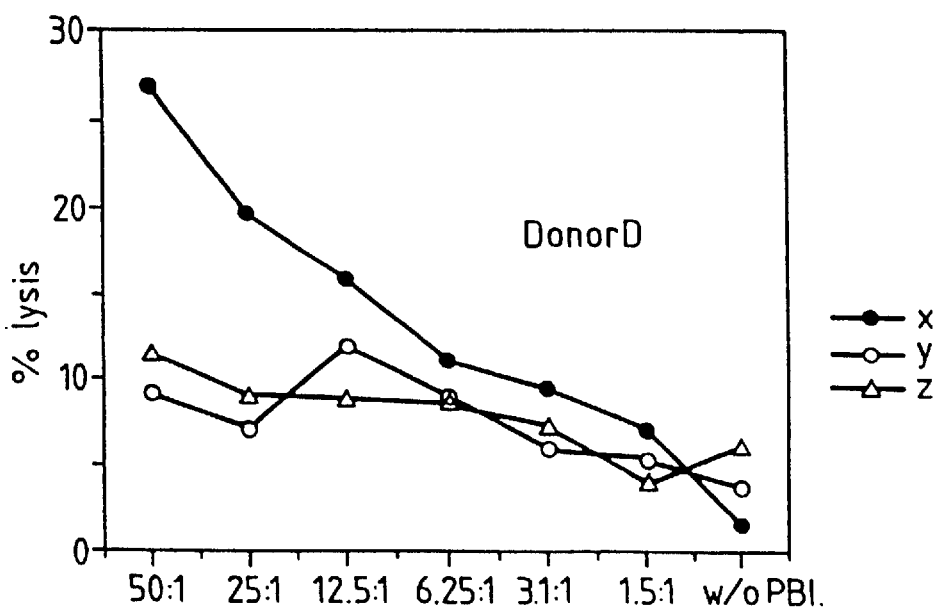

FIG. 31 shows CBM1 diabody mediated lysis of tumour cells by human PBLs. % lysis was determined using $^{51}Cr$ release. E:T ratio represents the ratio of effector cells (human PBL cells) to target tumour cells (LS174T). Human PBL were obtained from Donor D. CBM-1 was used at 1000 ng/ml and 10 ng/ml; w/o antibody is the data from the no antibody or diabody fragment control.

Figures 32, 32A:
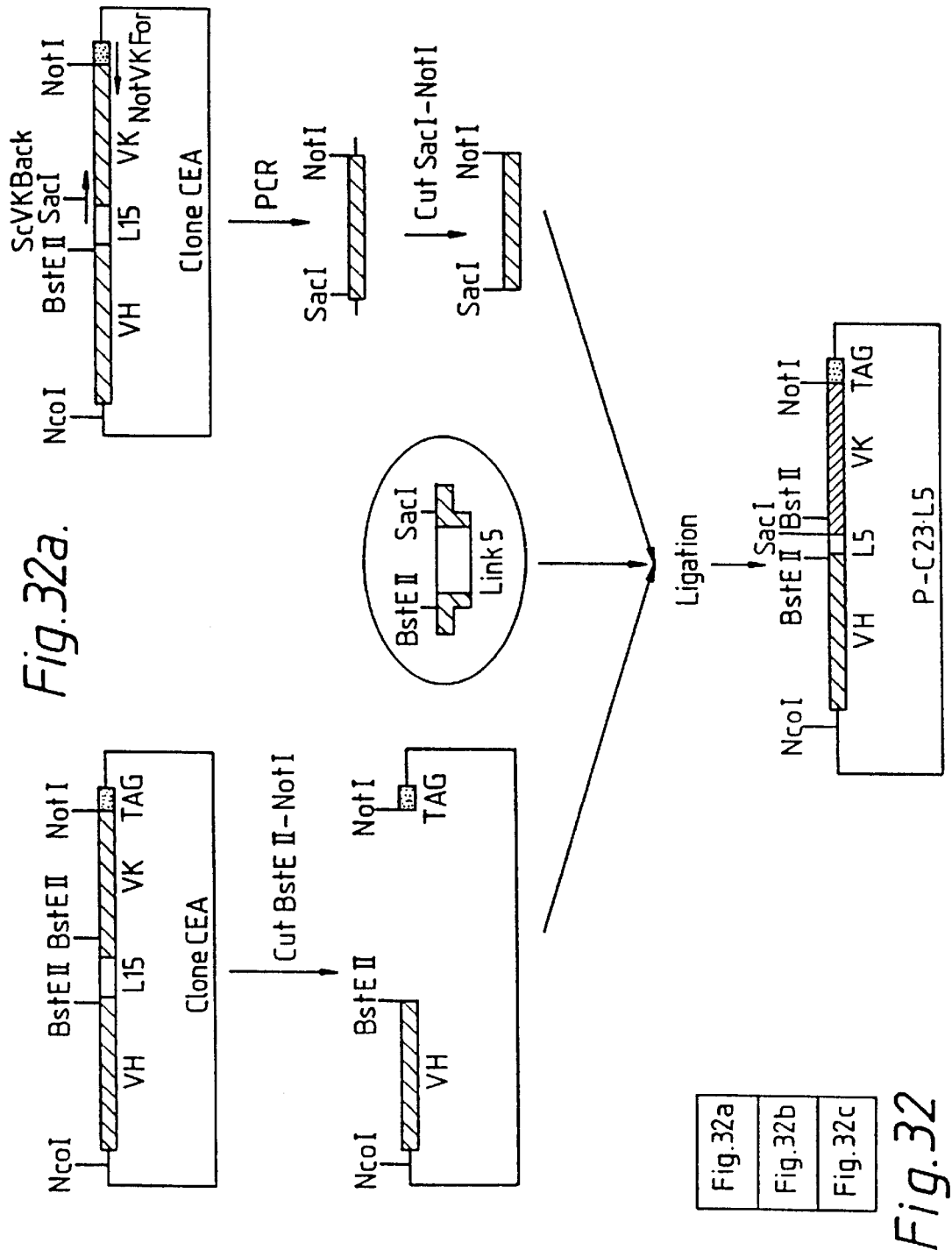
Figure 32B:
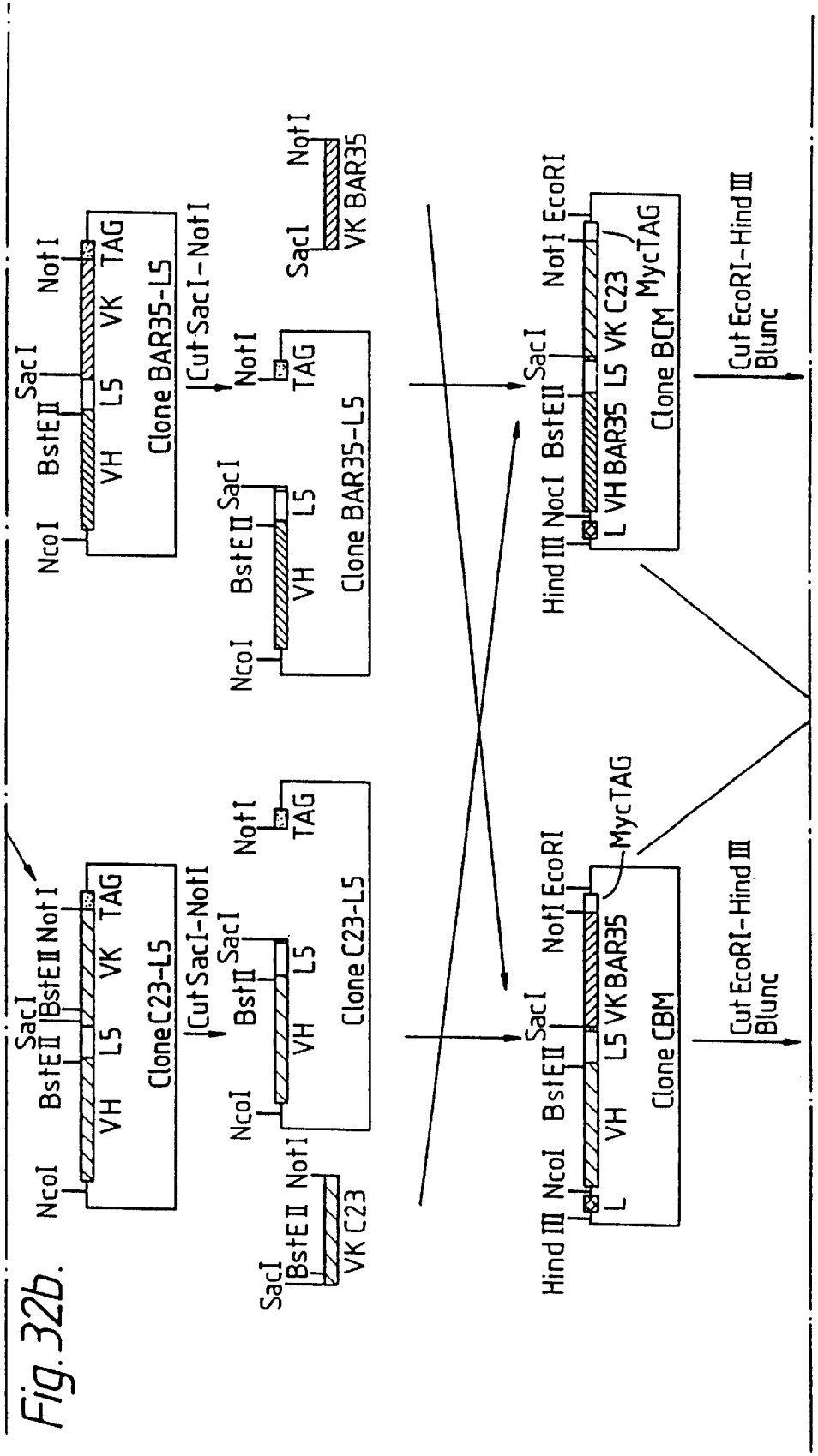
Figure 32C:
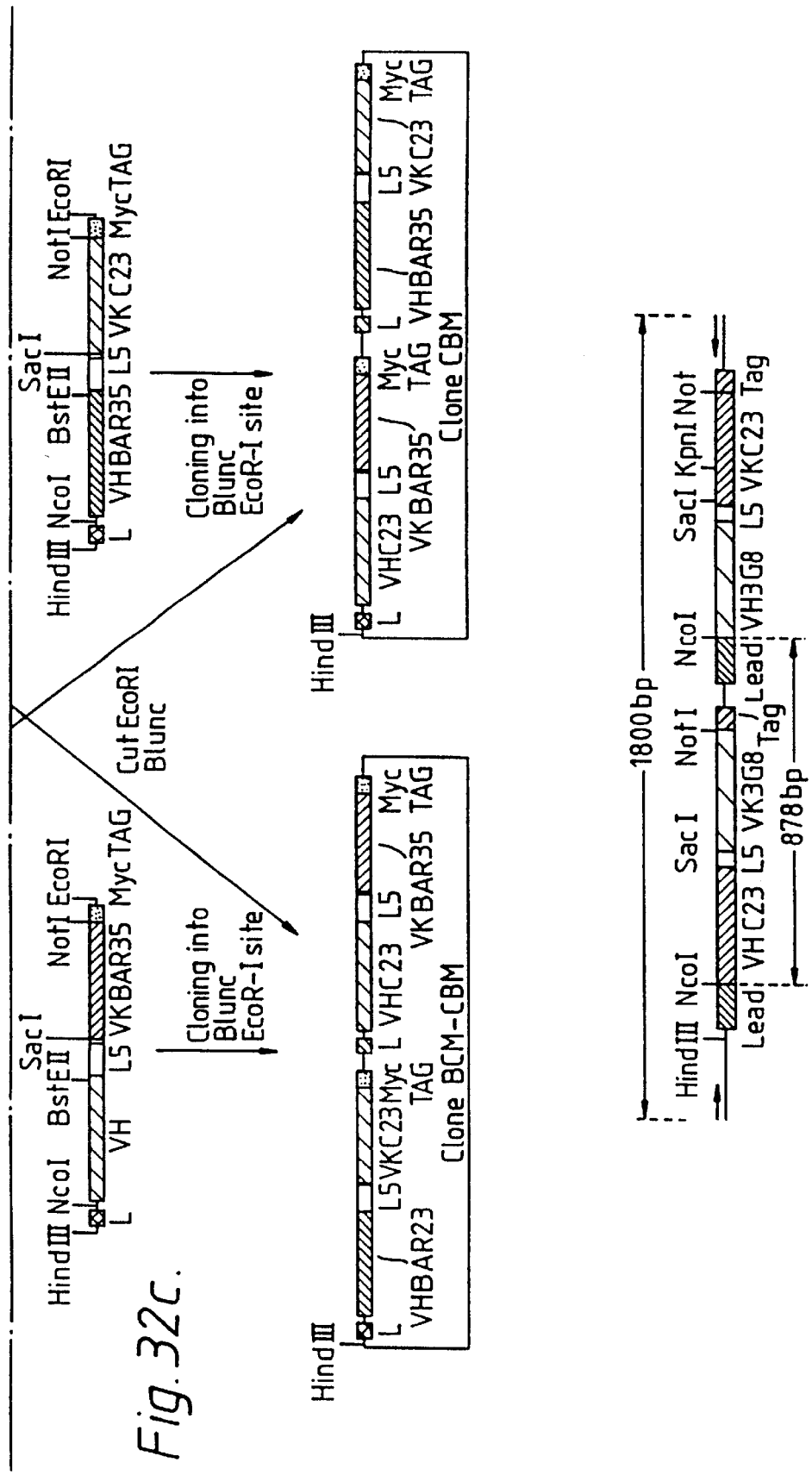

FIG. 32 shows the construction of the anti-CEA-anti-CD3 diabody CBM1. Clone CEA is the single chain Fv form of a murine anti-CEA antibody and BAR35-L5 is the 5 amino acid diabody version of monoclonal antibody 3G8. The diabody CBM-1 was constructed according to the scheme shown using the methods described in this application, FIG. 33: Construction of the bispecific diabody repertoire. The scFv repertoires enriched for phOx and Dig binders were used as starting point in the construction. E1-OX is ds-DNA from the scFv repertoire selected on phOx, supplying both heavy and light chain gene repertoires (VH-OX and VL-OX; see text for more details); E2-DIG is ds-DNA from the scFv repertoire selected on Dig, supplying both VH-DiG and VL-DIG gene repertoires (see text for more details). LN11 is ds-DNA of a phagemid vector containing Fab-D1.3, and is used as a supply for the region between the two VH-VL cassettes. Gene repertoires were amplified as indicated (see also text), and linked together in the bispecific diabody format by a combination of PCR assembly and ligation-mediated linkage and PCR. The final fragment was cloned as a Sfi-NotI restriction fragment into a phagemid vector for phage display.

Figure 34:
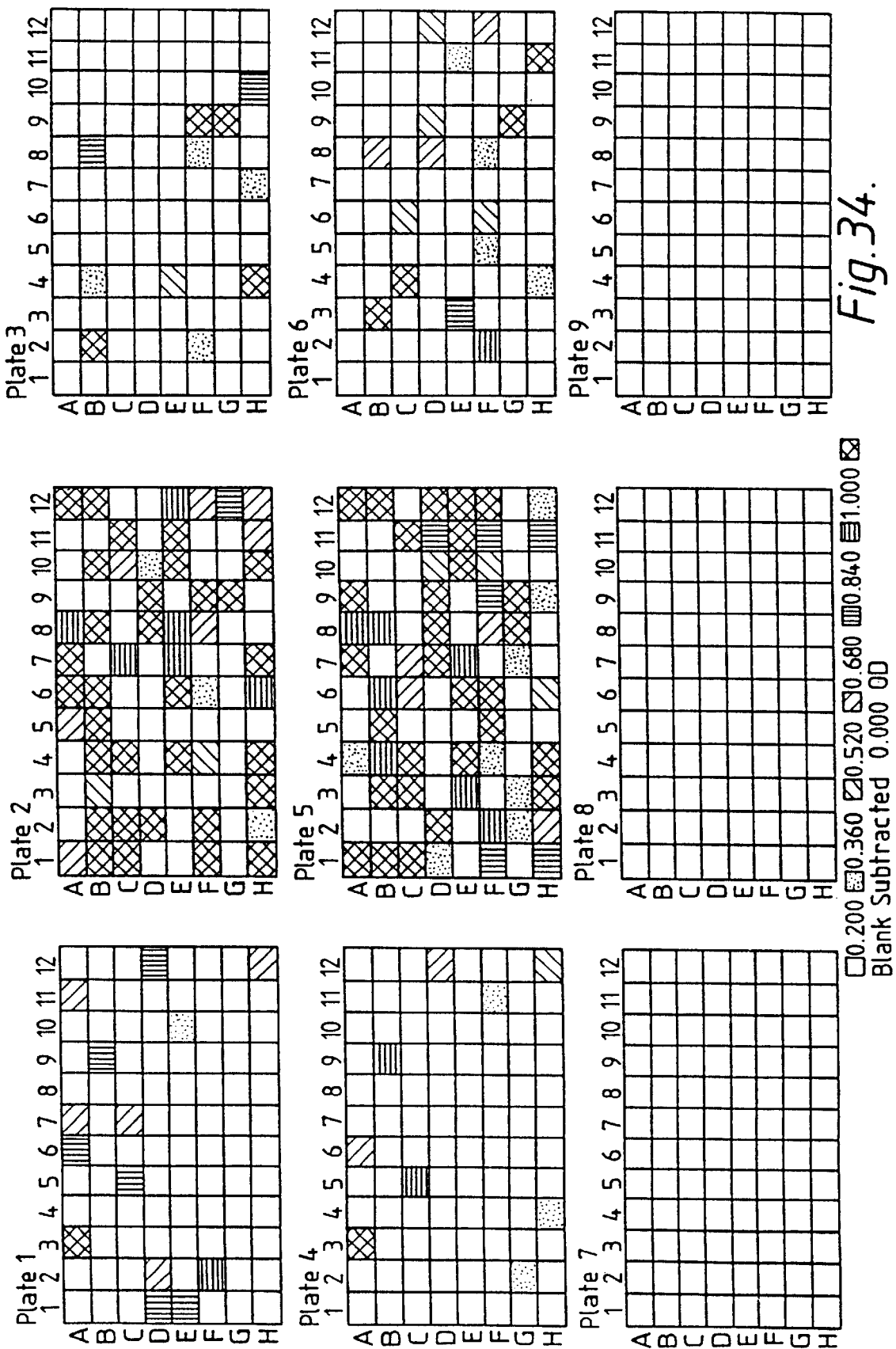

FIG. 34: ELISA Screening of clones from a bispecific diabody repertoire. Individual clones from the anti-phOx/anti-Dig bispecific repertoire were analysed before selection as phage diabodies (Plates 1, 4 and 7), and after selection on phOx-BSA as phage diabodies (Plates 2, 5 and 8) or soluble diabody fragments (Plates 3, 6 and 9). All Dig and phOx binding diabodies bound specifically to their antigen; bispecific clones were identified with a frequency of 6/93 before and 40/96 after selection. See text for further details.

FIG. 35: Binding of bispecific diabodies. Binding of bispecific diabodies form the repertoire selected on phOx-BSA, as phage (top) or as soluble diabodies (bottom) in ELISA. Relative binding to Dig-BSA or phOx-BSA varies from clone to clone, indicating that many different clones were obtained.

FIG. 36 shows ELISA assay signals for the binding of the NQ11 reverse diabody with zero residue linker and 2 residue linker to phOx-BSA

DETAILED DESCRIPTION

Bispecific and Bivalent Antibodies

Bivalent and bispecific antibodies have many practical applications, including use in immunodiagnosis and therapy (Winter G. and Milstein, C. (1991) *Nature* 349: 293–299; P. Holliger & G. Winter *Current Opinion in Biotechnology* 4: 446–449 1993). Bivalency can allow antibodies to bind to multimeric antigen with great avidity, bispecificity can allow the cross-linking of two antigens, for example in recruiting cytotoxic T-cells to mediate killing of a tumour cell (Staerz, U. D., Kanagawa, O. and Bevan, M. J. (1985) *Nature* 314: 628–631).

Preparation of bispecific antibodies has so far been complex and difficult. Bispecific diabodies can be utilised in the same applications as bispecific antibodies made by more traditional methodology. Diabodies however have the advantages of being smaller and being capable of being expressed in bacteria.

Preparation and Application of Bispecific and Bivalent Antibodies

Bispecific antibodies (bisAbs) have been made previously from two antibodies of different specificity by reduction and reoxidation of the hinge cysteines (as first shown for polyclonal antibodies) (Nisonoff et al., *Nature* 194: 355–358, 1962) or by fusion of the corresponding hybridomas (Milstein et al., *Nature* 305: 537–540, 1983). Unfortunately, this also scrambles the heavy and light chains, resulting in up to ten different antibody species, and the bisAb has to be isolated from this mixture. Alternatively, bisAbs have also been made previously by chemical coupling of two different antibodies. For example, two different IgG molecules (Karpovsky et al., *J. Exp. Med.* 160: 1686–1701, 1984; Brennan et al., 229: 81–83, 1985)), a Fab' fragment and an IgG molecule (Karpovsky et al., *J. Exp. Med.* 160: 1686–1701, 1984) or two different proteolytic Fab' or Fab'$_2$ fragments have been crosslinked using the hinge cysteines.

Bivalent antibodies have been prepared in bacteria as Fab'$_2$ fragments (WO93/06217). There have been limited reports of the expression of whole heterotetrameric bivalent antibodies in *E.coli* but the general utility of this system has yet to be shown (WO93/07896). Bispecific antibodies generated using this system would give a complex mixture of species.

Preparation of Engineered Bispecific Antibody Molecules

Engineered bisAbs have been assembled from Fv, Fab and single chain Fv antibody fragments (see FIG. 1) in vitro and in vivo. For therapy, antibody fragments should be more specific than IgG, as the Fc part of the IgG also targets Fc receptor bearing cells (Lanzaveccia, A. and Scheidegger, D. *Eur. J. Immunol.* 1987, 17: 105–111). Furthermore, smaller antibody fragments penetrate tissues more readily than IgG or Fab'2 fragments and are also cleared from serum more rapidly. These features may be desirable for targetting of radionuclides or toxins to tumours. Conversely, a longer serum half-life may be desirable for recruiting effector functions. Diabodies are the smallest bispecific antibody fragments yet made, which will assist their penetration of tumours. If it is required to make them larger, one may increase their size using fusion with CH3 domains, increasing the serum halflife.

Assembly of Bispecific Antibodies in Vitro

Carter et al. (*Biotechnology* 10: 163–167, 1992) have synthesized a bispecific Fab$_2$ linking by a disulphide bond a Fab fragment directed against human epidermal growth factor receptor 2 (p185$^{HER2}$) and a Fab fragment directed against CD3. This bisAb is able to mediate the killing of cells over expressing p185$^{HER2}$ by cytotoxic T cells.

Disulphide bonds can also be driven in vitro by oxidation using carboxy-terminal dimerization peptides to bring the Fab fragments together. Kostelny et al. (*J. Immunol.* 148: 1547–1553, 1992) used the Fos and Jun leucine zippers in this way. By mixing and dialysis in a redox buffer, heterodimeric Fab fragments (anti-CD3-Fos and anti-p55(IL-2R)-Jun) can be preferentially assembled, and the bisAb produced is capable of recruiting cytotoxic T-cells to lyse target cells bearing the IL-2 receptor (Kostelny et al., *J. Immunol.* 148: 1547–1553, 1992).

As provided by the present invention, and shown in example 1, bispecific diabodies can be assembled in vitro simply by mixing together two chains with 'crossover' pairings of variable domains.

Assembly of Bivalent and Bispecific Antibodies in Vivo

The secretion from mammalian cells (Neuberger et al., *Nature* 312: 604–608, 1984)) or bacteria (Skerra et al., *Protein Eng.* 4: 971–979, 1991)) of Fab' fragments with several hinge cysteines can lead to limited assembly of bivalent Fab'$_2$ fragments. Disulphide bond formation can be promoted using dimerization peptides. For example, scFv fragments engineered with a carboxy-terminal amphipathic helix and a single cysteine residue have been shown to form disulphide linked (bivalent) dimers on secretion from *E.coli* (Pack et al., *Biochemistry* 31: 1579–1584, 1992)). The use of amphipathic helices alone gives rise to an equilibrium between monomer and dimer; a disulfide bond is required to stabilise the dimer.

However, more stable dimerization domains can also be used without the requirement for disulphide bonds. For example, stable scFv homodimers can be dimerized through antibody CH3 domains and secreted from bacteria (P. Holliger & G. Winter, 1993 supra).

As an alternative to the use of dimerization peptides or domains, bisAbs can also be constructed by fusing two antibody fragments directly at the level of the gene. For example, two single-chain Fv fragments can be linked in tandem by a flexible polypeptide to make a bisAb for secretion from bacteria (P. Holliger & G. Winter, 1993 supra). On the other hand, presumably the four tandem domains can also form alternative (and incorrect) pairings within the same chain, or indeed with other chains.

P$^{11}$-A IS amino acid linker may be used in the generation of bispecific diabodies by cross-pairing of domains which are non-covalently associated in the formation N-(VHA-VIB-)C/N-(VAB-VLA)-C as is shown in Example 1. However, in this format the degree of dimerisation will be dependent on an equilibrium between the monomeric and chimeric scFv forms.

The use of short linkers to favour the pairing of variable VH and VL domains from different chains means that it is simple to make bispecific diabodies in the diabody format. The two chains of the diabody spontaneously assemble in vivo or in vitro. Although homodimers will be formed as well as the heterodimers which are bispecific, the homodimers will not form a functional antibody binding site. Selection is easy. For example, affinity chromatography using one of the two antigens of interest can be used to separate functional heterodimers with the correct pairing from the inactive homodimers.

Structure of Diabodies

Here, we describe the design of diabodies, usually small antibody fragments with two antigen binding sites.

The idea to construct diabodies was stimulated in part by our observation that scFv fragments secreted from bacteria were often present as both monomers and dimers (Griffiths, A. D., Malquist, M., Marks, J. D., Bye, J. M., Embleton, M. J., McCafferty, J., Baier, M., Holliger, P., Gorick, B., Hughes-Jones, N., Hoogenboom, H. R. and Winter, G. (1993) *EMBO J.* 12, 725–734, G. Winter, oral disclosure at Cardiff, September 1992); see also . . . Abstract from 8th International Congress of Immunology, August 1992. However, these single chain Fv dimers, appeared to consist of bivalent homodimers and the structure of these homodimers was not clear. In one embodiment of the present invention we provide a method of making heterodimers based on two different ScFv fragments. By linking the heavy and light chain V-domains of two different antibodies A and B to form two different "cross-over" chains N-(VHA-VLB)-C and N-(VHB-VLA)-C, we show that the chains recreate both antigen binding sites on association. The bispecific diabody can also be contructed with the "cross-over" chains N-(VLA-VHB)-C and N-(VLB-VHA)-C to recreate both antigen binding sites. We have termed this the "reverse" format. It is of particular interest that affinity of the antigen binding sites is retained, indicating that both binding sites are properly recreated. Furthermore the prepared heterodimeric fragments were mainly dimeric.

In another embodiment, the heavy and light chain variable domains are connected by a linker that does not allow pairing between the two domains on the same chain, e.g. because it is too short (in fact the domains may be connected directly), and the domains are therefore forced to pair with the complementary domains of another chain and create two antigen binding sites. As indicated by a computer graphic model of the dimers, the two pairs of domains can pack together with the antigen binding sites pointing in opposite directions. Bivalent dimeric diabodies can be generated using the short linkers, in addition to bispecific dimers. The VH domain may be N-terminal to the VL domain (VH-VL) or the VL domain may be N-terminal to the VH domain ("reverse"). In both cases the order of the VH and VL domains should most preferably be the same in both polypeptide chains.

Modelling of Diabody Molecules and Linker Lengths

Short linkers impose major constraints on the ways by which the two chains can associate. We therefore attempted to build a model of a dimer using the X-ray crystallographic structure of the FabD1.3 fragment in complex with the antigen HEL (Fischmann, T. O., Bentley, G. A., Bhat, T. N., Boulot, G., Mariuzza, R. A., Philipps, S. E. V., Tello, D. and Poljak, R J. (1991), J. Biol. Chem. 266: 12915–12920). Using the computer graphics programmed FRODO (Jones, T. A. (1982) in Computational Crystallography ed. Sayre, D. (Clarendon, Oxford, 1982) pp. 303–310) two molecules of the Fv portion were brought together such that the C-terminus of each VH domain was closely apposed to the N-terminus of each VL domain (with a C—N distance of about 7 Å), and easily satisfying the constraints of a 5 residue linker. The surfaces of the two VH domains could be docked together at the loops distal from the antigen binding site, without bad contacts as detected by eye and confirmed by the programmed PROLSQ (Hendrickson W. A. and Konnert, J. H. in "Structure, conformation and evolution" Vol I (ed. Srinivarsan, R.) pp43–57 (Pergamon, Oxford, 1981)).

The antigen binding sites point in opposite directions and the two sets of paired domains are related by a dyad axis (FIG. 12). Inspection of the crystallographic structures of other antibodies of the Brookhaven data base, indicates they should also be capable of packing in a similar manner (not shown). The packing of immunoglobulin domains across the dyad axis (tail to tail) differs from that in antibody or Ig superfamily structures, (see Jones, E. Y., Davis, J. D., Williams, A. F., Harlos, K. and Stuart, D. I. (1992) *Nature* 360: 232–239) for a recent comparison.

Inspection of the model suggested to us that it might be possible to join the C-terminus of the VH domain directly to the N-terminus of the VL domain, and dispense with the linker polypeptide,. Although this would be expected to result in slight clashes between the two VH domains as they pack together, we envisaged that the strain could be relieved by flexibility of the backbone in these regions, or by kinking the N-terminal β-strand of the VL domain. Indeed the fragment with no linker proved to be dimeric and bispecific (Example 1, Table 2), lending support to the proposed model. The binding affinity and dissociation kinetics of the fragment for phOx was altered, suggesting that the forced packing of the domains can lead to structural alterations at the antigen binding site, and that it indeed might be possible to build diabodies in which the antigen binding of the two binding sites is cooperative (or anti-cooperative). Cooperativity between the two antigen binding sites of a NQ11/B1.8 diabody is suggested in example 4 and is discussed further below.

The Examples given in this patent demonstrate that diabody molecules can be constructed for a wide variety of antibody variable domains with different antigen specificities. Many diabodies have been constructed with linker lengths of 0 or 5 amino acids and have been shown to be functional. These include bivalent diabodies directed against 2-phenyloxazol-5-one (phOx) (example 1); lysozyme (example 1); tumour necrosis factor (examples 5 and 7); V3 loop of HIV gp120 (example 4); carcinoembryonic antigen (CEA); Fc receptor FcγRIII (CD16); human Fc receptor FcγRI (example 17); surface Ig of BCL-1 lymphoma cell line (example 19) and the CD3 antigen (example 18). Bispoecific diabodies have been constructed directed against phOx and lysozyme (example 1); phOx and NIP (4-hydroxy-3-iodo-5-nitrophenylacetic acid) (example 3); CEA and CD16; NIP and FcRI (example 17); surface Ig of BCL-1 lymphoma cell line and CD3 (example 18); HIV gp120 V3 loop and human FcR1 (example 20) and phOx and oestriol (example 11). A number of these have been shown to bind markers on whole cells by FACS analysis including those directed against CEA; CD16 and CD3 (example 18).

Where one is seeking to convert a particular cloned antibody into a diabody format, it is a simple matter to vary the linker length (e.g. from 0 upwards) to see what works best. Likewise, substitution of different linkers, even of the same length, may be advantageous.

We also show in example 3 that the linker can be shortened to −1 with retention of antigen binding function. A series of minus linker molecules (making the linker shorter than zero to give (−1), (−2) and (−3) constructs by deletion of amino acids from the N-terminus of the VL domain or the C-terminus of the VH domain. Reduction of linker length further than −1 prevents folding of the NQ11/D1.3 diabody used in these studies. However, it remains a possibility that there will be examples of diabodies with different VH and VL domains where (−2) linkers will be functional.

As shown in example 1, whereas VH-VL polypeptides linked by a 15 amino acid linker are able to pair their VH and VL domains both as monomers and as dimers in the diabody format, VH-VL polypeptides with a 5 amino acid linker are only able to pair their VH and VL domains by forming dimers in the diabody format. We have not yet determined the maximum limit of length of the linker where the VH and VL domains can only pair in the diabody format (and not within a single polypeptide). However, experiments with a 10 amino acid linker suggest that the VH and VL domains can pair in a monomeric polypeptide (example 16).

The structure of diabodies is compact and with short linkers should be rigid. The lack of flexibility is unlikely to compromise the cross-linking of two soluble antigens, or of a cell surface antigen and a soluble antigen. We provide evidence in Example 13 that cross-linking of a tumour cell to a natural killer cell by a bispecific diabody can be achieved. In Examples 9 and 15 we demonstrate that bivalent and bispecific diabodies can be used to agglutinate antigen coated red blood cells. However, in some cases for cross-linking of two cells, some flexibility of the diabody molecule may be advantageous. Long linkers should allow greater flexibility for the diabody heads, but would also allow pairing within the same chain and formation of monomer fragments. Breaking one of the linkers entirely, as in the three chain fragment (FIG. 1), should give highly flexible heads, but it may prove more difficult to keep the three chains tightly associated. The construction and properties of this three chain fragment are described in example 1.

Although we modelled the dimer N-(VH-VL)-C with distance constraints of short linkers, it is also possible to model the dimer N-(VL-VH)-C much as in FIG. 12. except with the locations of the heavy and light chains interchanged, i.e. with the VL domain N-terminal to the VH domain. The N-(VL-VH)-C format of the diabody "reverse diabody" has been constructed and has been shown (example 15) to be expressed efficiently and to bind to antigen. By contrast we could not model as heterodimers the N-(VH-VL)-C with N-(VL-VH)-C or N-(VH-VH)-C and N-(VL-VL)-C given the constraints of short linkers.

For diabodies made up of two heterologous chains such as bispecific diabodies, it would be possible to prepare diabodies with asymmetric linkers, e.g. +1 on one chain, -1 on the other chain. Indeed, asymmetric diabodies with different combinations of lengths are possible, as exemplified by one chain having a linker of amino acids and one of O (see Examples). Only one of the polypeptides in a dimer need have its domains linked in a manner which prevents association of its domains.

Modification of the Packing Interface of Diabody Molecules

The model of the diabodies, discussed above, results in a packing interface between the two VH domains of the two Fv fragments in the N-(VH-VL)-C format diabody, or the two VL domains of the two Fv fragments of the N-(VL-VH)-C format diabody. (This contrasts with the packing of Fab fragments, in which the constant domains make limited interactions with the variable domains). It may be possible to introduce residues at the interface between the two Fv domains that could regulate activity, for instance by modifying cooperative properties.

Co-operativity

We demonstrate in this application that there can be anti-cooperative binding of antigen by the two sites of a diabody B1.8/NQ11 directed against 2-phenyloxazol-5-one and NIP, this suggesting that cooperative changes may be transferred from one domain to the other. The variable domains used were those of the parent antibodies B1.8 and NQ11. Although there are examples of conformation changes within individual VH/VL pairs in monomeric Fab fragments following binding of antigen (R. L. Stanfield et al. *Structure* 1 83–93, 1993; J. N. Herron et al. *Proteins* 11 159–175, 1991), this is the first time that cooperativity between two antigen binding sites of any antibody has been demonstrated. It may be possible to enhance (or diminish) the degree of cooperativity between the binding sites of a diabody by the introduction of specific amino acid residues.

Stability

The engineering of residues to introduce further non-covalent interactions across the interface, for example salt bridges, aromatic stacking, hydrogen bonds, or van der Waals contacts or covalent interactions through disulphide residues or glutaminyl lysine cross-links, should be capable of imparting extra stability to the diabody. The stability might be advantageous for the shelf half-life of the diabody, or its life in the serum, or in non-aqueous solvents. The interactions of the two chains of diabodies, with the two domains packing together as forced by the short linker, could presumably also be forced by enhanced packing interactions across the interface as defined by the model. In this case it may not be necessary to use a short linker to favour association of the chains in the diabody format rather than as single chain Fv fragments.

Residues at the Interface of the VH Domains to be Modified for Regulation of Cooperativity and Stability We have examined the model of the (VH-VL) D1.3 diabody and selected some residues for modification. The principal interaction between the two VH domains is formed by two loops of the VH. One of these loops is in framework 2, with residue 43 (a lysine in VHD1.3) of the two VH domains approaching within about 5 Å. The other loop is in framework 3, with the closest approach in the model being at residues 86 to 88 which approach closely residues 86 to 88 and residue 43 on the adjacent VH domain. These residues are therefore strong candidates for mutagenesis for modification to modulate stability and cooperativity. Example 22 gives examples where the interface has been modified with the aim of:
(i) introducing ionic bonds
(ii) introducing a disulphide bridge
(iii) increasing the number of hydrogen bonds
(iv) increasing the number of hydrophobic interactions
(v) increasing repulsive interactions Ionic bonds and hydrogen bonds have a strong directional element and are therefore dependent on the orientation of the residues involved.

The loops involved in the interaction between VH domains are normally in a polar environment in whole antibodies, single chain Fv and Fab fragments. It may therefore be energetically unfavourable for these residues to be in the interface between the VH domains in the diabody which may exclude water. Therefore the replacement of the polar residues with hydrophobic residues may make the packing of the diabody interface more rigid and stable.

There are analogous residues in similar positions in the two VL domains which would pack together in the case of the reverse diabody where modifications may be made in an analagous manner.

There may be other modifications which can be introduced. For example, the introduction of histidine residues at the interface or within the linker could allow changes in pH or metal ion concentration to alter the orientation of the domains with respect to each other, and to thereby regulate the affinity of binding.

The potential for cooperativity may also be adjusted for example by altering the linker length between the VH and VL domains. These can also be altered so that the linker lengths are asymmetric e.g. +1 on one chain, −1 on the other chain.

Use of Disulphide Bridges in Diabody Structure

Disulphide bridges can be used to covalently link regions within the diabody. For example, the two C termini of the CL domains of the VL-VH diabody can be linked by a disulphide bridge. In the model of the (VH-VL) D1.3 diabody, the C-termini of the VL domains are in close proximity, suggesting that these regions could be linked by a disulphide bond. Indeed when a Cys residue was inserted at the C-terminus of the VL domain of the bivalent fragment of NQ11 (5 residue linker) and the fragments were purified on phOx-BSA Sepharose as described, covalently linked dimers were noted, as determined by non-reducing SDS-PAGE and Western Blotting of the eluted fragments (example 23). This indicates that the disulfide linked chains are active in antigen binding, supporting over proposed model. This contrasts with the lack of success in driving the formation of intermolecular disulfide bonds between Fab fragments secreted from bacteria (Glockshuber, R., Malia, M., Pfitzinger, I. and Pluckthun, A. (1990) *Biochemistry* 29: 1362–1367).

Similarly, there may be potential for the introduction of a disulphide bridge at the C terminus of the VH domains of a reverse diabody.

Further as noted above a disulphide bond could be introduced across the interface between the VH domains of a (VH-VL) diabody.

It may be possible to favour diabody formation in a long e.g. 15 linker diabody by incorporation of cysteine residues at either end of the linker molecule. These cysteines may then form a disulphide bond giving the equivalent of a 2 residue linker with a peptide loop out. The formation of disulphide bridges at the C-terminus of the VL domain as above (example 23) and in diabodies containing metallothionein (example 25) suggests that this approach may be feasible.

Modification of the Interface of Paired VH/VL Domains

When antigen binds to an antibody, there may be in some cases a shift in conformation. The degree of transmission of this conformation change, within and between the VH/VL pairs of the diabody, will depend on the degree of interaction between the VH and VL domains.

There may also be modifications which can be made which will enhance the cooperativity of the diabody molecule. There are a number of residues at the interface of the VH and VL domains which interact with each other and have the potential to be modified to adjust the ease with which the VH and VL domains move with respect to each other. The modification of these residues may enhance the possibility of cooperativity between the two antigen binding sites of the diabody.

Fusions with CH3 Domain

Each diabody is about the same size as a Fab fragment. It may be advantageous to increase the size, for example for enhanced retention in the serum, The diabody could therefore be genetically fused to other proteins, or other antibody domains, for example through an antibody CH3 domain to give VH-VL-CH3 homo and heterodimeric chains (as described in example 12).

Diabody Dimers

The diabodies could also be linked as diabody-dimers, that is with four VH-VL chains by chemical crosslinking. This would be equivalent in size to a $(Fab)_2$ fragment. For example, introducing a C-terminal cysteine residue at the C-terminus of the VL domains (for the VH-VL dimers) would allow diabody-dimers to be made through disulphide bonds (P. Carter et al. *Biotechnology* 10: 163–167, 1992) or thioether linkages (M. J. Glennie et al. *J. Immunol.* 139: 2367–2375 1987). This gives the possibilities of making $(Fab)_2$ like fragments with four binding specificities, or two binding specificities (but two binding sites for each), or a single binding specificity (but four copies of each). Such diabody-dimers could have enhanced avidity of binding compared with $(Fab)_2$ fragments.

Multimers of More than Two Polypeptides

Trimer and tetramers have also been observed in a purified bivalent diabody preparation (D1.3, 5 residue linker) (Fisch, I., Holliger, P. and Winter, G. unpublished results) indicating that short linkers are compatible with the formation of multimers.

Bi- or trispecific Fabγ3 molecules have been constructed from Fab' fragments by in vitro coupling of the hinge free cysteines but our observations indicate that small trispecific antibody fragments that assemble in vivo may be made in a way analogous to the design of diabodies. By linking the heavy and light chain V-domains of three different antibodies A, B and C to form two different chains VHA-VLB, VHB-VLC and VHC-VLA, the chains may recreate three different antigen binding sites on association.

One should choose antibodies for which the VH and VL domains are known to associate and form a stable Fv fragment in analogy to the diabody design using short linkers (5 residues) to prevent the VH and VL domains on the same chain from pairing with each other.

Modelling

We attempted to build a model of a trimer using the X-ray crystallographic structure of the Fab fragment of the D1.3 antibody in complex with the antigen HEL (Fischmann et al. supra). Using the computer graphics programme FRODO (Jones et al. supra), three molecules of the Fv portion were brought together such that the C-terminus of each VH domain was closely apposed to the N-terminus of a VL domain, and easily satisfying the constraints of a 5 residue linker. In contrast to the diabody model (see above) the three antigen binding sites in the triabody are located on the same face of the molecule and are related by a tryad axis.

The C-termini of the VL domains are all located on the opposite face of the molecule and distant from each other. By introduction of a cysteine at the C-terminus, two triabodies might be crosslinked to form a hexavalent molecule of approximately the same molecular weight as an IgG.

The distance between the C-termini makes it unlikely that intramolecular disulfide bonds could be formed in a similar way as for diabodies.

The structure of triabodies seems to be less compact and more flexible than the structure of diabodies. Indeed it seems possible that the binding sites could flip-flop between the two faces of the molecule. A possible conformation of the triabody molecule is planar with the three binding sites located in a plane at an angle of 120° from each other.

The centre of the molecule contains a hole. Crosslinks (eg, disulfide bonds, metal binding sites) at the interfaces or the central hole of the molecule, could be used to increase stability and make more rigid fragments. A tight linkage between the three Fv domains may make it be possible to build triabodies in which the antigen binding of the three binding sites is cooperative (or anti-cooperative).

In analogy to the bispecific three chain diabody construct (VII, see above), a four chain triabody construct can be imagined where e.g. three soluble domains: VHA, VLB and VHC assemble with the VLA-VHB-VLC domains encoded on one polypeptide chain (other combinations are possible as well). Such constructs may however be limited by the tendency of some Fv fragments to dissociate upon dilution.

Applications

In discussion herein of applications and utilities of the molecules provided by the present invention, general reference to "diabodies", whether bivalent or bispecific, should be taken as including multimers such as the trimeric "triabodies" and so on, where appropriate and mutatis mutandis.

Recruitment of Effector Functions and Treatment of Tumour Cells

Bispecific antibodies have found particular use in recruiting the powerful effector functions of cytotoxic T cells or natural killer (NK) cells. Thus bisAbs have been used to bridge the T cell coreceptor (CD3) (Staerz et al., *Nature* 314: 628–631, 1985) or FcRIII (CD16) (De Palazzo et al., *Cell Immunol*. 142: 338–347, 1992) and the cell surface antigen of a target cell to mediate the killing of target cells by cytotoxic T cells or NK cells. In mice, such anti-CD3 bisAbs can inhibit the growth of solid tumours (Titus et al., *J. Immunol*. 138: 4018–4022, 1987, Garrido et al., *Cancer Res.* 50: 4227–4232, 1990) or even eradicate lymphoma (Brissinck et al., *J. Immunol* 147: 4019–4026, 1991); in humans, they have been used against malignant glioma (Brissinck et al., *J. Immunol*. 147: 4019–4026, 1991). Bispecific antibodies have also been used for ex vivo purging of leukaemia cells from bone marrow (T. Kaneko et al., *Blood* 81: 1333–1341, 1993).

Bispecific antibodies synthesized in vitro have also been used to deliver enzymes, antigens, toxins, radionuclides and cytotoxic drugs to tumour cells (see 12–14; M. A. Bonardi et al., *Cancer Res*. 53:187–199 1992).

Imaging of Tumours

Bispecific anti-tumour marker, anti-hapten antibodies have been used to image tumours (J. M. Le Doussal et al. *Int. J. Cancer Supplement* 7: 58–62, 1992; P. Peltier et al. *J. Nucl. Med*. 34: 1267–1273 1993; C. Somasundaram et al. *Cancer Immunol. Immunother*. 36: 337–345, 1993; A. Bruynck et al. *Br. J. Cancer* 67: 436–440, 1993). First, the antibody is injected and localises to the tumour by binding to the tumour marker. A radioactively labelled hapten, for instance a metal chelate with $^{99}$Tc or $^{111}$In is then injected which preferentially localises to the tumour, by binding to the bispecific antibody, enabling imaging of the tumour. Similarly, diabodies with one arm specific for tumour cells and one arm specific for metal chelates could be used to deliver chelates of radioactive metal ions such as $^{99}$Y for therapy of cancer.

Other Applications

Bispecific antibodies have been utilized to attain a number of experimental objectives that extend beyond the targetting of tumour cells; Thrombolysis has been enhanced by targetting tissue plasminogen activator to blood clots: Growth of human immunodeficiency virus (HIV)-1 in cell culture has been inhibited by directing the virus to the Fc receptor (rather than their normal receptor, CD4): A non-permissive human cell line has been infected by a mouse retrovirus through linkage of the virus to the major histocompatibility complex (MHC) class I and II cell-surface proteins. BisAbs have been found to act as an adjuvant when used to crosslink antigen to antigen-presenting cells.

An anti-FcgRIII anti-dengue virus bisAb has been used to enhance virus infectivity (B. J. Mady et al. *J. Gen. Virol*. 74: 839–844, 1993) by bringing the viruses in close conjunction with the cell to be infected.

Some Utilities of Diabodies

Although bispecific antibodies appear to have great potential in the therapy of cancer and other diseases, difficulties in their production and purification have limited their application. Their use has tended to be limited to difficult therapeutic problems where the amount of effort involved in preparing bispecific fragments is worthwhile. The diabodies described in this invention greatly simplify the process of preparing bispecific antibodies and this will greatly expand the range of applications to which they can be put.

Bispecific diabodies could be used for virtually any application for which bispecific antibodies have been used as described above, for example, with one arm of the diabody to trigger effector functions and the other arm for targetting of cells, virus or bacteria. For triggering effector functions, one arm could be directed against human IgG receptors (FcγRI, FcγRII, and FcγRIII) or IgE receptors (FcεRI and FcεRII). For the high affinity FcγRI receptor, the fragments should be directed towards an epitope that is not blocked by the Fc portion of IgG. Diabodies could also bind to human T-cell antigens such as CD3, although it will be necessary to activate T-cells to elicit killing. The effector arm could also be provided by binding of radioactive isotopes, for example radioactive metal ions in complex with a chelate, or radio-iodinated haptens; or by binding to an enzyme capable of cleaving a prodrug.

The bivalent (and bispecific) diabodies could also be used for coagulation of cells, bacteria or viruses, by making multiple interactions, as with diagnostic assays of agglutination of red blood cells. Bispecific diabodies could also be used for bridging between different particles, for example to target retrovirus to cells for gene targetting for introduction of genetic material into specific cells. The diabodies may also bind simultaneously to two epitopes on the same surface, for example a viral coat, so as to bind with high avidity and to block the uncoating of the virus; or by cross-linking the CD3 antigen so as to activate T-cells. Agglutination of antigen coated red blood cells by bivalent and bispecific diabodies as described in Examples 9 and 15 suggest that these approaches are feasible. This is supported by cytolysis of tumour cells in Example 13. A diabody could be used with specificity for two chains of the same receptor, for instance the α and β chains of the IL2-receptor. Bispecific diabodies directed against two different epitopes on the same polypeptide chain may give extra specificity and avidity of binding to that chain. Diabodies could also be used in making the matrix for affinity chromatography of antigens, by providing one binding site directed against a component of the matrix, and the other against the antigen of interest. This principle could be extended to the immobilisation of antibodies on surfaces such as the chips used in detection binding studies with surface plasmon resonance, or using evanescent wave detection. One specificity could be directed against the matrix on the chip surface whereas the other arm will be directed out from the chip surface to allow binding studies with antigen to be performed.

It may be possible to adapt the use of retroviruses for the display of antibody fragments (S. J. Russell, R. E. Hawkins and G. Winter Nucleic Acids Res. 21: 1081–1085 1985) to the display of diabodies. For instance the retrovirus could display a bivalent diabody for the increase of avidity for binding of a tumour cell.

Diabodies may be used to deliver cytotoxic drugs to tumour cells, using one binding site to deliver the drug and the other to bind to the tumour, or using systems analogous to that described for the delivery of doxorubicin to tumours by P. A. Trail et al. (*Science* 261: 212–215, 1993). These authors used an antibody directed to the Lewis Y antigen, covalently linked to doxorubicin, which was internalised into lysosomes and endosomes. The linkage was cleavable in these environments leading to delivery of the drug to these cells. Bivalent diabodies may be particularly useful to increase the avidity of the antibody for the tumour cell. The specificity may be increased by using a bispecific antibody directed against two different markers.

It may be possible to deliver diabodies across the blood brain barrier using bispecific diabodies with one arm directed against either FHA, an adhesin of the bacterium *Bordetella pertussis* or against the natural ligand for the leucocyte adhesion molecule CR3 (E. I Tuomanen et al. *Proc. Natl. Acad. Sci. USA* 90: 7824–7828, 1993) and the other arm may then be directed against a target to provide the therapeutic function.

For imaging of tumours, it may be possible to label by introducing a metal ion which is chelated and in which the chelate binds to one binding site or by an additional peptide which is incorporated either as part of a linker between VH and VL domains or as an extension.

Bivalent antibodies may be particularly useful for imaging purposes for instance when localising tumours by binding to a tumour antigen with a $^{125}$I-labelled antibody. The presence of two binding sites for antigen would give an avidity component which may increase the signal from the tumour compared to the background. Bispecificity against two markers on the surface of the tumour cell may also help to increase tumour specific imaging signal compared to background. It may also be advantageous to use bispecific antibodies with one arm directed against a tumour cell surface marker and another against an antigen which is shed from tumour cells, but is found in high concentration in the vicinity of tumour cells.

Diabodies may be used in retargetting of antibodies to a site or antigen for which they have no specificity under normal circumstances. The diabody would possess two specificities; one specificity for the target site, the other capable of binding to selected parts of an antibody molecule. In this manner, antibodies with no specificity for the antigen target are brought into proximity with the antigen via the diabody. This principle is advantageous for re-targeting antibodies in the circulation to sites within the body such as tumours and to block inappropriate immune responses exemplified by autoimmune disease and would allow recruitment of effector functions.

In this way, diabodies could be used to recruit effector functions through binding to whole antibody chains. One arm would be directed against antigen for therapy and the second arm against whole antibodies for the recruitment of effector functions (see example 21). Whereas the V-domains (and fragments containing V-domains) are largely responsible for interacting with antigen, the C-domains recruit effector functions. The type of effector function recruited is largely governed by the class of C-domain (the isotype). For example, C-domains of the IgG1 (γ1) isotype can kill cells by triggering the complement cascade at the cell surface, resulting in lysis and can also bind C-domain receptors (Fc receptors) on specialised phagocytic and killer cells. In contrast, antibodies of the IgG4 isotype (γ4) appear to actively prevent recruitment of effector functions and thereby block an immune response.

The format of the diabody, in which the two antigen binding sites are linked closely together, offers other possibilities distinct from a bispecific antibody, or other bispecific antibody fragments produced in bacteria. Packing of the two binding sites together may lead to enhanced affinity; and binding of antigen at one binding site may lead to enhanced or reduced binding at the other. This feature could be desirable in allowing the construction of a "conditional" switch, for turning on or off an activity in response to a signal, as illustrated by:

(1) homogeneous assays, with diabodies against an analyte and an enzyme. Thus binding to analyte at one end could trigger the release of the enzyme at the other end. If the activity of the enzyme were inhibited by binding of the diabody, its release would cause an increase in the activity of the enzyme that could be detected by a coloured or fluorescent substrate. Alternatively, the other end of the diabody could release a prosthetic group, required for activity of an apo-enzyme. Conversely, the diabody might be triggered by binding of analyte to bind to an enzyme and thereby turn on its activity.

(2) prodrug activation, similar to homogeneous assays as above. Diabody could be made in which binding of tumour cell markers would lead to activation of the other end for binding to an enzyme. (This could be an advantage over simple bispecific diabodies in that only the cell surface bound antibody would bind to enzyme). Other features could also be introduced, for example that binding of the diabody to the enzyme triggered its catalytic activity.

Selection of Allosteric Antibodies

Allosteric antibodies could be isolated from bispecific repertoires by selection. Such allosteric antibodies could be selected by binding to a first antigen and eluted by adding the second antigen. This would select those in which the affinity of binding at the first site is reduced by occupancy of the second site. Likewise, selection may be by virtue of improved interaction with the firs antigen on addition of the second antigen.

Formats for Agglutination using Diabodies

As noted earlier, bivalent and bispecific diabodies could be used for coagulation of cells, bacteria or virus, by making multiple interactions, as with diagnostic assays of agglutination of red blood cells. For antigens which are well exposed above the surface of the cell, for example blood cell group B antigen, it is possible to agglutinate the cells directly using a single diabody molecule. However, to agglutinate using antigens which are not well exposed or to improve the general efficiency of agglutination, it would be desirable to increase the span of the crosslinking molecules. There are a number of formats which can allow this to be done with diabodies, including the following.

(i) Two linking diabody molecules: for instance the two antibodies used might be:
   Diabody 1—with one specificity directed against a blood cell surface antigen (Site 1) and the other specificity directed against an antigen not normally present in blood, so that this binding site (Site 2) is free.
   Diabody 2—with one specificity being anti-idiotypic directed against Site 2 on the first diabody (Site Anti-2) and the other specificity directed against the blood cell surface antigen (Site 1).
   This format will allow agglutination of blood cells with the distance spanned being the length of two diabody molecules as shown in FIG. 2.
(ii) Three linking diabody molecules: for instance the molecules used in the linking might be:
   Diabody 1—with one specificity directed against a blood cell surface antigen (Site 1) and the other specificity directed against an antigen not normally resent in blood, so that this binding site (Site 2) is free.
   Diabody 2—with both specificities being anti-idiotypic directed against Site 2 on the first diabody (Site Anti-2). In this format when two molecules of diabody 1 bind to different red blood cells diabody 2 can bind to each of these diabody 1 molecules at Site 2 thus forming a complex of three diabody molecules spanning the distance between the two red blood cells as shown in FIG. 3.
(iii) Two diabody molecules and one non-diabody molecule making link: for instance the molecules used in the linking might be:
   Diabody 1—with one specificity directed against a blood cell surface antigen (Site 1) and the other specificity directed against another non-diabody antigen which is to be added to the assay (Site 2)
   Non-diabody antigen molecule- this would be a large molecule to which Site 2 of diabody 1 is directed. The preferred molecule would have multiple identical epitopes, for instance a multimer such as *E.coli* beta-galactosidase, a tetramer of 200 kD subunits, could be the antigen. An alternative would be to use a large molecule multiply derivatized with a hapten for instance thyroglobulin derivatized with 2-phenyloxazol-5-one and for Site 2 of diabody 1 to be directed against 2-phenyloxazol-5-one. It may be preferable for the non-diabody antigen molecule to be a molecule that is not normally found in blood such as this hapten. In this format two molecules of diabody 1 bind to two different cells. The non-diabody molecule will bind to both diabody molecules through Site 2 crosslinking the red blood cells (FIG. 4).
   A variety of different large molecules could be used for this agglutination, for example the second site of diabody 1 could be directed against the C$\mu$ region of IgM, perhaps from a different species than the cells being agglutinated.
   It would be possible to use this same format but with a diabody 2 which binds through Site 1 with the blood cell surface antigen but binds through its second site with a different epitope on the non-diabody antigen molecule generating a crosslinked complex with a similar geometry.
   Protein A could be used as a link between the two diabody molecules. Protein A binds to the framework regions of V domains of the human VH3 family and to certain V domains of the VH1 family and would crosslink diabodies derived from these families.
(iv) Using a whole organism in the crosslinking reaction
   In the above cases the linking molecule for agglutination is a protein molecule. The principle can be extended to the use of organisms to crosslink such as bacteriophage M13 or bacteria such as *E.coli*.
   In format (iii) above, Site 1 of diabody 1 could be directed against a cell surface marker and Site 2 directed against a bacteriophage surface molecule such as the gene 8 protein (FIG. 5).
   Such diabodies can be constructed from previously isolated antibodies raised against, for example a cell surface marker and gene 8 protein. It would however be possible to select such antibodies using phage display methodology. A diabody could be expressed as a soluble fragment encoded within the phage genome with specificities against both the cell surface marker and the gene 8 protein. This diabody would then be displayed on the surface of phage. An alternative would be to incorporate a peptide tag sequence such as the c-myc tag into the gene 8 protein and have the second specificity of the diabody directed against the tag to allow its display on the phage surface. In these formats antibodies to the cell surface suitable for agglutination could be directly selected from phage display libraries in which one VH/VL pair is derived from a variable domain repertoire and the other VH/VL pair allows binding to gene 8 protein or a tag. Gene 3 protein could be used as an alternative to gene 8 protein.
(v) Agglutination as a method of assaying soluble antigen
   Formats such as those described in (iii) above could be used alternatively in procedures to measure soluble antigen. In this case cells with a known cell surface marker would be used as a reagent and the degree of agglutination would be dependent on the amount of soluble antigen present.
   This principle could be extended to the assay of haptens by the use of diabodies with sites which the recognise antibodies with the hapten bound. In this format there would be two diabodies:
   Diabody 1 with site 1 recognising a cell surface marker and site 2 recognising the hapten.
   Diabody 2 with site 1 recognising a cell surface marker and the second site recognising diabody 1 with the hapten bound.
   These methods of measuring soluble antigen would not be confined to using cells to which diabodies are directed but could instead use any format suitable for agglutination, for example latex beads.

Trimers

Trivalent or trispecific triabodies may have advantages over diabodies or other bispecific antibody fragments in a number of applications:
   The higher flexibility and the three binding sites pointing to one face may make trivalent triabodies ideal to bind with great avidity to surfaces displaying repeated epitopes (analogous to IgM). The three fold symmetry may be of particular advantage in binding to viruses as it mimicks the three fold symmetry common in many viral coat proteins.
   Triabodies could bind three different or identical epitopes on the same soluble molecule (e.g. protein or protein assembly, biologically active peptide etc.) leading to a very high affinity and specificity useful for diagnostic and therapeutic purposes. (In organic chemistry this effect is exploited in molecules named chelators, cryptants or crown ethers that bind their ligands with exquisite specificity and affinity.)
   Effector functions (cytotoxic T-cells through CD3 or CD16, macrophages and granulocytes through FcR) could be recruited more effectively through triabodies:
   (1) Unprimed T-cells can be activated through bridging of two CD3 molecules on the T-cell surface (Tutt91) or crosslinking of CD3 with CD28 (Jung91).

(2) Increased cytotoxicity by targeting a cytotoxic cell and an activating cytokine (IL-1, IL-2, IFNγ, TNFα, GM-SF etc.) to the same cell.

(3) two copies of the same or one copy of two different effectors (e.g. toxins, radionucleotides, prodrug convcerting enzymes, complement components etc.) could be targeted.

(4) A higher specificity could be achieved by recognizing two different markers or by avidity binding two identical markers on the target cell surface. Crosslinking of two markers on the target cell should also promote endocytosis which is beneficial when targeting e.g. toxins or retroviruses for gene therapy.

(5) two different sets of cytotoxic cells (killer T-cells, NK cells, macrophages etc.) could be recruited to the same target.

Construction of Diabody Repertoires and their Display on Bacteriophage

The display of bivalent and bispecific diabodies on phage allows the power of selection with antigen of antibodies on phage (WO92/01047; J. McCafferty et al., 1990 supra; H. R. Hoogenboom et al., *Immunol. Rev.* 130: 41–68, 1992) to be applied to the direct selection of diabodies from V-gene repertoires and to the selection of improved diabodies by mutagenesis or chain shuffling. Bivalent diabodies can be displayed on phage, for example by fusing VH-VL or VL-VH domains directly to phage gene3 protein. Between the last V-gene and the phage gene3, an amber stop codon can be inserted leading to incomplete read-throuqh in a suppressor (supE) *E. coli* strain: consequently some soluble chain is produced, which can pair with the chain fused to the gene 3 protein to form a bivalent diabody. Alternatively (but less preferable), a site susceptible to partial in vivo proteolytic cleavage can be engineered at the junction of VH-VL and gene3. Since proteolysis at the V-gene/gene3 junction occurs naturally anyway (apparent from Western blot analysis of phage displaying antibodies; WO92/01047; J. McCafferty et al., 1990 supra), there will always be some soluble VH-VL or VL-VH protein present.

Similarly, bispecific repertoires can be made by fusing one VH-VL or VL-VH combination to the phage gene3 protein (for instance), and expressing the matching VH-VL or VL-VH combination as a soluble fragment. Since in bispecific repertoires it is necessary to express one chain as a soluble fragment, there is no absolute requirement for the amber codon to be present at the antibody-gene3 junction.

Bivalent or bispecific repertoires may also be constructed and displayed on phage as a three-molecule assembly with one VH-VL molecule fused to phage gene3 and the matching VH and VL genes both produced as soluble (but separate) proteins. Finally (but less preferable), bivalent or bispecific repertoires may be constructed by fusing both VH-VL or VL-VH combinations to gene3, and relying on engineered amber codons or engineered or natural proteolysis to produce sufficient material of the soluble V-gene combination to form bivalent/bispecific diabodies.

Like for the construction of scFv or Fab repertoires, various V-gene repertoires can be used as a starting point to create diabody repertoires (H. R. Hoogenboom et al., 1992, supra). Diabody repertoires can be made directly from V-gene repertoires from immunised or "naive" donors (with V-genes isolated from Peripheral Blood Lymphocytes or cells from the bone marrow or spleen), from pools of hybridomas, from EBV-transformed B-cells possibly enriched for antigen binders by in vivo or in vitro immunization, or from in vitro (re)constructed V-genes using cloned germline gene segments, or any combination of these repertoires.

Using these V-gene repertoires, bivalent and/or bispecific diabody repertoires can be constructed in a variety of ways. We discuss here a number of different approaches, but many other methods, which can differ both in detail and concept, could be used.

To construct bivalent diabodies, the cloning of the V-genes can be done by stepwise cloning after introduction of restriction sites at the 5' and 3' end of each of the two V-gene domains, into a suitable phagemid vector with compatible sites and if necessary sequences encoding a short linker to join the genes together in diabody format (FIG. 6, Route I). Alternatively, by using PCR reactions and PCR assembly (splice overlap extension), the VH and VL gene repertoires can be linked together and cloned directly (FIG. 6, route II). This avoids having to design restriction sites compatible with the V-gene sequence or diabody linker sequence. By correct design of the restriction sites, the acceptor phagemid and oligonucleotide primers, one can construct VH-VL or VL-VH diabodies, with any length of linker sequence between the V-genes.

Instead of starting from uncloned and unselected V-gene repertoires, bivalent diabody repertoires can also be obtained by linking VH and VL genes together, which have initially been expressed as scFv or Fab fragments. These may be derived from V-gene repertoires displayed on phage (and possibly selected on antigen to enrich for binders) (FIG. 6, Routes III and IV). For example, by appropriate design of restriction sites a the 3' end of the VH gne and the 5' end of the VL genes, the standard 15-residue linker in scFv constructs can be deleted by a simple cut and paste cloning, yielding a diabody repertoire (FIG. 6, route IIIb). Alternatively, V-gene repertoires in scFv and Fab format can be re-amplified and either cloned stepwise or linked together by PCR-assembly depending on the oligonucleotides used.

To construct bispecific diabodies, where one "helper" specificity is constant, for example an anti-CD16 specificity (binding to the CD16 antigen on Natural Killer cells) or a anti-tumour cell associated antigen, carrier vectors may be created to rapidly combine these specificities (VH-C and VL-C) with a repertoire of VH and VL domains in a bispecific format (FIG. 7, first step of Route A). In this approach, two plasmid vectors are created which carry the appropriate "helper" V-genes (VH-C and VL-C) and restriction sites for direct cloning of V-gene repertoires. Cloning is done such that the VH-repertoire will be linked to VL-C, and the VL-repertoire will be linked to VH-C. This method allows the construction of a library with one constant specificity, and in combination with this, to select a new specificity. For example, an anti-Fc receptor antibody could be combined with a repertoire, selected on tumour cells, and screened for specificities which target Fc-receptor bearing cells specifically to the tumor cells in an in vitro assay.

By using the "helper" V-genes as a dummy, this approach can also be used to construct bispecific diabodies with repertoires at both ends of the diabody (FIG. 7, Route A). Two diabody repertoires are made, one carrying Repertoire A and one helper V-gene combination, and one consisting of Repertoire-B with any other helper V-gene combination. The repertoires can be selected to enrich for binders for specificity A or B, and repertoire B subsequently cloned (without the need for extra PCR) into the reciprocally formatted and selected repertoire A. The difference of this cloning procedure from the ScFv approach (FIG. 7, Route C) is that selections are done directly in diabody format.

Another difference is that in the scFv approach, the recloned V-genes may be shuffled, while on this approach the VH and VL genes always retain the pairing (determined by the first cloning step; VH-A stays with VL-A, VH-B stays with VL-B). This approach allows one to make many different bispecific antibodies with helper V-genes that could encode for example a particular specificity, such as an anti-CD16 specificity as noted above, and could easily be combined with other "helper" V-genes if required.

Bispecific repertoires may also be constructed from V-gene repertoires by the introduction of restriction sites at the 5' and 3' end of each of the 4 V-gene domains, and stepwise cloning into a suitable phagemid vector with compatible sites and if necessary sequences encoding a short linker to join the genes together in diabody format (FIG. 7, Route B, bottom). In another approach, by using PCR reactions and PCR assembly (Splice overlap extension), VH and VL gene repertoires can be linked together and cloned in steps or after assembly of the complete 4-V-gene repertoire cassette (FIG. 7, Route B, top). Assembly avoids having to design restriction sites compatible with the V-gene sequence or diabody linker sequence. By correct design of the restriction sites, the acceptor phagemid and oligonucleotide primers, any diabody format can be constructed.

Instead of starting from uncloned and unselected V-gene repertoires, bispecific diabody repertoires can also be obtained by linking VH and VL genes together from scFv or Fab fragments derived from V-gene repertoires displayed on phage (and possibly selected on antigen to enrich for binders) (FIG. 7, Route C; Example 14). For example, separate scFv repertoires with specificity for the two antigens can be constructed and selected, and V-gene repertoires shuffled by stepwise cloning or PCR assembly to be reformatted as a bispecific diabody. This approach is described in Example 14.

To make large libraries, it should be possible to take advantage of combinatorial infection followed by in vivo recombination, as described in patent application PCT WO92/20791 and patent application WO93/19172. For example, bacteria harbouring a library of random assembled VH-A-VL-B chains on a plasmid (encoding 10 clones of bivalent diabodies) could be infected with phage harbouring a VH-B-VL-A library. The infected bacteria would then produce a bispecific diabody repertoire displayed on phage. The diversity of the diabody sequences displayed on phage should be the product of the diversity of the two libraries.

In the same way, combinatorial infection could be used to assemble highly diverse bivalent libraries of VH and VL genes to encode each diabody chain. However this would require the introduction of a site for recombination, such as loxP site, between the VH and VL genes. Although the structure of the diabody may accomodate these residues, most preferably the sequence is removed. The e.g. loxP site may be encoded within an intron to be spliced out when the protein is expressed. Example 24 illustrates this showing that the self-splicing intron from Tetrahymena can be inserted between the VH and VL sequence, and that after splicing (which only takes place after transcription into RNA), a functional diabody can be formed. On the protein level three amino acids of the internal guiding sequence (IGS) of the intron remain as the only remnant. This is compatible with the diabody format.

To make large repertoires, the self-splicing intron from Tetrahymena can contain a recombination site inserted at a site compatible with self-splicing activity. FIG. 8 demonstrates the principle with a bivalent antibody repertoire. It shows the replicons generated by direct cloning of VH and VL gene repertoires, and the resulting replicon after recombination. Cre-mediated recombination at loxP sites can be carried out in vivo (by superinfection or bacteria carrying both replicons with P1 phage, or by using a temperature dependent P1 lysogen), or in vitro using Cre recombinase. After the recombination, which takes place at the DNA level, the resulting diabody gene is transcribed, and the intron and the loxP site between VH and VL genes are spliced out. The self-splicing system may be applied in a similar fashion to bispecific repertoires.

LIST OF EXAMPLES

Example 1 Construction, expression and characterization of bivalent and bispecific diabody fragments The main aspects covered include:
(a) Construction, expression and characterization of NQ11/D1.3 phOx-D1.3 bispecific diabody
(b) Construction, expression and characterization of bivalent and bispecific diabodies
(c) Construction, expression and characterization of three chain constructs Example 2 Construction and expression of NQ11/D1.3 diabodies with −1 and −2 linker lengths Example 3 Construction and expression of NQ11/B1.8 Ox/NIP diabody Example 4 Characterization of cooperative (allosteric) properties of the NQ11/B1.8 diabody by BIACore analysis Example 5 Construction and expression of MAK195 diabody directed against tumour necrosis factor Example 6 Construction and expression of diabody directed against the V3 loop of gp120 of human immunodeficiency virus Example 7 Construction and expression of Mab32 diabody directed against tumour necrosis factor Example 8 Intracellular expression of Mab32 diabody Example 9 Agglutination of red blood cells using bivalent and bispecific diabodies Example 10 Phage display of a bispecific zero linker D1.3/NQ11 diabody directed against lysozyme and 2-phenyl-5-oxazolone Example 11 Construction of a bispecific diabody with one arm directed against 2-phenyloxazol-5-one and one arm directed against oestriol Example 12 Construction of a fusion between a diabody and a CH3 domain Example 13 Cytolytic activity of bispecific anti-CEA, anti-CD16 antibody: Diabody mediated lysis of human tumour cells by human PBL Example 14 Construction of a repertoire of bispecific diabodies displayed on phage Example 15 Construction and expression of reverse diabody with the VL domain N-terminal to the VH domain bivalent diabody directed against 2-phenyloxazol-5-one Example 16 Evidence that a ten amino acid linker between VH and VL domains favours monomer rather than dimer formation Example 17 Preparation of bispecific anti-NIP, anti-humanFcR1 diabody Example 18 Preparation of bispecific anti-idiotype (bcl1)-antiCD3 diabody and its application to in vitro cytotoxicity Example 19 Preparation and characterisation of bivalent anti-idiotype (bcl1) diabody Example 20 Preparation and characterisation of bispecific anti-HIV gp120 HIV V3 loop-antihumanFcR1 diabody Example 21 Preparation and characterisation of bispecific anti-2-phenyloxazol-5-one, anti-mouse lambda light chain diabody Example 22 Mutagenesis of residues at the interface between the two VH domains of the NQ11/B1.8 Ox/NIP diabody Example 23 Construction and characterisation of diabody with cysteine at the C terminus of the light chain to introduce a disulphide bridge Example 24 Use of self splicing introns in the construction of diabody molecules Example 25 Construction and characterisation of diabody molecules containing fusions with metallothionein Example 1

Construction, Expression and Characterisation of Bivalent and Bispecific Diabody Molecules This example describes the construction, expression and characterisation of various types of diabody molecule, with a range of linker lengths between variable domains:

(a) Bivalent diabodies directed against 2-phenyloxazol-5-one (phOx) or hen egg lysozyme (HEL) using V domains derived from monoclonal antibodies NQ11 (C. Berek et al Nature 316: 412–418, 1985) and D1.3 (A. G. Amit Science 233: 747–753, 1986).

(b) Bispecific diabodies with one arm directed against 2-phenyloxazol-5-one and one arm directed against hen egg lysozyme. (c) Bispecific three chain fragments directed against phOx and HEL.

The diabodies are constructed through common intermediates and will therefore described together.

Methods

Vector construction. *E. coli* TG1 (T. J. Gibson, 1984 Ph.D. thesis, University of Cambridge) was used for propagation of plasmids and expression of antibody fragments. See FIG. 9 for schematic of most constructs (except for constructs VIII and IX). Constructs II, IV and V encoding the scFv (J. McCafferty et al Nature 348 552–554 1990) and Fv (E. S. Ward et al Nature 341 544–546 1989) fragments of the monoclonal antibody D1.3 directed against HEL (A. Amit et al, 1986 supra) were provided by T. Simon. Construct III, encoding the Fv fragment of the mouse hybridoma NQ11.7.22 directed against the hapten phenyloxazolone (C. Berek et al, 1985 supra) was provided by L. Riechmann. Construct III, and those derived from it (constructs I, VI, VII, VIII and IX) include a mutation in the VH domain (Asp 97 to Ala) (L. Riechmann et al J. Mol. Biol. 224 913–918, 1992).

Further constructs (FIG. 9) were derived by religation of restriction fragments (here termed vector fragments and comprising vector backbone and V-genes or parts of V-genes), or their ligation with restriction fragments (here termed PCR fragments and comprising V-genes, linker or non-coding sequences) using standard methods (J. Sambrook et al. Molecular Cloning: A Laboratory Manual, Cold Spring Harbor Laboratory Press, Plainview, N.Y., US 1990). Vector fragments were provided by digestion of construct III with BstEII/SacI, construct II with PstI/SacI and constructs VI with BstEII or XhoI or PstI.

PCR fragments for the 15 residue linkers were generated using primers 1 and 2 (SEQ ID NOS 1 & 2, respectively) with construct IV. Digestion with AscI and SacI yielded PCR fragment a-15 comprising the gene 3 leader, the VH segment and linker. Digestion with BstEII and AscI yielded PCR fragment b-15 comprising linker and the VL segment. PCR fragments for the shorter linkers were generated using: primer 1 (SEQ ID NO: 1) with either primers 3 (SEQ ID NO: 3) or 4 (SEQ ID NO: 4) or 5 (SEQ ID NO: 5) (encoding no, five or ten residue linkers respectively) and primer 2 (SEQ ID NO: 2) with either primers 6 (SEQ ID NO: 6) or 7 (SEQ ID NO: 7) or 8 (SEQ ID NO: 8) (also encoding no, five or ten residue linkers respectively) and digested as above to create PCR fragments a-0, a-5, a-10, b-0, b-5 and b-10. The PCR fragment (c) for providing the non-coding sequence (N1) in construct VII was generated using primers 1 and 2 (SEQ ID NOS: 1 & 2, respectively) with construct V, and digested with BstEII and AscI.

To make constructs VI, PCR fragments (a-0, a-5, a-10 and a-15) from construct IV were ligated with the corresponding PCR fragment b and the vector fragment III-BstEII/SacI. To make constructs VII, PCR fragments (a-5 and a-10) from construct IV were likewise ligated with fragment c. Constructs VIII and IX were derived from constructs VI by partial digestion with PstI or XhoI respectively, and religation of the vector fragment. Constructs I with 5, 10 and 15 residue linkers were likewise generated by BstEII digestion of the corresponding constructs VI. Construct II with 5 residue linker was generated by ligating fragment II-PstI/SacI with fragment a-5 that had been cut with PstI and SacI.

Ligation mixes and transformation was as described (J. D. Marks et al Bio/Technology 10 779–783, 1992). The linker or non-coding regions were sequenced by the dideoxy method (F. Sanger et al Proc. Natl. Acad. Sci. USA 74 5463–5467 1977) using VENT(exo⁻) polymerase (New England Biolabs). The nucleotide sequences of each of the constructs is available from the authors on request.

Oligonucleotides. Sequences of primers used are give in Table 1. Primer 1 (SEQ ID NO: 1) introduces an AscI site and primes at the 3' VL; Primer 2 (SEQ ID NO: 2) introduces a AscI site and a synthetic ribosome binding site and primes at the 5' fd gene 3 signal; Primers 3, 4 and 5 (SEQ ID NOS: 3, 4, & 5, respectively) introduce a linker of 0, 5, 10 residues between VL and VH, include a BstEII site and prime at 5' VL; Primers 6, 7 and 8 (SEQ ID NOS: 6, 7, & 8, respectively) introduce a linker of 0, 5, 10 residues between VH and VL, include a SacI site and prime at 3' VH.

Expression of bispecific fragments. Fragments were prepared from periplasmic lysates (A. Skerra & A. Pluckthun Science 240 1038–1041 1988) or from bacterial supernatants (M. Better et al Science 240 1041–1043 1988). For detection of fragments binding to HEL or phOx-BSA, ELISA was performed as described (H. R. Hoogenboom et al Nucleic Acids Res. 19 4;33–4137 1991). For sandwich-ELISA, plates were coated with HEL and periplasmic lysate or culture supernatant added as above. Binding was detected using 100 μl of 1 μg/ml phOx-BSA, followed by 100 μl of 100 ng/ml of the mouse antibody NQ22.18.7 (C. Berek et al, 1985 supra) directed against phOx and peroxidase conjugated goat anti-mouse immunoglobulin (1:1000) (Sigma). All incubations were made in PBS containing 2% w/v skimmed milk powder. Western blots were as described (20). Fragments were purified from bacterial supernatants by affinity chromatography on HEL-Sepharose (S. Munro & H. R. B. Pelham Cell 46 291–300 1986) and/or phOx-BSA Sepharose as described (M. Dreher Ph.D. thesis University of Cambridge, 1992).

Binding affinities. The dissociation kinetics of antibody fragments to HEL and phOx were measured using plasmon surface resonance with BIAcore (Pharmacia BiosensorAB) as described (A. D. Griffiths et al EMBO J. 12 725–734 1993). For detection of fragments with binding activities to both HEL and phOx-BSA, 10μl of periplasmic lysate or affinity purified fragment was injected onto the HEL coated sensor chip (see above) with a constant flow of 5 µl/min, and followed immediately by a pulse of 10 µl of 1 mg/ml phOx-BSA. The binding affinity of fragments for phOx was measured by fluorescence quench titrations (H. N. Eisen Methods Med. Res. 10 115–121 1964) with the hapten 4-γ-aminobutyryl-2-phenyloxazol-5-one (phOx-GABA) as described (J. Foote & C. Milstein Nature 352 530–532 1991).

Results

We first made constructs for expression of bispecific and bivalent fragments of two different antibodies with 15-residue linkers between the VH and VL domains, as in scFv fragments. 15 residues are sufficient to stretch from the C-terminus of the VH domain to the N-terminus of the VL domain of the same chain (see FIG. 9 for schematic of constructs). However we found that the chains can also pair with each other, as the "bispecific" antibody construct VI with coexpressed cross-over chains (VHA-VLB, VHB-VLA) yielded fragments that bound to both HEL and phOx-BSA. (Table 2). By ELISA, the binding was specific: no binding could be detected to turkey egg lysozyme (TEL) or bovine serum albumin (BSA) and the binding to phOx-BSA could be inhibited by adding soluble hapten. By contrast, when the cross-over chains were expressed separately (constructs VIII and IX), as expected they did not bind to either HEL, TEL, BSA or phOx-BSA in ELISA; when mixed together in vitro however, the two chains did associate as detected by binding to HEL and to phOx-BSA and produced about 10% of the ELISA signal obtained when the two chains were coexpressed.

We also used shorter linker lengths of 5 and 10 residues: the 5-residue linker cannot stretch between VH and VL domains of the same chain, but it does allow the formation of bispecific fragments (Table 2). Indeed, prompted by a computer graphic model of the dimers (see Discussion), we joined the C-terminus of the VH domain directly to the N-terminus of the VL domain. Again the fragment bound to both antigens (Table 1), and also when displayed on the surface of phage using the phagemid vector pHEN1 (Example 10).

A further version of construct VI was prepared with a zero amino acid linker on one chain (VHA-VLB) and a 15 amino acid linker on the other chain (VHB-VLA). 15 amino acids is enough in a linker to allow the two domains of the polypeptide to associate with each other to form an antigen binding site. This again bound to both antigens on ELISA, indicating that this type of dimer "asymmetrical" is functional.

To prove that both antigen binding sites were located on the same bispecific fragment, we used sandwich-ELISA (Table 2) and also BIAcore to show that the bispecific fragments that had bound to HEL also bound to phOx-BSA. For example in FIG. 10(B), the fragments were injected and bound to the biosensor chip coated with HEL (segment bc). After refractive index changes (segment cd) and some dissociation (segment de), the fragments were seen to bind to injected phOx-BSA (the difference in resonance units (RU) between e and h reflects the amount of phOx-BSA bound). As control, FabD1.3 was shown to bind to HEL but the bound fragments did not bind in turn to phOx-BSA (FIG. 10(A)).

The sizes of the fragments binding to HEL or hapten were shown to correspond to dimers by FPLC gel filtration (FIG. 11). We loaded lysate containing the antibody fragment on the FPLC column, and passed the effluent over a BIAcore sensor chip coated with antigen or hapten. The binding of the fragments was detected (in real-time) by an increase in mass at the surface of the chip (A. D. Griffiths 1993 supra). The bispecific fragments were found to be similar in size to a chimaeric D1.3 Fab fragment and bound to chips coated with phOx-BSA as well as to HEL coated chips (Table 2). This indicated that these bispecific fragments must be dimers, formed by association of the two chains.

The sizes of the fragments were also checked by binding of the C-terminal myc tag of the fragments to the monoclonal antibody 9E10 immobilised on the biochip (Table 2). This format detects fragments irrespective of whether they have antigen-binding activities, and allowed us to show that the single cross-over chains (constructs VIII and IX) (that do not bind antigen) were dimers with short linkers, but monomers with long linkers. Again the bispecific fragments emerged in a major peak corresponding to a dimer, irrespective of linker length.

We purified bispecific fragments with 5 and 15-residue linkers, and also with no linker, by affinity chromatography on HEL and then phOx-BSA-Sepharose columns. The yields of the fragments as detected by either Western blots using antibody against the c-myc tag or by binding ELISA were improved when cells were transferred to lower temperature (20° C.) after induction (H. Takagi et al Bio/Technology 6 948–950 1988). After overnight fermentation, most of the protein was located in the culture supernatant, and after affinity purification yielded 0.3 mg/l–1 mg/l of fragment. The yield appears to be comparable to those reported or scFv or Fab fragments (R. Glockshuber et al. Biochemistry 29 1362–1367 1990; A. Skerra & A. Pluckthun Protein Eng. 4 971–979 1991).

We measured the binding affinity for soluble phOx-GABA of bispecific fragments purified on HEL by fluorescence quench titration. The results (Table 3) show that the binding affinities of the bispecific fragments with 5- and 15-residue linkers are similar to the parent Fv. However, the fragment with no linker had a ten fold improved affinity. We also measured the dissociation kinetics of the fragments from phOx-BSA and HEL by BIAcore. The dissociation of the fragment with no linker from phOx-BSA was at least ten fold slower. (Table 2)

We also constructed three chain fragments (FIG. 9, construct VII), in which a single chain VHB-VLA is secreted with the two complementary domains VHA and VLB. The fragments were shown to bind both HEL and phOx (Table 2) and to be bispecific, but the chains appeared to be in fast equilibrium, as on the FPLC the fragments emerged as a single peak between monomer and dimer in size, see (D. H. Jones et al. Biochemistry 24 5852–5857 1985) for discussion and references.

Discussion

Here we describe the design of bispecific antibody fragments by taking advantage of the intermolecular pairing of VH and VL domains. This contrasts with the use of chemical crosslinking or fusion to dimerization peptides. We linked the VH domain of one antibody to the VL domain of another on the same polypeptide chain, to create two chains, VHA-VLB and VHB-VLA, that are co-expressed in the same cell and associate to form dimers with two antigen binding sites on the same molecule. Although we would expect heterodimers, homodimers and monomers to be formed on co-secretion of both chains from the same bacterium, only the heterodimers bind to antigen and can be isolated by a single round of affinity chromatography.

We chose two antibodies, D1.3 and NQ11 for which the VH and VL domains are known to associate and form a stable Fv fragment (E. S. Ward et al 1989 supra; L. Riechmann et al 1992 supra). From the FPLC analysis of the bispecific fragments with 15-residue linkers, it appears that dimers predominate in the lysates (Table 2). Presumably the favourable interaction between the complementary domains on the two different chains helps drive dimer formation. However to promote dimerisation for antibodies for which the VH and VL domains are more weakly associated (A. Skerra & A. Pluckthun 1988 supra), for example in the cross-over chains (constructs VIII and IX), we used short linkers (0 or 5 amino acids) to prevent the VH and VL domains on the same chain from pairing with each other (Table 2).

Many diabodies have been constructed with linker lengths of 0 or 5 amino acids and have been shown to be functional. These include bivalent diabodies directed against 2-phenyloxazol-5-one (phOx) (example 1); lysozyme (example 1); tumour necrosis factor (examples 5 and 7); V3 loop of HIV gp120 (example 4); carcinoembryonic antigen (CEA); Fc receptor FcγRIII (CD16); human Fc receptor FcγRI (example 17); surface Ig of BCL-1 lymphoma cell line (example 19) and the CD3 antigen (example 18). Bispecific diabodies have been constructed directed against phOx and lysozyme (example 1); phOx and NIP (4-hydroxy-3-iodo-5-nitrophenylacetic acid) (example 3); CEA and CD16; NIP and FcRI (example 17); surface Ig of BCL-1 lymphoma cell line and CD3 (example 18); HIV gp120 V3 loop and human FcR1 (example 20) and phOx and oestriol (example 11). A number 0o these have been shown to bind markers on whole cells by FACS analysis including those directed against CEA; CD16 and CD3 (example 18).

Example 2

Construction and Expression of NQ11/D1.3 Diabodies with −1 and −2 Linker Lengths This example describes the construction of a series of bispecific NQ11/D1.3 diabodies based on the NQ11/D1.3 diabody construction made in example 1.

The aim was to investigate the constructional constraints that operate on bispecific diabodies. Reduction in linker length from the fifteen amino acids employed in scFv molecules prevents association of the VH and VL domains from the same polypeptide chain and promotes the formation of diabodies. Example 1 describes 0, 5 and 10 amino acid linkers. In this example the minimum length of linker allowing the formation of active diabody is determined. A series of minus linker molecules (making the linker shorter than zero by removing heavy chain 3' codons or light chain 5' codons) were constructed. The VH-VL linker length was reduced from zero to give (−1), (−2) and (−3) constructs by deletion of amino acids from the N-terminus of the VL domain or the C-terminus of the VH domain. Reduction of linker length further than −1 prevents folding of the NQ11/D1.3 diabody.

Construction of Minus Linker Diabodies

The construction of the diabody NQ11/D1.3 was described in example 1 for 0, 5 and 10 amino acid linkers.

The minus linker length variants were made using the same methodology as in example 1. The linker length between the heavy and light chains was altered by redesigning Primer 3 containing the BstEII site and Primer 6 containing the Sac I site. Each of these primers spans one of the two VH/VL junctions of the diabody Therefore these primers can be altered so that one or more codons are left out of the sequence that spans the VH/VL junction of the final diabody.

When making a (−1) variant, a codon can be deleted from either the 3' end of the heavy chain sequence or the 5' end of the light chain sequence at the VH/VL junction. FIG. 13 shows the four possible variants that were made in this way using the oligonucleotide primers shown in Table 4, the sequences of which are given in Table 1 (SEQ ID NOS: 1, 2, 18, 19, 22, & 23). Construct NQ11/D1.3 (−1) 1–3 has an amino-acid deleted from the C-terminus of the VH domain derived from NQ11 on one polypeptide chain and one amino acid deleted from the C-terminus of the VH domain derived from D1.3 on the other chain. Construct NQ11/D1.3 (−1) 1–4 has an amino-acid deleted from the N-terminus of the VL domain derived from D1.3 on one polypeptide chain and one amino acid deleted from the C-terminus of the VH domain derived from D1.3 on the other chain. Construct NQ11/D1.3 (−1) 2–3 has an amino-acid deleted from the C-terminus of the VH domain derived from NQ11 on one polypeptide chain and one amino acid deleted from the N-terminus of the VL domain derived from NQ11 on the other chain. Construct NQ11/D1.3 (−1) 2–4 has an amino-acid deleted from the N-terminus of the VL domain derived from D1.3 on one polypeptide chain and one amino acid deleted from the N-terminus of the VL domain derived from NQ11 on the other chain. The fragments were cloned into pUC19 and expressed as described in example 1. ELISA was performed as in example 1. All four of these variants, 1–3, 1–4, 2–3 and 2–4 expressed and were active, binding both to 2-phenyloxazol-5-one and to hen egg lysozyme but not to BSA (i.e they bind specifically to their antigens) on ELISA.

FIG. 14 shows two further constructs that were made. The construct NQ11/D1.3 (−2) variant (AE) was made with two codons deleted from the 5' light chain sequence of the NQ11 VH and D1.3 VL junction and two codons from the VH sequence of the D1.3 VH and NQ11 VL junction using the primers shown in Table 4 (SEQ ID NOS: 1, 2, 20 & 24) derived from primers 3 and 6 (SEQ ID NOS: 3 & 6) by the deletion of codons.

The construct NQ11/D1.3 (−3) (CF) was made with three codons removed from each junction. For one polypeptide chain one amino acid was deleted from the C-terminus of the VH domain derived from NQ11 and two amino acids from the N-terminus of the VL domain derived from D1.3, by using the oligonucleotides shown in Table 4 (SEQ ID NOS: 1, 2, 21, & 25) in the construction. For the other polypeptide chain 2 amino acids were deleted from VH domain derived from D1.3 and one amino acid deleted from the N-terminus of the VL domain derived from NQ11 by using the oligonucleotides shown in Table 4 in the construction. When expressed and assayed by ELISA as above, neither the (−2) nor the (−3) variant gave a signal.

Western blots were performed using detection using the monoclonal antibody 9E10 which binds to a myc tag at the C terminus of each of the antibody constructs, as described in H. R. Hoogenboom et al Nucleic Acids Res. 19 4133–4137 1991. Samples analysed on these blots included D1.3 scFv (J. McCafferty et al. Nature 348 552–554 1990), the NQ11/D1.3 (−1) variants 1–3 and 2–3 and the NQ11/D1.3 (−2) construct (AE). The signals show that the (−1) constructs have an expression yield close to that of the scFv proportion of the diabody product however, will be homodimer misfolded material or inactive homogenous chains ie NQ11VH/D1.3 VL paired with itself and D1.3 VH/NQ11 VL paired with itself). The (−2) product was present only at very low concentrations and could only be detected on the blot when samples were concentrated 10 fold.

Consistent problems were experienced when inducing and making diabody variants 1–4 and 2–4. It seems that these two (−1) constructs are just on the edge of being able to fold functionally.

The lower limit for linker length between VH and VL domains in these particular diabody constructs is therefore (−1). It is a possibility that there will be examples of diabodies with different VH and VL domains where (−2) linkers will be functional.

Example 3

Construction and Expression of a NQ11/B1.8 Diabody

This example describes the construction of a bispecific diabody based on the antibody NQ11 (which binds the hapten phOx) and the antibody B1.8 (Roth et al, Eur. J. Immunology, 8 3019 1978 )(which binds the hapten NIP).

Construction of the Diabody NQ11/B1.8

The starting point for this diabody was the existing diabody, NQ11/D1.3. The central D1.3 VK/D1.3 VH part of the construct was excised with the restriction enzymes Bst EII and Sac 1. The B1.8 VL/B1.8 VH sequence could then be cloned into this construct using the Bst EII and Sac I sites.

The B1.8 VL insert for the diabody was made by PCR amplification from an existing B1.8 scFv clone with the primers VLB18baLink0BstE (SEQ ID NO: 33) and VLB18foAsc (SEQ ID NO: 34). The primer VLB18baLink0BstE (SEQ ID NO: 33) contains a Bst EII site compatible with the Bst EII site at the 3' end of the NQ11 VH of the cut vector construct. The primer VLB18foAsc (SEQ ID NO: 34) contains a Asc I site compatible with the Asc I site at the 5' end of the B1.8 VH insert. The B1.8 VL insert was cut with Bst EII and Asc I for cloning into the vector construct.

The B1.8 VH insert for the diabody was made by PCR amplification from an existing B1.8 scFv clone with the primers 2 and 6 (SEQ ID NOS: 2 & 6, respectively). The primer 6 (SEQ ID NO: 6) contains a Sac I site compatible with the Sac I site at the 5' end of the NQ11 VL of the cut vector construct. The primer 2 (SEQ ID NO: 2) contains a Asc I site compatible with the Asc I site at the 3' end of the B1.8 VL insert. The B1.8 VH insert was cut with Sac I and Asc I for cloning into the vector construct.

The Bst EII/Asc I cut B1.8 VL fragment and the Sac I/Asc I cut B1.8 VH fragment were then mixed with the Bst EII/Sac I cut NQ11 vector construct and ligated together generating the NQ11 VH/B1.8 VL//B5.8 VH/NQ11 VL diabody.

Expression of the Diabody NQ11/B1.8

Soluble diabody NQ11/B1.8 was expressed by growth at 37° C. in 2YT/0.1% glucose/100 mg mL to OD550nm of 0.9–1.0 and then induced by adding IPTG to 1 mM. The culture was then grown at a lower temperature (22 or 26° C.) for a further 24 hours.

The soluble antibody from the culture supernatant was shown to bind both NIP and phOx in Elisa with NIP-BSA or phOx-BSA coated Elisa plates. (Coating of Elisa plates was with 100 µl per well overnight with 10 µg/ml NIP-BSA or 10 µg/ml phOx-BSA in PBS). ELISA signals of greater than 1.0 were obtained with each antigen with 50 µl supernatant.

Example 4

Characterization of Allosteric Properties of a NQ11/B1.8 Bispecific Diabody by BIACore Analysis The tight packing of the polypeptide chains in the diabody opens up the possibility of the transmission of a conformation change from one antigen binding site to the other antigen binding site. Allosteric bispecific diabodies in which binding of antigen at one site leads to an increase or decrease in the affinity of binding at the other site have the potential for application to homogeneous assay and prodrug activation.

In this example, the effect of the binding of NIP (4-hydroxy-3-iodo-5-nitrophenylacetic acid) on the affinity of the bispecific NQ11/B1.8 Ox/NIP diabody for phOx was investigated. The NQ11/B1.8 diabody constructed in example 3 was expressed and purified from supernatants by affinity chromatography on a phOx-BSA-Sepharose column. The diabody thus expressed is a dimer of two polypeptide chains NQ11 VH-21.8 VL and 31.8 VH-NQ11-VL. The VH and VL domains were directly fused to each other (zero amino acid linker).

The binding of the diabody to phOx-BSA and NIP-BSA was investigated using surface plasmon resonance (SPR) with the Pharmacia BIACore. The SPR sensor chip surface was derivatized with phOx-BSA to analyse binding of the NQ11 binding site to 2-phenyloxazol-5-one. Normally, when the kinetic rate constant for the dissociation of an antibody ($k_{off}$) from a derivatized chip surfaces is measured, the chip surface is coated with a very low level of antigen. This is to prevent rebinding, which leads to a slower apparent off-rate. However, since the off rate for NQ11 is far too high for conventional BIACore analysis, the chip surface wascoated to a high level with phOx-BSA to exploit rebinding. The off-rate curve observed is now a function of both the rate constant for dissociation of the antibody from the surface ($k_{off}$) and the rate constant for binding of the antibody to the surface ($k_{on}$). The observed off-rate curve is therefore related to the dissociation constant ($k_d$) of the antibody for the antigen at the surface.

FIG. 15 shows off-rate curves for the dissociation of the NQ11/B1.8 bispecific diabody from the phOx-BSA surface. The diabody was bound to the surface in a 'preincubation' step and bound antibody dissociated in an 'elution' step. In each case the curve is shown beginning from 3000 resonance units of diabody remaining bound to the surface and the off-rate is calculated at this point. For curve 1 the buffer for preincubation is PBS and elution is with PBS and an apparent $k_{off}$ of 0.0045 $s^{-1}$ is obtained. For curve 2 preincubation is with 1 µM NIP/PBS and elution is with PBS and an apparent $k_{off}$ of 0.0047 $s^{-1}$ is obtained. For curve 3, preincubation is with PBS and elution with 1 µM NIP/PBS and an apparent $k_{off}$ of 0.0069 $s^{-1}$ is obtained. For curve 4, preincubation is with 1 µM NIP/PBS and elution with 1 µM NIP/PBS and an apparent $k_{off}$ of 0.0071 $s^{-1}$ is obtained. Thus curves 3 and 4 where 1 µM NIP is present in the elution buffer shows a 50% higher apparent $k_{off}$ compared to curves 1 and 2 in the absence of NIP in the elution buffer. This NIP increases the apparent $k_{off}$ and decreases the apparent binding affinity of the NQ11/B1.8 diabody for phOx. Because the interaction is complex, the off-rate curve is a complex function of $k_{off}$ and $k_{on}$. The effect on the true dissociation constant cannot be quantitated but it is clear that the binding of NIP affects the binding of phOx.

Preincubation with NIP has no effect on the observed off rates, although there is some evidence that preincubation with NIP reduces the total amount of diabody binding to the chip, in accord with the observed effect of NIP on the dissociation of the diabody from the phOx coated surface.

NIP had no significant effect on the binding of scFvNQ11 to the phOx-BSA coated surface.

No allosteric effect was seen for the presence of phOx on the off-rate curve of the NQ11/B1.8 diabody from a NIP-BSA coated sensor chip surface.

To investigate this further, we made equilibrium binding trials with a separate preparation of the diabody in the absence (control) and presence (test) of 1 µM NIP. Each dilution was run over a sensor surface modified with 2000 RU of BSA-Ox$_{4.6}$ ("s2"); a surface modified with 7900 RU of BSA-Ox$_{1.8}$ ("s3"); and an unmodified surface to measure the bulk refractive index of each sample. FIG. 16 (upper portion) shows the corrected equilibrium binding ("Req") curves for binding to s2 in the presence and absence of NIP, and FIG. 16 (lower portion) that of binding to s3. In both cases, NIP reduces the binding of the diabody to the BSA-Ox surface. It is also clear that, although saturation was not attained, the maximal binding even for control was much less than would be expected if all of the hapten molecules on the BSA were equally active as antigen.

The data were treated by Scatchard analysis to obtain estimates of affinity. However, it was necessary to make several assumptions in order to calculate the affinities. It was assumed that the diabody was 100% pure and 100% active, and that a single class of binding sites existed on the surface. Since the data for the lowest concentration of antibody (especially for the sample containing NIP) were significantly off the fitted line, probably resulting from a failure to achieve equilibrium, these results were omitted from the analysis. FIGS. 17 and 18 show the binding of the diabody to s2 and s3 respectively. The Kd for the diabody was found to be 275 nM on s2, with a calculated maximum binding (Rmax) of 510 RU; the respective values for s3 were 275 nM and 355 RU. In the presence of NIP, however, the apparent Kd for Ox was 425 nM on s2 and 418 nM on s3. The Rmax values (461 and 348 RU respectively) agreed reasonably well with those for controls. Clearly the quantitation of the effect depends critically on our assumptions. Our data probably give a lower limit for the effect, since the assumption that all the molecules of the diabody had 100% activity is probably false. Fluorescence quench measurements on similar preparations gave an activity for each hapten of around 30%. If there are diabody molecules with an active Ox-binding (B1.8) site but an inactive NIP-binding (NQ11) site, these would bind to the BSA-Ox surfaces unaffected by the presence of NIP, and this would reduce the apparent effect of the NIP on total binding to the BSA-Ox. Furthermore, hapten molecules provide several epitopes on BSA, and it is possible that this results in several classes of binding sites.

Nevertheless it is clear that the data show that the addition of a first hapten (NIP) to the diabody alters the apparent affinity of the diabody to at least one class of binding sites for the second hapten (phOx), perhaps by transmission of a conformational change in the molecule upon binding of the first hapten.

Thus there is an allosteric effect of NIP on the binding of phOx-BSA by this diabody. This is the first observation of such an allosteric effect for an antibody.

Example 5

Construction and Expression of MAK195 Diabody Directed Against Human Tumour Necrosis Factor Alpha MAK195 is a murine monoclonal antibody that binds specifically to human TNFα (A. Möller, F. Emling, D. Blohm, E. Schlick and K. Schollmeier. Monoclonal Antibodies to human tumor necrosis factor alpha: in vitro an in vivo applications. Cytokine 2, 162–169, 1990). It has been cloned in a diabody format using a 5 residue linker GGGGS (SEQ ID NO: 86) in the orientation VH-VL in the phagemid vector pCANTAB5myc (FIG. 19, WO92/01047). The linker sequence was incorporated into the primer (AJR21 (SEQ ID NO: 9)) used to amplify the 5' end of VK. A restriction site for BstEII was incorporated 5' of the linker sequence of primer AJR21 (SEQ ID NO: 9) and also at the 3' end of VH1FOR-2 (E. S. Ward, D. Gussow, A. D. Griffiths, P. T. Jones and G. Winter, Nature 341, 544–546 1989), allowing the VH and linker-VL fragments to be cloned in a 3-way ligation reaction into the expression vector pCANTAB5myc.

RNA was extracted from MAK195 hybridoma cells and used to prepare cDNA. MAK195 VH and VL domain DNA was amplified by PCR from cDNA using primers pairs MAKVHBACKNCO (SEQ ID NO: 10) and VH1FOR-2, and AJR21 (SEQ ID NO: 9) and VK4FORNOT1 (T. Clackson, H. R. Hoogenboom, A. D. Griffiths and G. Winter, Nature 352, 624–628 1991) respectively using standard conditions. (Note: since the MAK195 V-genes had been cloned and sequenced previously, we designed a MAK195-VH specific primer rather than use the "standard" VH1BACK primer (R. Orlandi, D. H. Gussow, P. T. Jones and G. Winter, Proc. Natl. Acad. Sci. USA 86, 3833–3837 1989)) The product of the VH PCR reaction was digested with restriction enzymes NcoI and BstEII, and the product of the VL PCR reaction was digested with restriction enzymes NotI and BstEII. The VH and the VL domain DNA was simultaneously ligated into NcoI/NotI digested pCANTAB5myc in a molar ratio 3:3:1 (VH:VL:pCANTAB5myc) and the resulting ligation mix used to transform *E. coli* TG1 cells. The sequence of some of the recombinant clones was confirmed using standard vector-based primers. We have called these constructs MAK195-5.

Soluble diabody was expressed by growth at 24° C. Cells in log phase growth in 5 mL 2YT/1% glucose/100 µg mL$^{-1}$ ampicillin were resuspended in 5 mL 2YT/1 mM IPTG/100 mg mL$^{-1}$ ampicillin and grown 3 hours 24° C. The cells were centrifuged (1000 g 10 minutes) and the cell pellet resuspended in 250 µL ice cold PBS/1 mM EDTA and left on ice, 15 minutes. The cell suspension was centrifuged (1000 g for 10 minutes) and the diabody-containing supernatant used in ELISA.

50 µL periplasmic supernatant+50 µL 3% marvel/PBS was added to ELISA wells coated with recombinant human TNFα (10 µg mL$^{-1}$ in 0.1M NaHCO3 pH9.6), blocked with 3% marvel/PBS. A standard ELISA protocol was followed (H. R. Hoogenboom et al., Nucl. Acids Res. 19, 4133–4137 1991) using detection of the myc-tag with the monoclonal antibody 9E10, and horseradish peroxidase conjugated anti mouse IgG. ELISA readings after 90 minutes are shown in FIG. 21. When expression of the clones was induced at 30° C., no binding to TNF could be detected (not shown). However, when expression of the clones was induced at 24° C., and ELISA was performed at both 37° C. and room temperature, comparable positive signals were obtained. This indicates that this diabody is stable at 37° C. but requires lower temperatures for efficient expression.

Example 6

Construction of a 5-Linker Diabody Recognising the V3 Loop of HIV gp120

Mab447-52-D is a human monoclonal antibody recognising the V3 loop of HIV 9p120 (Gorny, M. K., J.-U. Xu., V.

Gianakakos, S. Karawowska, C. Williams, H. W. Sheppard, C. V. Hanson, and S. Zolla-Pazner. 1991. Production of site-selected neutralizing human monoclonal antibodies against the third variable domain of the HIV-I envelope glycoprotein. Proc. Natl. Acad. Sci. USA 88:3238–3242). When cloned as a scFv the antibody retains its antigen specificity, binding to gp120 and to synthetic peptides representing the V3 loop sequence. 447:P4B1 is a higher affinity variant of 447-scFv: four amino acid subsitutions together allow a decreased rate of dissociation from peptide antigen. A bivalent 447 diabody was engineered by reducing the length of the linker sequence joining heavy and light chain variable regions from 15 to 5-residues.

DNA fragments encoding the antibody heavy and light chain variable regions were prepared separately by PCR amplification of the template 447:P421 scFv cloned in the phagemid vector pCANTAB5myc (FIG. 19). The heavy chain fragment was generated using the vector-specific primer PUC19rev (Table 1 (SEQ ID NO: 26)) and the primer HuJH6ForLINK (Table 1 (SEQ ID NO: 27)) which is specific for the JH-region of the antibody (bold) and the first 5 residues of the scFv linker (underlined). The light chain fragment was similarly prepared using a vector specific primer, FDTSEQ1 (SEQ ID NO: 28) and the primer LINKHul1Back (Table 1 (SEQ ID NO: 29)) which is complementary to the linker region of HuJH6ForLINK (underlined) and specific for the antibody light chain (bold). PCR assembly (T. P. Clackson et al 1991 supra) of the primary PCR products was accomplished by virtue of the linker sequence-complementarity between the primers HuJH6ForLINK and LINKHul1Back (SEQ ID NOS: 27 & 29, respectively). The assembled product was then re-amplified using primers PUC19rev and FDTSEQ1 (SEQ ID NOS: 26 & 28, respectively), digested with NcoI and NotI as per standard protocols, and cloned in pCANTAB5myc.

The diabody 447:P4B1(5) was tested in a soluble capture assay for recognition of a synthetic peptide representing the V3 loop sequence. Periplasmic extracts of scFv and diabody were firstly prepared from overnight cultures of TG1 transformed with the appropriate construct. The soluble extracts were preblocked In 3% Marvel/PBS for 30 minutes at 30° C. 100 nM biotinylated peptide antigen was then added to 100 $\mu$l of each periplasmic extract and the mixtures allowed to equilibrate for 1 hour at 30° C. After incubation the samples were mixed briefly (2 mins) with preblocked streptavidin dynabeads and the beads were then recovered on a magnet and washed well with PBS. Antibody bound to the biotinylated antigen was detected using the mouse monoclonal antibody 9E10 which recognises the myc-tag at the C-terminus of the scFv or diabody fragment. 9E10 was in turn detected using alkaline phosphatase-conjugated Goat anti-mouse IgG, the reactions developed with PNPP and absorbance measured in a microtitre plate reader at 405 nm. The scFv clone 447 P4B1(15) gave an absorbance of 1.0 whereas the diabody clone P4B1(5) gave an absorbance of 1.37. Hence the diabody directed against HIV gp120 V3 loop is functional.

Example 7

Construction and Expression of Diabodies from the Murine Mab32 Antibody and a Humanised Derivative, P3A2, Directed Against Human Tumour Necrosis Factor Alpha.

Mab32 Diabody

The murine Mab32 antibody has been cloned and expressed as a single chain Fv (scFv) with the standard 15-residue linker (sequence (GGGGS)$_3$) (SEQ ID NO: 98) after cloning from the cDNA using the standard primers (Clackson et al., 1991, supra; WO93/06213). This construct was used as a starting point for the diabody construction. The MAb32 VL was re-amplified with FL-VL (SEQ ID NO: 11) or ZL-VL (SEQ ID NO: 12), and fd-tet-seq24 (SEQ ID NO: 13) as PCR primers from the scFv template, and cloned as BstEII-NotI cut fragment into plasmid DNA containing the VH gene (pHEN1-VH-Mab32, BstEII-NotI cut). This generated clones with the VH domain fused go the VL domain with a 5 or 0 amino acid linker (for FL-V1 and ZL-VL primers respectively). The diabody sequence was confirmed by sequencing using standard primers based in the vector pHEN1 and oligonucleotide Mab32-VL-REV (SEQ ID NO: 14).

The activity of the diabody was confirmed in ELISA with coated antigen (human TNF-alpha) as described in example 5 (FIG. 22). As seen before, more active material is obtained when the diabody is induced and grown at room temperature (Appr. 20–24° C.) compared with 37° C. Results are shown for Mab32–0 (zero-linker diabody); Mab32-5 (5-residue diabody, with GGGGS linker); Mab32-15 (scFv linker).

To obtain an estimate of the relative amount of protein produced in culture supernatant of the Mab32 diabody and single-chain Fv clones, we carried out a slot blot assay. Culture supernatant (10 $\mu$l=neat; and 10-fold dilutions of this in 2 X YT) was spotted onto Hybond-C membrane (Amersham), the membrane dried, and blocked with 3% Marvel. Mab32 molecules bound to the filter were detected with the 9E10 antibody directed against the myc tag present at their C-terminus. After incubation with 9E10 (appr. 1 $\mu$g/ml), washing with PBS-Tween-20 (0.1%), and incubation with peroxidase labeled goat anti-mouse Ig, the bound antibody was detected by enhanced chemiluminescence (Amersham). The slot blot (FIG. 23) confirms that the ELISA signals correlate with the amount of material produced at that temperature. Although the ELISA signal for the Mab32-0 and Mab32-5 diabodies are slightly higher than for the Mab32-scFv, there is also more material being produced (at 30° C. and at room temperature).

The human antibody P3A2 (described in WO93/06213) was cloned earlier as a scFv fragment using standard primers (Clackson et al., 1991, supra). This scFv DNA was used as template in a PCR to re-amplify the VH (with primers pUC-reverse (SEQ ID NO: 68) and VH1FOR-1Xho) and the VL gene (with primers FL-VL-A2 (SEQ ID NO: 15) or ZL-VL-A2, and fd-tet-seq24 (SEQ ID NO: 13)), to make a five residue and a zero residue linker diabody. After restriction with NcoI and XhoI (VH) and XhoI and NotI (VL), the two fragments were ligated together in the phagemid vector pHEN1 (NcoI-NotI cut), and the VH-VL junction of recombinant clones sequenced using VLA2-REV (SEQ ID NO: 17).

Minimal binding of the diabody was obtained after induction and growth at 30° C.; a better signal was obtained when the diabody was produced at room temperature. A slot blot with the 9E10 antibody (FIG. 23) confirmed that, again, the ELISA signals correlate with the amount of material produced at that temperature.

Example 8

Production, Folding and Characterisation of a Diabody Expressed Intracellularly in *E. coli*: Mab 32 diabody directed against tumour necrosis factor This example describes the production in *E. coli* of a diabody directed against tumour necrosis factor, derived from the mouse monoclonal antibody Mab32. The protein is expressed intracellularly and then refolded using a redox denaturation-renaturation procedure which was carefully optimized to maximize the amount of correctly folded dimer. The principle of this redox denaturation-renaturation procedure is described in the Danish patent applications entitled 'Processing of polypeptides', DK0130-93 and DK0139-93 (H. C. Thøgersen, T. L. Holtet and M. Etzerodt).

A phagemid clone containing Mab32 encoded in the diabody format with a 5 amino acid linker (described in example 7) was used as template in a polymerase chain reaction to produce a cDNA fragment corresponding to the Mab32 diabody.

The primers for the PCR were designed to incorporate at the 5' end a DNA sequence encoding the amino acid sequence GSIEGR (SEQ ID NO: 99) which constitutes a cleavage site for the bovine restriction protease, Factor Xa (K. Nagai and H. C. Thøgersen Methods in Enzymology 152 461–481, 1987). The amplified DNA fragment was subcloned into the E. coli expression vector pT7H. (Christensen et al. FEBS Letters 295 181–184, 1991) to generate the plasmid $pT_7H_6FX$-DB. This plasmid was transformed into E. coli BL21 cells.

To prepare the diabody fragment, the plasmid pT7H6FX-DB was grown, as described by Studier and Moffat (J. Mol. Biol. 189 113–130, 1986) in 4 liters of 2xTY media containing 100 μg/ml and 5 mM $MgSO_4$ at 37° C. until $A_{600}=0.8$. Exponentially growing cultures were then infected with the bacteriophage λCE6 at a multiplicity of infection of approximately 5. Forty minutes after infection, rifampicin was added (0.2 g in 2 ml methanol per liter media) and the cells harvested after 4 hours. Cells were resuspended in 150 ml of 0.5M NaCl, 10 mM Tris-HCl, pH8, 1 mM EDTA. Phenol, pH8 (100 ml) was added and the mixture sonicated to extract the total protein. Protein was precipitated from the phenol phase by the addition of 2.5 volumes of ethanol and centrifugation.

The protein pellet was dissolved in a buffer containing 6M guanidium chloride, 50 mM Tris-HCl, pH8 and 0.1M dithioerythritol. Following gel filtration on Sephadex G25 (Pharmacia, Uppsala, Sweden) into 8M urea, 1M NaCl, 50 mM Tris-HCl, pH8 and 10 mM 2-mercaptoethanol, the crude purified protein was applied to a $N^{2-}$ activated NTA-agarose column (75 ml washed with 8M urea, 1M NaCl, 50 mM Tris-HCl, 10 mM 2-mercaptoethanol) for purification (Hochuli, Bannwarth, Dobeli, Gentz and Stuber Bio/Technology 6 1321–1325, 1988). The column was washed with 200 ml of 8M urea, 1M NaCl, 50mM Tris-HCl, pH8, 10 mM 2-mercaptoethanol (Buffer I) and 100 ml 6M guanidium chloride, 50 mM Tris-HCl, pH8, 10 mM 2-mercaptoethanol (Buffer II). The MGSHHHHHHSIEGR-fusion protein (SEQ ID NO: 100) was eluted with Buffer II containing 10 mM EDTA and the eluate was gel filtered on Sephadex G25 using Buffer I as eluant.

The protein eluted was then refolded. The protein was mixed with 100 ml Ni-NTA Sepharose. The resin containing bound protein was packed into a 5 cm diameter column and washed with buffer I. Refolding was now performed using the cycling program shown in Table 5 at 11° C.–12° C. using the following buffers:

Buffer A: 50 mM Tris-HCl, pH8; 0.5M NaCl; 2 mM reduced glutathione (GSH); 0.2 mM oxidized glutathione (GSSG)

Buffer B: 50 mM Tris-HCl, pH8; 1M NaCl; 3 mM GSH; 8M urea

Protein was eluted from this column using 50 mM Tris-HCl; 0.5M NaCl; 25 mM EDTA and then made to 5 mM GSH, 0.5 mM GSSG and incubated for 12 to 15 hours at 20° C. to complete refolding in the correct molecular form. The protein was then concentrated 50 fold by ultrafiltration using YM10 membranes. In FIG. 24 the refolding conditions are analysed by electrophoresing proteins on a non-reducing SDS-polyacrylamide gel and it is shown that the conditions used in this example (Track 9) give the highest yield of refolded product.

Diabody dimer was purified by gel filtration using a Superose 12 column with PBS as eluant.

The overall yield of correctly folded material Mab32 diabody from this procedure was approximately 4 mg per liter. This represents a 20% overall refolding yield.

An analysis by non-reducing SDS-PAGE of proteins from various stages of the purification is shown in FIG. 25.

The his6 tag could be cleaved from the N-terminus of the diabody product by treatment with Factor Xa (molar ratio 1:5 FactorXa: diabody) at 37° C. for 20 h. This is shown as the appearance of a lower molecular weight band just below the uncleaved material in FIG. 26. Properties of Purified Intracellularly Expressed Mab32 Diabody 1. Mab32 Diabody Binds Specifically to Human TNF-alpha.

TNF-alpha and BSA were coated at 10 μg/ml in 0.1 M Sodium Carbonate buffer overnight at 4° C. After blocking for 1 hr with 2% Marvel, and washing with PBS-Tween-20 (0.1%) and PBS, the diabody was added in 2% Marvel, and subsequently detected with the 9anti-myc tag E10 antibody and peroxidase-labeled goat anti-mouse Ig. As shown in FIG. 27, the Mab32 diabody binds specifically to TNF-alpha, with a minor cross-reactivity with BSA only visible at the highest concentration of diabody.

2. Mab32 Diabody Competes with the Mab32 Whole Antibody for Binding to TNF.

TNF-alpha and BSA were coated at 10 μg/ml in 0.1 M Sodium Carbonate buffer overnight at 4° C. After blocking for 1 hr with 2% Marvel, and washing with PBS-Tween-20 (0.1%) and PBS, the Mab32 whole antibody was added in 2% Marvel, and subsequently detected with peroxidase-labeled goat anti-mouse Ig. The same ELISA was repeated, now adding competing diabody to the wells (10 μl of the preparation, equivalent to 0.21 mg/ml). FIG. 28 shows how the diabody competes extremely effectively the (bivalent) Mab32 antibody off the TNF coated surface.

3. Mab32 Diabody Competes with the Sheep Anti-301 Antiserum.

Anti-301 antiserum was raised by immunizing sheep with a peptide encoding the first 18 amino acid residues of human TNF-alpha, and comprised at least part of the epitope recognised by the murine Mab32 antibody. To analyse the serum, a control ELISA with the Mab32 antibody was carried out. The same ELISA as in (2) was repeated, now adding competing sheep anti-301 antiserum to the wells (10 μl of undiluted serum) together with the Mab32 whole antibody (in 3-fold dilution as before) (FIG. 29 upper). Also, the same ELISA as in (1) was repeated, now adding competing sheep anti-301 antiserum to the wells (10 μl of undiluted serum) together with the diabody (in 3-fold dilution as before) (FIG. 29 lower). As shown in the Figures, like the parent antibody Mab32, the diabody is competed off the TNF surface by the addition of the anti-301 antiserum, indicating that the diabody recognises the same epitope on TNF as the parent antibody.

4. Mab32 Diabody is Bivalent.

TNF-alpha was coated at 10 μg/ml in 0.1 M Sodium Carbonate buffer overnight at 4° C. After blocking for 1 hr with 2% Marvel, and washing with PBS-Tween-20 (0.1%) and PBS, the Mab32 diabody was added in 2% Marvel and left for one hour. After washing, the wells were incubated for 30 minutes with a sample containing biotinylated TNF in 2% Marvel, and 30 minutes with peroxidase-labeled Extravidin (Sigma, Code E-2886). FIG. 30 shows how the diabody can be detected in this ELISA setup, proving that at least part of the preparation is a bivalent molecule.

Example 9

Agglutination of Red Blood Cells Coated with Antigen Using Bivalent and Bispecific Diabodies Agglutination of red blood cells coated with antigen serves both as a definitive test of the presence of two antigen binding sites in the dimeric diabody and as a model for the use of diabodies in agglutination assays for diagnostic tests.

In this example, three diabodies and a single chain Fv fragment were tested for their ability to agglutinate antigen coated red blood cells : NQ11/D1.3 diabody with a zero amino acid linker, directed against phOx and hen egg lysozyme (NQ11/D1.3/0; example 1); D1.3 diabody with a 5 amino acid linker directed against hen egg lysozyme (D1.3/5; example 1); D1.3 diabody with a zero amino acid linker (D1.3/0; as D1.3/5 but VHD1.3 directly fused to VLD1.3) and scFvD1.3 (J. McCafferty et al, 1990 supra).

Preparation of Antigen Coated Red Blood Cells

Human red blood cells (RBC's) were used for this technique. Having removed and discarded the buffy coat from the red blood cells, they were washed, spun down and resuspended four times with PBS, each time discarding the supernatant. It was important not to mix cells of different blood groups prior to this washing stage. After the final wash and spin, the packed RBC's were coated with protein by mixing RBC's, coating protein solution (20 mg/ml or less in PBS of lysozyme or phOx-BSA) and 1-Ethyl-3(3-Dimethylaminopropyl) carbodiimide (EDAC; 100 mg/ml in PBS) in the ratio 1:4:1 (v/v). This mixture was turned end over end on a rotating platform at 4° C. for 1.5 hours after which the RBCs were spun down and the supernatant removed and discarded. Subsequently, the cells were washed 5 times in approximately 10 ml PBS (until there was no further haemolysis) and then resuspended in a final volume of 10 ml PBS ready for use.

Assay Procedure

The clones for the antibody fragments were expressed in the bacterial periplasm at room temperature (approximately 24° C.) with induction using 1 mM IPTG as described in example 1. To each except the first column of wells in a sterile round bottomed microtitre plate, 50 µl of PBS was added. To the first column of wells, 62 µl of periplasmic preparation was added (in duplicates). Five-fold dilutions were made of the contents of the first wells across the plate by transferring 12 µl from well to well (discarding 12 µl from the final well). To the first row of each pair, 50 µl of antigen coated RBC's was added, and to the duplicate of each, 50 µl of RBC's treated with EDAC in PBS in the absence of coating antigen was added. The contents of the wells were mixed by gentle shaking and the plate allowed to stand undisturbed at room temperature for 60–90 minutes.

Results

The occurence of an even mat of cells coating the whole of the bottom of a well indicates the occurence of haemagglutination, indicated by a '+' in Table 6. If no haemagglutination occurs, the cells form a tight button in the centre of the well.

The D1.3/5 and D1.3/0 bivalent diabodies show agglutination with both neat periplasmic supernatant and with a 1 in 5 dilution with lysozyme coated red blood cells but not with phOx-BSA coated red blood cells or uncoated red blood cells, showing the presence of bivalent fragments. In contrast the scFv D1.3, which as shown in example 1, exists as an equilibrium between the monomer and the dimer, does not agglutinate the blood cells. The NQ11/D1.3/0 bispecific diabody shows agglutination with a mixture of red blood cells coated with lysozyme and red blood cells coated with phOx-BSA but not with red blood cells coated with phOx-BSA or lysozyme only. This indicates the presence of bispecific diabodies in the periplasmic preparation.

Example 10

Phage Display of a Bispecific Zero Linker D1.3/ NQ11 Diabody Directed Against Lysozyme and 2-Phenyl-5-oxazolone This example shows that the bispecific zero linker D1.3/ NQ11 diabody directed against lysozyme and 2-phenyl-5-oxazolone can be fused to gene III of filamentous bacteriophage and displayed on bacteriophage with retention of binding to both antigens.

Construct VI (no linker) from example 1 was recloned into the phagemid pHEN1 (H. R. Hoogenboom et al, Nucleic Acids Res. 19 4133–4137 1991) for phage display. The fragment encoding both polypeptide chains was excised by digestion with HindIII and partial digestion by XhoI. The larger fragment generated from the partial digest was purified by gel electrophoresis using methodology as described in J. D. Marks et al (J. Mol. Biol. 222 581–597 1991). This fragment was ligated into PstI/XhoI cut pHEN1 and electroporated into TG1.

The phagemid was rescued with M13K07 and the supernatant containing phage assayed directly. Phage supernatant (50 µl) was used in ELISA with phOx-BSA and hen egg lysozyme coated plates as in example 1 except that sheep antibody directed against M13 was used to detect binding of phage antibody as in J. McCafferty et al. (Nature 348 552–554, 1990) The NQ11/D1.3/0 bispecific diabody bound to both antigens when displayed on the surface of phage. An absorbance signal of 2.8 was obtained with hen egg lysozyme and 2.7 with phOx-BSA compared with a background value of 0.1.

Example 11

Construction of a Bispecific Diabody NQ11/OE13

A clone encoding a bispecific diabody directed against 2-phenyloxazol-5-one and hormone oestriol with a 5 amino acid linker was prepared from DNA encoding a single chain Fv fragment directed against 2-phenyloxazol-5-one described in example 1 and from DNA derived from a hybridoma OE13 (Amerlite Diagnostics Ltd) directed against oestriol using the methodology essentially as described in example 1.

The VH and VK domains of OE13 were amplified from single chain Fv DNA derived from the hybridoma V genes and cloned as an ApaLI-NotI fragment into fd-tet-DOG1 using primers and methodology as described by Clackson et al (1991 supra). The DNA encoding the scFv fragment was excised from the fd-tet-DOG1 clone as a PstI-NotI fragment and was recloned into pHEN-1.

DNA from this clone was used in PCR to amplify the V genes as in example 1 using the primers VH1BACK, VH1FOR-2, Vk2BACK and Vk4FOR. The intergenic region including the gene III leader sequence was amplified by PCR with primers NterVHfo (SEQ ID NO: 50) and CterVkba (SEQ ID NO: 51). The 3 fragments were assembled by splicing by overlap extension (Clackson et al, 1991) and the assembly product gel-purified and re-amplified with the primers VkbaLink5-SacBstE (SEQ ID NO: 52) and VH1fo-BstELink5Sac (SEQ ID NO: 53). This gives an OE13 VK-intergenic region-OE13VH insert.

The primers VkbaLink5-SacBstE (SEQ ID NO: 52) and VH1fo-BstELink5Sac (SEQ ID NO: 53) each contain the correct sequence to create 5 amino acid linkers, GGGGS, (SEQ ID NO: 86) between the heavy and light chains of the final diabody construct. The primer VkbaLink5-SacBstE (SEQ ID NO: 52) contains a restriction site for Bst EII 5' to the linker sequence and the primer VH1fo-BstELink5Sac (SEQ ID NO: 53) contains a Sac I site 5' to the linker sequence. The OE13 insert amplified with these primers can therefore be digested with Bst EII and Sac I and inserted into a Bst EII/Sac I cut vector.

The OE13 insert was cloned into a FvNQ11 construct (see Example 1, construct III) in pUC19. This was prepared by cutting the NQ11/pUC19 with Bst EII and Sac I. The OE13 insert was ligated into this with a molar ratio of 3:1 (VLN2VH:pUC19-NQII). The resulting ligation mix was used to transform *E. coli* TG1 cells. Recombinants were screened for inserts of the correct size by PCR amplification of inserts from recombinant colonies using the primers LMB2 and LMB3 (SEQ ID NOS: 84 & 85, respectively).

These clones was assayed for ability to bind their antigen by ELISA using plates coated at 10 µg/ml with Ox-BSA (approximately 10 to 12 mol phOx/mol BSA) or 10 µg/ml with oestriol-BSA (approximately 30 mol oestriol/mol BSA). Periplasmic supernatant (50 µl) and 50 µl 4% Marvel/PBS was added to ELISA wells coated with phOx-BSA or oestriol-BSA. A standard ELISA protocol was followed using detection of the myc-tag with monoclonal antibody 9E10. Positive ELISA signals (>1.0) were obtained.

Example 12

Construction of a Fusion Between a Diabody and a CH3 Domain

A diabody may be genetically fused to other proteins, or other antibody domains. This example demonstrates that a diabody can be generated fused to the CH3 domain of human IgGγ4 with retention of the ability of to bind antigen at both ends of the molecule, provided that a linker of sufficient size is inserted at the junction.

The human CH3 domain of a IgGγ4 (gift of T. Simon was fused to the C-terminus of the NQ11/D1.3 bispecific diabody described in example 1. It was fused either directly or with a 15 amino acid flexible spacer between the C-terminus and the CH3 domain.

NQ11/D1.3/0 was cut out by digestion of pUC19-NQ11/D1.3/0 with HindIII and partial digestion with XhoI (example 1).

A XhoI restriction site was introduced in the primers HuCH3baXho and HuCH3baLinkXho used to amplify 5' end of CH3 domain. A EcoRI restriction site was introduced in the primer HuCH3foEco used to amplify 3' end of CH3. This allowed the diabody and the CH3 fragments to be cloned in a 3-way ligation reaction into the expression vector pUC119SfiNotmyc.

Construction of the Diabody NQ11/D1.3/CH3.

To construct a diabody directly linked to the human CH3 chain, the human CH3 domain of a IgGγ4 was PCR amplified with primers HuCH3foEco and HuCH3baXho using standard conditions. PCR products (CH3 and LinkCH3) were cut with XhoI and EcoRI. The diabody fragment HindIII/XhoI and the CH3 domain DNA was simultaneously ligated into HindIII/EcoRI digested pUC119SfiNotmyc in a molar ratio 2:3:1 (NQ11/D1.3/0:CH3:pUC119SfiNotmyc) and the resulting ligation mix used to transform *E. coli* TG1 cells. Recombinants were screened for inserts of correct size by PCR amplification of recombinany colonies using the primers HuCH3foEco and LMB3 (SEQ ID NO: 85).

Construction of the Diabody NQ11/D1.3/linker/CH3.

To construct a diabody with a 15 amino acid linker to the CH3 domain, a simimlar protocol was followed. The human CH3 domain of a IgGγ4 was PCR amplified with primers HuCH3foEco and HuCH3baLinkXho using standard conditions. PCR products (CH3 and LinkCH3) were cut with XhoI and EcoRI. The diabody fragment HindIII/XhoI and the CH3 domain DNA was simultaneously ligated into HindIII/EcoRI digested puC119SfiNotmyc in a molar ratio 2:3:1 (NQ11/D1.3/0:CH3:pUC119SfiNotmyc) and the resulting ligation mix used to transform *E. coli* TG1 cells. Recombinants were screened for inserts of correct size by PCR amplfication of recombinant colonies using the primers HuCH3foEco and LMB3 (SEQ ID NO: 85).

Soluble diabody was expressed by growth at 37° C. Cells in log phase growth in 2 mL 2YT/0.1% glucose/100 mg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 µl ice cold PBS/1 mM EDTA and left on ice, 60 minutes. The cell suspension was centrifuged (1000 g for 10 minutes) and the diabody-containing supernatant used in ELISA.

When analysed by ELISA for binding to phOx and lysozyme as described in example 1, (with detection of bound antibody with anti-human CH3 γ4 from Serotech) and BIAcore as described in example 1, only the antibody with the 15 amino acid spacer retained specificity for 2-phenyloxazol-5-one and lysozyme.

Analysis by FPLC gel filtration using Superdex75, and detection of binding using the BIACore (as described in example 1) indicated that about 30% of the material was dimeric. Thus a larger fragment can indeed be made in this way. The 30% dimer in this CH3 fusion contrasts with the 100% dimer with the parent NQ11/D1.3 zero linker diabody, indicating that the presence of the CH3 domain perturbs the equilibrium of dimerisation of this diabody.

Example 13

Diabody Mediated Lysis of Human Tumour Cells by Human PBL

Bispecific antibodies that bind to tumour cells via a tumour specific marker and bind to human effector cells via receptors such as CD16 can mediate lysis of tumour cells by the human effector cells (see, for example, Garcia de Palazzo I. et al., Antitumour effects of a bispecific antibody targeting CA19-9 antigen and CD16, Cancer Research 52, pp5713–5719).

A bispecific diabody (CBM-1) was constructed using the variable regions derived from the murine anti-CEA antibody which binds the tumour specific antigen carcinoembryonic antigen (CEA) and the monoclonal antibody 3G8 (Flcit, H. B., Wright, S. D., and Unkeless, J. C. (1982) Proc. Natl.

Acad. Sci. USA. 79, p3275–3279) which binds human cell surface protein CD16. CBM-1 was constructed using the techniques described in this patent application using the scheme outlined in FIG. 32, has a five amino acid linker between the variable domains and binds both CEA and CD16. CBM-1 was shown to bind to purified CEA and CD16 by ELISA.

Cell killing was determined by percent lysis (% lysis) assayed using a Chromium 51 release assay (Brunner K. T., Engers H. D. and Cerottini J. C. (1976), The $^{51}$Cr release assay as used for the quantitative measurement of cell mediated cytolysis in vitro; in: Bloom B. and David J. R (eds), In vitro methods in cell mediated and Tumor immunity, p423. Academic Press New York).

Effector cells (peripheral blood lymphocytes (PBL)) were obtained from human donors and were isolated from whole blood using Ficoll-Isopaque (Ficoll-Paque, Pharmacia, Uppsala, Sweden) density centrifugation according to the protocol of Boyum, A (1968) Scan. J. Clin. Lab. Invest. 21 (suppl. 97), p7.

$2 \times 10^6$ LS 174T target cells bearing CEA (ATCC CL 188, U.S. Pat. No. 4,288,236) are harvested after trypsinisation and washed with RPMI containing 10% fetal calf serum. After centrifugation of the cells the pellet is labelled with $^{51}$Cr (200 $\mu$Ci) for 1 hour at 37° C. After 2 washes in RPMI, target cells are added to microplates (5000 cells per well) along with effector cells to give various effector:target ratios. The diabody (up to 1 mg/ml) is added in 200 $\mu$l before incubation for 4 hours at 37° C. The cells are spun and half the supernatant (100 $\mu$l) is collected and chromium release is determined in a gamma counter. Each sample point is done in triplicate and the percentage of specific lysis is calculated as:

100×(Mean sample release−spontaneous release)/(maximum release−spontaneous release)

Spontaneous release is measured from target cells in assay medium alone and maximum release is measured after lysis of an equivalent number of target cells in 1M HCl.

FIG. 31 shows the data from an experiment using PBL from donor D at various ratios of PBL effector cells to LS174T tumour cell target. The data show CBM-1 mediates cell lysis with increasing effector cells when 1000 ng/ml diabody was used but not when 10 ng/ml diabody was used. Thus CBM-1 mediates killing of the tumour target cell and cell killing is dependent on the dose of the CBM-1 diabody used.

This experiment demonstrates that a bispecific diabody can mediate the killing of one cell (the tumour cell) by another (the CD16 positive cells contained in human PBL).

Example 14

Construction of a Repertoire of Bispecific Diabodies Displayed on Phage

We describe here the 2-step construction, and display on bacteriophage of a diabody repertoire and selection of bispecific diabodies with specificity for two haptens, 2-phenyl-oxazol-5-one (phOx) on one arm, and digoxin (Dig) on the other arm. Although many different methods can be used to construct biospecific repertoires here we have pursued route C of FIG. 7 (see introduction).

First, two scFv repertoires were assembled using V-genes obtained from the spleens of immunised mice. These repertoires were displayed on phage, and selected on antigen to enrich for binders. In a second cloning step, the V-genes were reshuffled to form a bispecific diabody repertoire, the repertoire displayed on phage and sequentially selected on the two antigens (phOx-Bovine Serum Albumin (BSA) and Digoxigenin-BSA).

All the amplification reactions described in this section, unless otherwise stated, use the basic cycling protocol: 94° C. for 1 min., 55° C. for 1 min. and 72° C. for 2 min. for 25 cycles, with Taq polymerase purchased from Cetus or Boehringer Mannheim, and the buffer composition as described by the supplier.

Construction of the Two Building Blocks: Diverse scFv Repertoires of Anti-digoxin and Anti-phOx Activities.

A highly diverse repertoire of antibodies from the spleen cells of immunised mice was made essentially as described in Clackson et al., Nature 352, 624–628 (1991). Two haptens were chosen, Digoxin and the phOx. Groups of three mice were immunised with antigen (either Dig-Chicken Serum Albumin (CSA) or phOx-CSA). The immune response to the antigen was monitored by standard ELISA with coated antigen (phOx-BSA or Dig-BSA). While a good phOx response could be elicited in Balb/C mice(antibody titres of $10^{-5}$), it was necessary to use A/J mice in order to achieve satisfactory anti-digoxin titres ($10^{-5}$ or better). Also, in order to explore the potential variation in antibodies produced during the primary and secondary response, three mice immunised with phOx-CSA, were splenectomised four weeks earlier than the remaining three mice immunised with the same antigen. Once a suitable response had been achieved, a secondary immunization was performed with antigen only (phOx and Dig), followed by removal of the spleen 3 days later.

Single cell suspensions were prepared from each hyperimmunised spleen and pooled, after which RNA was prepared using the RNAzol B system (Biogenesis limited, Bournemouth, UK). RNA isolated in this manner was used without further modification to prepare first strand cDNA, and, from this, primary VH and VL bands (as in Clackson et al., 1991, supra). The amplified VH and VL DNAs were assembled as scFv genes in a PCR driven process, using primers tagged with restriction sites for cloning. PCR assembly was used to join the VH and VL genes via a fragment encoding a 15 amino acid linker in a standard scFv format (using a (Gly$_4$Ser)$_3$ (SEQ ID NO: 98) sequence). Following restriction with SfiI and NotI, the assembled fragment was ligated into an appropriately cut phagemid vector pCANTAB5myc, and the repertoire electroporated into E. coli. The Dig-repertoire was made in a similar way, with slightly different primers to include an additional cloning site for further work (and changing the linker sequence to (Gly$_4$Ser)$_2$ Gly$_2$Ser$_2$ (SEQ ID NO: 101)). (Note: the only difference is that the linker sequence was made with LINK-FOR-XHO (SEQ ID NO: 67) and the standard.LINK-BACK primer; the LINK-FOR-XHO (SEQ ID NO: 67) sequence introduces a XhoI site for later cloning.).

We were able to produce library sizes of $1 \times 10^6$ and $7 \times 10^6$ independent clones for the primary and secondary phOx responses respectively and of $3 \times 10^6$ for the digoxigenin. Diversity was confirmed by a BstNI digest of the scFv DNA, showing many different patterns (not shown). Having pooled the two phOx libraries, enrichment for phOx and Dig binders was achieved by several rounds of panning on highly derivatised phOx-BSA (14:1 molar ratio) and Dig-BSA (25:1 molar ration) respectively. To retain all possible binders, we used a very high antigen concentration for coating onto Immunotubes used in the panning selection (1 mg/ml). After one and two rounds of panning, 66% and 94% of all clones from the phOx library bind to phOx-BSA respectively and not to BSA (not shown). Similarly, digoxigenin binders are abundant (90%) after two rounds of selection. A wide variety of ELISA signals is seen after one round of selection, becoming more homogenous and higher over further rounds. As building blocks for the bispecific diabody repertoire, DNA from the anti-phOx repertoire of round one (E1-OX ds-DNA; 66% positives) and the anti-Dig repertoire of round two (E2-DIG ds-DNA; 90% positives) were chosen.

Construction of a Bispecific Repertoire.

Figure 33:
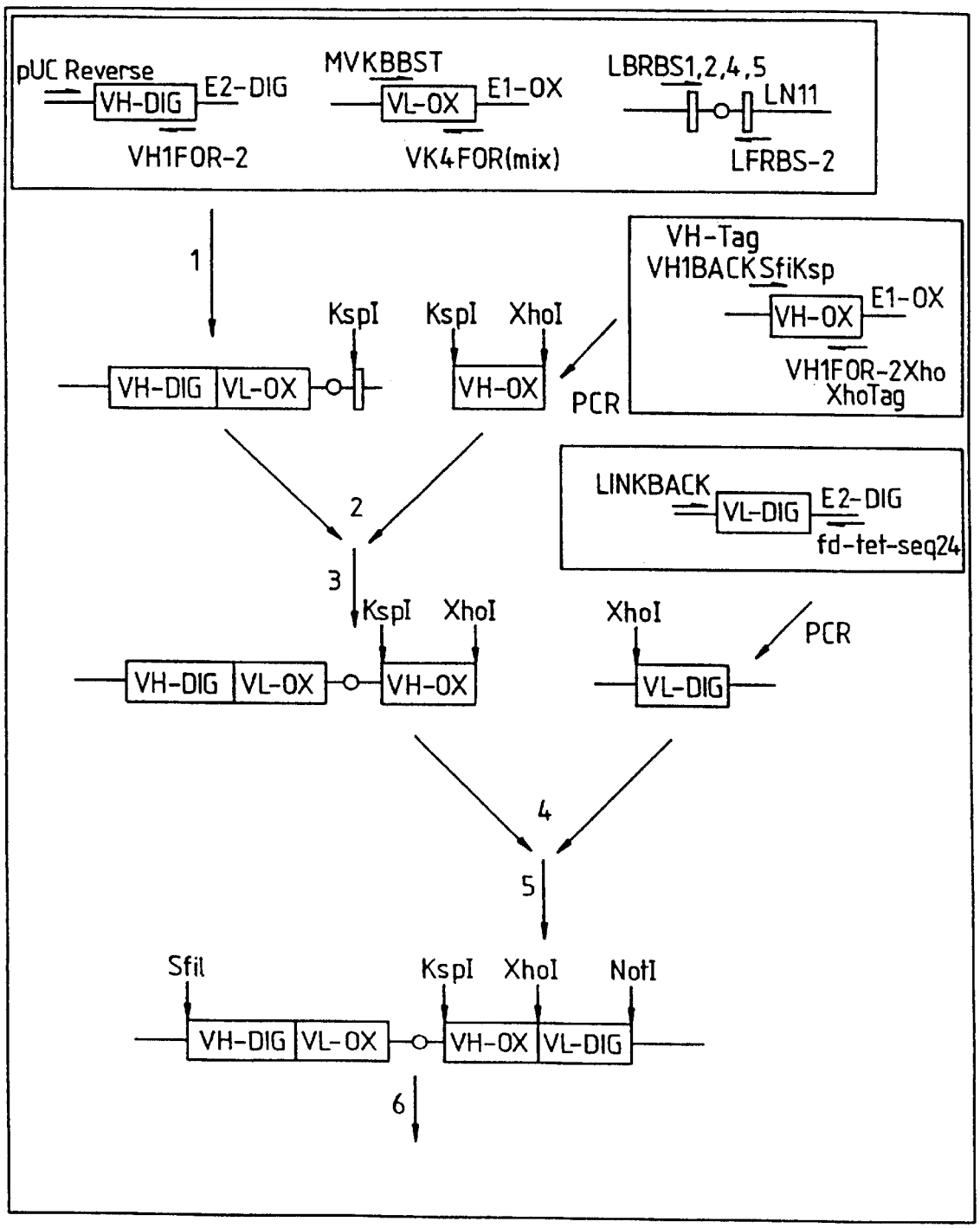

An overview of the cloning scheme is given in FIG. 33. The first VH-VL combination was made by a splice overlap extension PCR reaction. The selected VL-DIG repertoire and selected VH-OX repertoire were spliced together with a DNA fragment encoding two stop codons, a ribosome binding site and signal sequence as follows. The VH-DIG repertoire was amplified from E2-DIG ds-DNA using the primers pUCReverse (SEQ ID NO: 68) and VH1FOR-2. The VL-OX repertoire was amplified from E1-OX ds-DNA using the primers MVKBBST (SEQ ID NO: 69) and VK4FOR (Clackson et al., 1990, supra). The MVKBBST primer (SEQ ID NO: 69) was designed to contain 5' sequence complementary to VH1FOR-2 and hence the VH gene 3' sequence. The third fragment, called the RBS fragment, was amplified from ds-DNA from phagemid pCANTAB5-Fab D1.3 (clone LN11), to supply the sequence for between the two VH-VL cassetttes. The sequence of the amplified template is: 5'-TAA TAA CCC TGC AGG TCG ACA AGG AGA CAG TCA GTG AAA AAA CTC CTC TTT GCC ATA CCA CTC GTG GTG CCA TTT TAC TCC GCG GCT GCC CAA CCA GCG ATG GCC-3' (SEQ ID NO: 102). The template was amplified using a reverse primer mix (LBRBS-1,2,4,5 (SEQ ID NOS: 70–73, respectively)) designed to contain sequence region complementary to VL gene 3' sequences, and a forward primer, LFRBS-2, (SEQ ID NO: 74) which was adapted to contain no sequence complementarity with VH genes to avoid forming unwanted assembly products with the linker situated anywhere other than 3' of the VL-OX. The three fragments, VH-DIG, VL-OX and the LN11-derived fragment, were assembled by a splice overlap extension using PCR and oligonucleotides pUCReverse and LFRBS-2. The VH-DIG/VL-OX-RBS fragment was gel-purified and used in the next step.

In a second step, the VH-OX repertoire was amplified from E1-OX ds-DNA using primer VH1BACKSfiKsp (SEQ ID NO: 75) and VH1FOR-2Xho (SEQ ID NO: 76). The first primer was designed around the standard VH1BACK primer (Clackson et al., 1990, supra), but contains a long 5' tag containing a KspI site. The forward primer (VH1FOR-2Xho (SEQ ID NO: 76)) was again based on the standard VH1FOR-2 (Clackson et al., 1991, supra), but now contains a XhoI cloning site. The amplified product was gel-purified and re-amplified using the primers VH-Tag and Xho-Tag (SEQ ID NOS: 77 & 78, respectively), and the VH-OX fragment gel-purified.

The assembled VH-DIG/VL-OX-RBS product and the VH-OX were subsequently cut with KspI (present in the 5' tag of the VH-OX and within the leader sequence at the 3' end of the RBS fragment), and ligated together using T4 DNA ligase using a ligation kit (Amersham). A sample of the ligation mixture was used directly in a PCR to pull-through the ligated product, using primers pUCReverse (SEQ ID NO: 68) and XhoTag (SEQ ID NO: 78). This fragment, VH-DIG/VL-OX-RBS-VH-OX, was gel-purified, cut with XhoI and gel-purified again, to prepare it for the last step, the addition of the VL-DIG repertoire.

The last V-gene repertoire, VL-DIG, was obtained by PCR from E2-DIG ds-DNA by PCR with primers LINKBACK (Clackson et al., 1991, supra) and fd-tet-seq24 (SEQ ID NO: 13). The fragment was gel-purified, cut with XhoI and gel-purified. The VL-DIG DNA was ligated to the VH-DIG/VL-OX-RBS-VH-OX DNA, and a sample of the ligation mixture used directly in a PCR to pull-through the ligated product, using primers BioGene3Lead and fd-tet-seq24 (SEQ ID NOS: 79 & 13, respectively). This fragment, now containing the two assembled VH-VL gene cassettes, was gel-purified, cut with SfiI and NotI, gel-purified, ligated into phagemid vector pCANTAB5myc (FIG. 19) (restricted with the same enzymes), and introduced by electroporation in E. coli TG1.

The first cloning resulted in a repertoire of 50000 clones, with 95% of the clones with a full bispecific diabody insert, and with retained diversity as judged by BstNI fingerprinting (not shown).

Phage particles were prepared from the repertoire, basically as described in Marks et al., J. Mol. Biol., 222, 581–697, 1991. The only difference in the rescue procedure was the growth temperature of the culture after the infection with helper phage. Instead of 30° C., a lower temperature was used (22° C.). Phage was prepared from the culture supernatant after an overnight (20 hours) incubation by two PEG precipitations. Titres were similar to those obtained from scFv repertoires displayed on phage (appr. $10^{12}$ colony forming units per ml culture supernatant). Phage was used for selection on phOx-BSA (by panning, as described earlier), and binding phage reinfected into TG1. Individual clones before and after this selection were analysed by ELISA for binding to phOx-BSA, Dig-BSA and BSA. Diabodies were analysed both as phage-diabodies (diabodies displayed on phage after rescue of individual clones with helper phage) and as soluble diabodies (using supernatant of cultures induced with 1 mM IPTG and grown for 20 hours at 22° C.). FIG. 34 shows the ELISA results, in gray scale for simplicity; an ELISA OD of <0.2 was taken as a cut-off for evidence of binding; all the wells with a gray signal are therefore considered positive. Plates 1, 4 and 7 correspond to the ELISA analysis (on Dig-BSA, phOx-BSA and BSA respectively) of 96 clones of the unselected repertoire as diabodies displayed on phage (supernatant containing phage from the same clone was analysed in each of the three ELISAs). The repertoire selected on phOx-BSA was analysed both as diabodies displayed on phage (plates 2, 5 and 8) and as soluble diabodies (plates 3, 6 and 9). First, the phage ELISA's are discussed. FIG. 34 shows that, before any selection, the repertoire contains binders to Dig only (wells A7, C7, etc.), phOx only (wells G2, H4, F11), but also to both (wells A3, A6, B9, C5, D12, H12). The starting repertoires for this bispecific repertoire had 66% phOx-binders and 90% Dig-binders. After the recloning, we obtain 9/96 (9.3%) phOx-binders and 14/96 (14.5%) Dig-binders. So, although all V-gene repertoires have been shuffled during the recloning, and despite the fact that some of the V-gene repertoires have been taken through appr. 100 cycles of PCR, we obtain a relatively high level of binders in our bispecific repertoire. The indication is also that most antibodies which bind to antigen in the scFv format, must also be able to function in the bispecific diabody format. Since 6/96 clones bind to both antigens, it is likely that the original repertoire of 50000 clones will have more than 3000 bispecific antibodies.

Enrichment on phOx-BSA gave us appr. 40/96 bispecific antibodies, with 17 clones binding to phOx only, and 9 to Dig only. Clearly, the phOx selection resulted in an increase of the frequency of phOx-binders (from 9/96 to 57/96), and, as expected, a decrease of the number of Dig only binders (14/96 down to 9/96). This selection proves that diabodies can be selected from repertoires using the standard phage format.

FIG. 35 shows a sample of the ELISA signals for binding to Dig and phOx for some of the selected bispecific clones, as phage diabodies (top) of soluble fragments (bottom). Some clones have similar ELISA signals for both Dig and phOx, while others are completely different in their binding behaviour. From these results it is clear that we have selected a whole series of different bispecific antibodies, and not just one clone, which could be confirmed by BstNI fingerprint analysis (results not shown).

The ELISA of soluble diabody fragments indicates the same trend as the phage diabody ELISA. Plates 3, 6 and 9 are ELISA's with soluble diabodies obtained from the same clones from which the phage diabodies were analysed (plates 2, 5 and 8; FIG. 34). The frequency of positives is clearly lower, possibly due to the lower sensitivity of the ELISA, or the variable amounts of diabody produced. However, the soluble diabody ELISA results are completely consistent with the phage ELISA. For example, the clone in well B8 of plates 3 and 6 is bispecific as a soluble diabody, but also when displayed on phage (well B8 on plates 2 and 3). Similarly, the clone in well 32 is Dig specific both as soluble and phage diabody.

To prove further that these clones are bispecific, 4 clones (from wells G9, F12, H4 and F2) were analysed as soluble fragments and phage diabodies in an agglutination assay. Red blood cells were coated with either Dig-BSA or phOx-BSA, cells mixed and incubated with periplasmic extract or culture supernatant (for the soluble diabody) or culture supernatant (for the phage diabody), basically as described in Example 9. Agglutination was clear in all expected cases (and stronger for periplasmic extracts than for culture supernatant) for all 4 clones (results not shown).

These results show that bispecific (and therefore most likely also bivalent) diabody repertoires can be generated, displayed on phage, and selected with antigen.

Example 15

Construction and Expression of Diabody with VL Domain N-terminal to the VH Domain: Bivalent Diabody Directed Against 2-Phenyloxazol-5-one In the usual diabody format the heavy chain variable domain is N-terminal to the light chain variable domain (N-(VH-VL)-C). This example describes the construction of a diabody in which the orientation of the light chain and heavy chain variable domains has been reversed (VL-VH) ("reverse" diabody). This results in the apposition of the two VL domains, rather than the two VH domains.

Construction of Bivalent NQ11 Reverse Diabody

An NQ11 scFv clone in the vector fd-CAT1 (J McCafferty et al 1990 supra) was used as the substrate for amplification of the VL and VH domains. Primers were designed such that the amplification products could be digested with the restriction enzyme Xho1 and ligated to provide DNA encoding a reverse diabody construct for SfiI and NotI digestion and cloning into the phagemid vector pCANTAB5-myc. The primers SfiVLBack (table 1 (SEQ ID NO: 62)) and fdtseql (SEQ ID NO: 28) were used to amplify the VL domain and the primers VL/VHBackXho1 (SEQ ID NO: 64) or VL/VHBackXho1A (SEQ ID NO: 65) were used with VHForNot (SEQ ID NO: 63) for the amplification of the VH domain.

SfiVLBack (SEQ ID NO: 62) consists of a sequence which is complementary to the 5' terminus of NQ11 VL followed by a 33 base overhang containing a SfiI restriction site. Fdtseql (SEQ ID NO: 28) binds to a region within the geneIII coding sequence that lies 3' to the VL sequence. The amplified VL domain contains a pre-existing Xho1 site within 10 bp of the 3' terminus and the primer-introduced SfiI site at the 5' terminus.

VHForNot (SEQ ID NO: 63) consists of a sequence which is complementary to the 3' terminus of the NQ11 VH followed by a 24 base overhang containing a NotI restriction site. VL/VHBackXho1 (SEQ ID NO: 64) consists of a sequence which is complementary to the 5' terminus of the NQ11 VH DNA and a sequence complementary to the 3' terminus of the NQ11 VL DNA which includes the Xho1 restriction site. VL/VHBackXho1A (SEQ ID NO: 65) is similar to VL/VHBackXho1 (SEQ ID NO: 64) but contains two extra glycine codons at the join between the VH and VL sequences.

The amplification products were digested with Xho1 and gel purified. The fragments were ligated and the ligation product used as template for a pullthrough amplification using the flanking primers SfiVLBack and Fdtseql (SEQ ID NOS: 62 & 28, respectively) Where VL/VHBackXho1 (SEQ ID NO: 64) was used in the primary PCR the pullthrough product generated a reverse diabody with no linker residues. Where the VL/VHBackXho1A (SEQ ID NO: 65) primer was used the pullthrough product generated a reverse diabody with a linker of two glycine residues.

The pullthrough products were digested with SfiI and NotI and ligated to SfiI/NotI digested vector, pCANTAB5-myc. The purified constructs were electroporated into electrocompetent E. coli TG1 cells and plated onto 2TY/agar plates containing 2% glucose, 100 $\mu$g/mL ampicillin.

Soluble diabody was expressed by growing the resulting colonies to log phase at 30° C. in 2TY, 0.1% glucose, 100 $\mu$g/mL ampicillin. IPTG was added to 1 mM and the cells were incubated for 24 hours at 22° C. The cells were centrifuged (1000 g, 10 minutes) and the supernatant used in ELISA.

80 $\mu$L of supernatant was added to 20 mL 5×PBS, 10% Marvel in ELISA wells coated with a 2-phenyloxazol-5-one/BSA conjugate (100 $\mu$g/mL in PBS) and blocked with 2% Marvel/PBS. A standard ELISA protocol was followed (H R Hoogenboom et al. 1991, Nucl. Acids Res. 19, 4133–4137) using detection of the myc-tag with the monoclonal antibody 9E10, and horseradish peroxidase-conjugated anti mouse IgG. Binding by both the 0-linker and 2 residue-linker NQ11 reverse diabodies was detected (FIG. 36).

To confirm that the reverse diabodies were bivalent a haemagglutination assay was conducted on periplasmic extracts prepared 4 hours post induction. Cells were grown in 5 mL cultures, induced as above and grown at 22° C. for 4 hours. The cells were centrifuged and pellets were resuspended in 250 $\mu$L PBS, 1 mM EDTA. Following 15 minutes incubation on ice the cells were centrifuged and the periplasmic supernatant used in the agglutination assay. 50 $\mu$L of periplasmic supernatant was incubated with 50 $\mu$L of sheep red blood cells derivatized with a 2-phenyloxazol-5-one/BSA conjugate (derivatization was accomplished by incubating red blood cells with 2-phenyloxazol-5-one/BSA at 20 mg/mL in PBS and 1 Ethyl-3-(3-dimethylaminopropyl) carbamide at 100 mg/mL in PBS for 1.5 hours at 4° C.).

Neat periplasmic supernatants from both 0-linker and 2 residue-linker reverse diabodies agglutinated the derivatized red blood cells but did not agglutinate non-derivatized cells. This shows that diabodies in which the orientation of V domains is reversed can fold to form stable and active bivalent binding proteins.

The DNA encoding the bivalent phOx-specific reverse diabody may be used in the construction of a bispecific diabody in the reverse format with one arm directed against phOx and the other arm directed against NIP. This is achieved by inserting DNA encoding VH NIP—intergenic region—VL NIP into the bivalent NQ11 clone, thus producing two polypeptide chains would thus be produced, VL Ox/VH NIP and VL NIP/VH Ox. The intergenic region contains a ribosome binding site and a leader sequence for the second polypeptide (VL NIP/VH Ox).

Example 16

Evidence That a Ten Amino Acid Linker Between VH and VL Domains May Allow Monomer Formation A 10 amino acid linker version of single chain Fv NQ11 was prepared as described for the generation of construct I in example 1. In example 1, the 5 and 15 amino acid versions of this diabody were made. In this example the diabody constructs are completed by the generation of a 10 amino acid linker diabody using primer 5 to introduce the linker.

The clone was expressed in TG1 and fragments were purified using chromatography on phOx-BSA-Sepharose as in example 1.

The purified protein was analysed by FPLC gel filtration using a Superdex column followed by analysis of binding to phOx-BSA using the Pharmacia BIACore. The 10 amino acid linker NQ11 diabody had an apparent molecular weight identical to that of FvNQ11 and the 15 amino-acid linker scFvNQ11 but smaller than that of the 5 amino acid linker NQ11 molecule which forms a diabody. Thus it appears that a 10 residue linker may be sufficiently long to allow pairing between VH and VL domains from the same chain. However, the precise size of linker allowing monomer formation is also likely to depend on the sequence of the linker. For example, we predict that it would be more difficult go form monomers with such short linkers if there were a sequence of bulky side chains (such as Tyr) in the linker.

Example 17

Preparation of Bispecific Anti-NIP, Anti-HumanFcR1 Diabody

A bispecific diabody directed against NIP (4-hydroxy-3-iodo-5-nitrophenylacetic acid) and the human FcγR1 receptor with a zero amino acid linker was prepared with a bivalent anti-FcγR1 diabody being prepared as an intermediate.

Construction of Bivalent Anti-FcγRI Diabody 022 is a murine monoclonal antibody that binds specifically to human FcγRI. It has been cloned in a diabody format using a 5 residue linker in the orientation VH-GGGGS-VL in the phagemid vector pUC119SfiNotmyc. The linker sequence was incorporated into the primer (Vk022SacbaLink5BstEII (SEQ ID NO: 35)) used to amplify the 5' end of VK and this primer also introduces a SacI restriction site at the beginning of Vk. A restriction site for BstEII was incorporated 5' of the linker sequence of primer Vk022SacbaLink5BstEII (SEQ ID NO: 35) and also at the 3' end of VH1FOR-2 (E. S. Ward et al 1989 supra). A SfiI restriction site is introduced in the primer VH022Sfiba used to amplify 5' end of VH. A NotI restriction site is introduced in the primer Vk022foNot (SEQ ID NO: 36) used to amplify 3' end of VK. This would allow the VH and linker-VL fragments to be cloned in a 3-way ligation reaction into the expression vector pUC119SfiNotmyc.

The VH022 gene was amplified by PCR with the primers VH022baSfi (SEQ ID NO: 32) and VH1fo-2. The Vk022 gene was amplified with the primers Vk022SacbaLink5BstEII and Vk022foNot (SEQ ID NOS: 35 & 36, respectively). Standard conditions were used with M13 phage encoding the 022 VH and VL genes (supplied by Scotgen) as template. The product of the VH PCR reaction was digested with restriction enzymes SfiI and BstEII, and the product of the VL PCR reaction was digested wish restriction enzymes NotI and BstEII. The VH and the VL domain DNA was ligated into SfiI/NotI digested pUC119SfiNotmyc and pCantab6 in a molar ratio 3:3:1 (VH:VL:pUC119SfiNotmyc) and the resulting ligation mix used to transform E. coli TG1 cells. Recombinants were screened for inserts of correct size using 022 specific primers VH022baSfi and Vk022foNot (SEQ ID NOS: 32 & 36, respectively). The VH and VL domain DNA was also ligated into SfiI/NotI digested pCANTAB6 vector in the same way and used to transform E. coli HB2151 cells.

Soluble diabody was expressed from the pUC119SfiNotmyc clones in TG1 by growth at 37° C. Cells in log phase growth in 2 mL 2YT/0.1% glucose/100 mg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in ELISA.

For the ELISA, assay plates were coated with a 1 in 500 dilution of a goat anti-human IgM (SeraLab) in carbonate buffer at 37° C. for 4 hours. The wells were blocked with PBS/1% BSA and 100 μl Cos supernatant containing human Fcgamma RI-IgM fusion added (diluted 1 in 4 into 1%BSA/PBS) and incubated at 37° C. for 1 hour. Diabody supernatants prepared as above were added in 200 μl with ×2 dilutions thereof. Additionally, each well contained 10 μg (10 μl) of human IgG1, λ (Sigma). Incubation was at 37° C. for 1 hour. Binding was detected using horse radish peroxidase labelled goat anti-human kappa antibodies (Sera-Lab) at 37° C. for 1 hour and developed with OPD substrate. ELISA signals of greater than 1.0 were obtained at 492 nm with concentrated supernatant samples.

Construction of Bispecific Anti-NIP, Anti-FcγRI Diabody 022/B18/0

This diabody was constructed in a manner similar to that used for the diabody NQ11/B1.8 in example 3. The diabody 022/5 (see above) was cut with BstEII and SacI to give a vector construct with VH022 and VL022 arms. The VL and VH sequences of the antibody B1.8 were then cloned into this to give a bispecific diabody 022/B18/0.

The two antibody specificities 022 (anti-human FcγRI) and B1.8 (anti-NIP) were combined in the bispecific diabody format fusing the VH and VL directly with 0 linker in the orientation VH-VL in the phagemid vector pUC119SfiNotmyc. The linker sequence was incorporated into the primer (V1B1.8baLink0BstE (SEQ ID NO: 33)) used to amplify the 5' end of V1. A restriction site for BstEII was incorporated 5' of the linker sequence of primer V1B1.8baLink0BstE (SEQ ID NO: 33). An AscI restriction site is introduced in the primer V1B1.8foAsc (SEQ ID NO: 34) used to amplify 3' end of VK. This would allow the VH-linker and linker-VL fragments to be cloned in a 3-way ligation reaction into the expression vector pUC119SfiNotmyc.

VHB1.8 was amplified with primers 2 and 6 (SEQ ID NOS: 2 & 6, respectively) (example 1), the V1B1.8 was amplified with the primers V1B1.8baLink0BstE and V1B1.8foAsc (SEQ ID NOS: 33 & 34, respectively) both from scFvB1.8 cloned into fdDOG-1 (supplied by R. Hawkins). The product of the VH PCR reaction was digested with restriction enzymes AscI and SacI, and the product of the VL PCR reaction was digested with restriction enzymes AscI and BstEII. A vector fragment of diabody 022/5 (see above) was cut with BstEII/SacI and the VH and the VL domain DNA were simultaneously ligated with it in a molar ratio 3:3:1 (VH:VL:pUC119-022/5) The resulting ligation mix used to transform E. coli TG1 cells. Recombinants were screened for inserts of correct size using primers LMB2 and LMB3 to PCR amplify inserts from recombinants.

Soluble diabody was expressed by growth at 37° C. Cells in log phase growth in 2 mL 2YT/0.1% glucose/100 μg mL$^{-1}$ ampicillin were induced by adding IPTG to a final concentration of 1mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in ELISA for binding to the human FcγRI receptor as above and for binding to NIP-BSA as follows.

50 mL periplasmic supernatant+50 mL 4% marvel/PBS was added to ELISA wells coated with NIP-BSA (BSA derivatized with 10 to 12 molecules of NIP) (10 μg mL$^{-1}$ in PBS), blocked with 2% marvel/PBS. A standard ELISA protocol was followed (H. R. Hoogenboom et al., Nucl. Acids Res. 19, 4133–4137 1991) using detection of the myc-tag with the monoclonal antibody 9E10, and horseradish peroxidase conjugated anti mouse IgG. ELISA readings were greter than 1.0 after 10 min for both antigens.

For purification on a NP-sepharose affinity column (T. Simon, Ph.D. thesis, University of Koln, 1990) expression was performed as above except after induction the cells were grown for 26 h at 22° C. Subsequently the cells were pelleted at 8000 rpm/10'/4° C. and the culture supernatant was filtered using a 0.16μ FILTRON Minisette to remove any remaining cells and then concentrated using a FILTRON Minisette. The concentrate was passed twice over a NP-sepharose column. The column was washed with 20 column volumes of PBS and 10 column volumes of PBS/0.5M NaCl. Bound protein was eluted with 0.2M Glycine pH2.3 at 4° C. and Immediately neutralized with 1M Tris pH7.4, then dialysed into PBS/0.2 mM EDTA pH7.4 and frozen in aliquots.

The purified protein bound strongly and specifically to both NIP and HuFcγRIreceptor as determined by ELISA assays showing the-bispecific nature of the protein product.

Example 18

Preparation of Bispecific Anti-idiotype (bcl1)-antiCD3 Diabody

A clone was prepared encoding a bispecific diabody with a 5 amino acid linker, with one arm expressing an anti-idiotype antibody B1 directed to the surface Ig of the BCL-1 lymphoma cell line, and the other arm, directed against the mouse T-cell receptor cluster differentiation antigen CD3, derived from the hamster hybridoma cell line 2C11. As an intermediate step the bivalent diabody 2C11 was prepared. Both the bivalent and bispecific diabodies were shown to bind CD3 by FACS scanning on EL-4 mouse T cell line.

The construction of the bivalent diabody B1 with a 5 amino acid linker is described in example 19.

2C11 is a hamster monoclonal antibody that binds to mouse CD3 T-cell coreceptor. It has been cloned in a diabody format using a 5 residue linker in the orientation VH-GGGGS-VL in the phagemid vector pUC119SfiNotmyc. The linker sequence was incorporated into the primer (VkCbaLink5BstEII (SEQ ID NO: 44)) used to amplify the 5' end of VK. A restriction site for BstEII was incorporated 5' of the linker sequence of primer VkCbaLink5BstEII (SEQ ID NO: 44) and also at the 3' end of VH1FOR-2 A SfiI restriction site was introduced in the primer VH2C11Sfiba used to amplify 5' end of VH. A NotI restriction site was introduced in the primer mix Vk4FORNot (Clackson, 1991 supra.) used to amplify 3' end of VK. This allowed the VH and linker-VL fragments to be cloned in a 3-way ligation reaction into the expression vector pUC119SfiNotmyc.

RNA was extracted from 2C11 hybridoma cells (supplied by Prof. Kris Thielemans) and used to prepare cDNA. 2C11 VH and VL domain DNA was amplified by PCR from cDNA using primers pairs VH2cbaSfi and VH1FOR-2, and VkCba and Vk4FOR (T. Clackson, H. R. Hoogenboom, A. D. Griffiths and G. Winter, Nature 352, 624–628 1991) respectively using standard conditions. (Note: since the 2C11 V-genes had been cloned and sequenced previously, we designed a 2C11-VH specific primer rather than use the "standard" VH1BACK primer (R. Orlandi, D. H. Gussow, P. T. Jones and G. Winter, Proc. Natl. Acad. Sci. USA 86, 3833–3837 1989)).

The VH2C11 was reamplified with the primers VH2C11baSfi (SEQ ID NO: 37), VH1FOR2, the Vk2C11 was amplified with the primers Vk2C11baLink5BstEII (SEQ ID NO: 38), Vk4FORNot. The product of the VH PCR reaction was digested with restriction enzymes SfiI and BstEII, and the product of the VL PCR reaction was digested with restriction enzymes NotI and BstEII. The VH and the VL domain DNA was simultaneously ligated into SfiI/NotI digested pUC119SfiNotmyc in a molar ratio 3:3:1 (VH:VL:pUC119SfiNotmyc) and the resulting ligation mix used to transform E. coli TG1 cells. Similarly, the VH and VL domain DNA was ligated into SfiI/NotI digested pCANTAB6 and transformed into E. coli HB2151 cells in the same way. Recombinants were screened for inserts of correct size using 2C11 specific primer VH2C11baSfi (SEQ ID NO: 37) and LMB3 (SEQ ID NO: 85) or VH2C11baSfi (SEQ ID NO: 37) and fdSeq for recombinants in pUC119SfiNotmyc or pCANTAB6 respectively.

Soluble diabody was expressed by growth at 37° C. Cells in log phase growth in 2 mL 2YT/0.1% glucose/100 μg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in FACSScan using mouse T-cell lines EL-4 and MD90 (which express the CD3 antigen). The diabody showed the same specificity as the parent diabody for these cell lines.

The FACS scanning was performed as follows: The cell lines EL-4 and MD-90 (G. Gross et al. Proc. Natl. Acad. Sci USA 86 10024–10028 1989) were grown in standard tissue culture conditions. About 10$^7$ cells were harvested and washed twice with PBS/1%BSA/0.05NaN$_3$ and then distributed in aliquots of at least 10$^5$ cells in wells of a Cellwell plate. The 2C11/5 bivalent anti-CD3 diabody was added to give a final volume of 100 μl and allowed to bind for 30 min to 1 hour at 4° C. Cells were then pelleted by centrifugation at 1600 rpm for 2 min and supernatant was removed by aspiration. Cells were then resuspended in 100 μl of Mab9E10 (diluted 1 in 100) in PBS/1%BSA/0.05%NaN$_3$ and allowed to bind for 30 min at 4° C. Cells were then pelleted by centrifugation at 1600 rpm for 2 min and supernatant was removed by aspiration. Cells were resuspended in 100 μl of Fab'2 anti-mouse FITC labelled (dilution 1:128 from Sigma) in PBS/1%BSA/0.05%NaN$_3$ and allowed to bind for 30 min at 4° C. in the dark. Cells were then pelleted by centrifugation at 1600 rpm for 2 min and supernatant was removed by aspiration. Cells were then washed twice with 1 ml of PBS/l%BSA/0.05%NaN$_3$ and transferred to 5 ml Falcon tubes in a final volume of 1 ml and immediately analysed. Fluorescence activated cell sorting was performed with a Becton-Dickinson-FACSScan. The binding of the 2C11 anti-CD3 diabody with a 5 aminoacid linker to the EL-4 and MD-90 cells was detected by a shift in the cell population to a higher fluorescence reading compared to a control where cells are incubated with the 9E10 and Fab'2 anti-mouse FITC labelled reagents but no diabody. The scan was calibrated by comparison on the shift with the 2C11 diabody to the shift obtained with a commercial anti-mouse CD3 IgG labelled with FITC (Serotech). The two anti-CD3 reagents gave comparable shifts. Thus this 2C11/5 diabody binds efficiently to EL-4 and MD-90 cells.

Construction of Bispecific Anti-idiotype/anti-CD3 Diabody B1/2C11/5 with a 5 Amino Acid Linker The two antibody specificities B1 (anti-Id BCL-1) and 2C11 (anti-mouse CD3) were combined in the bispecific diabody format fusing the VH and VL with 5 linker in the orientation VH-GGGGS-VL in the phagemid vector pUC119SfiNotmyc. The linker sequence was incorporated into the primer (Vk2C11baLink5BstE (SEQ ID NO: 38)) used to amplify the 5' end of Vk. A restriction site for BstEII was incorporated 5' of the linker sequence of primer Vk2C11baLink0BstE. An AscI restriction site was introduced in the primer LinkAsc used to amplify the VH2C11 including the pelB leader and lacZ ribosome binding site. This allowed the VH-linker and linker-VL fragments to be cloned in a 3-way ligation reaction into the expression vector pUC119SfiNotmyc.

VH2C11 was amplified with primers LinkAsc and primer 5 (SEQ ID NO: 5)(as described in example 1), the Vk2C11 was amplified with the primers Vk2C11baLink5BstE (SEQ ID NO: 38), primer 1 (SEQ ID NO: 1)(as described in example1). The product of the VH PCR reaction was digested with restriction enzymes AscI and SacI, and the product of the VL PCR reaction was digested with restriction enzymes AscI and BstEII. A vector fragment of diabody B1/5 (see Example 19) was cut with BstEII/SacI and the VH and the VL domain DNA were simultaneously ligated with it in a molar ratio 3:3:1 (VH:VL:pUC119-B1/5). The resulting ligation mix used to transform E. coli TG1 cells. Recombinants were screened for inserts of correct size using primers LMB2 and LMB3 (SEQ ID NOS: 84 & 85, respectively).

Soluble diabody was expressed by growth at 37° C. Cells in log phase growth in 2 mL 2YT/0.1% glucose/100 mg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in FACSScan as described above and found to bind to EL-4 cells.

For purification on a Mab 9E10-sepharose column (for affinity purification via the myc tag) expression was performed as above except after induction the cells were grown for 26 h at 22° C. Subsequently the cells were pelleted at 8000 rpm/10'/4° C. and the culture supernatant was filtered and concentrated using a FILTRON Minisette (see example 17). Affinity purified protein eluted from the 9E10Sepharose column bound strongly and specificially to both Ig BCL-1 (as determined by ELISA using the methodology described in example 19 and by FACSScan on BCL cells) and mouse T-cells (as determined by FACSScan on mouse T-cell lines EL-4 and MD90).

Hence a functional bispecific anti-idiotype (bcl1)-antiCD3 diabody with a 5 amino acid linker has been prepared.

The activity of this diabody was tested in a model system for the stimulation (by cross-linking of the cells) of lysis of BCL-1 lymphoma in vitro using the MD90 cell line. BCL-1 lymphoma cells (supplied by Dr. Kris Thielemans) were used as target cells; as effector cells the cytotoxic T-cell hybridoma MD90 was chosen (supplied by Zelig Eshar).

Six million target cells were loaded with 150 mCi $^{51}$Cr (Amersham) for 1 hour at 37° C., and washed five times with PBS to remove unincorporated label. The cells were then mixed with effector cells in a ratio 20/1,10/1 and 5/1, and incubated for 8 hours at 37° C. in the presence (30 μg/ml) of absence of purified diabody. The amount of released $^{51}$Cr was determined by counting the gamma rays in the supernatant of the cultures.

For an effector:target ratio of 5:1, a 20% specific killing (as measured by release of $^{51}$Cr into the supernatant) of BCL-1 lymphoma cells by MD90 cells was obtained in the presence of diabody (with no specific killing in the absence of diabody), suggesting that the addition of diabody together with effector cells leads to killing of the target cells. The killing efficiency increases with decreasing effector/target ratio from little killing at 20:1 to 20% killing at 5:1 a pattern known to be typical for the MD90 cell line.

Example 19

Preparation and Characterisation of Bivalent Anti-idiotype (Anti-bcl1) Diabody

B1 is a murine monoclonal antibody that is an anti-idiotype to the surface Ig of the lymphoma BCL-1 (J. Brissinck et al J. Immunol. 147 4019–4026, 1991). It has been cloned in a diabody format using a 5 residue linker in the orientation VH-GGGGS-VL in the phagemid vector pUC119SfiNotmyc (Clackson, Nature). The linker sequence was incorporated into the primer (VlB1baLink5BstEII (SEQ ID NO: 42)) used to amplify the 5' end of VK and this primer also introduces a SacI restriction site at the beginning of VK. A restriction site for BstEII was incorporated 5' of the linker sequence of primer VlB1baLink5BstEII (SEQ ID NO: 42) and also at the 3' end of VH1B1FOR-2 A SfiI restriction site is introduced in the primer VHB1Sfiba used to amplify 5' end of VH. A NotI restriction site is introduced in the primer mix Vk4foNot (Clackson, Nature) used to amplify 3' end of VK. This would allow the VH and linker-VL fragments to be cloned in a 3-way ligation reaction into the expression vector pUC119SfiNotmyc.

The VHB1 was amplified with the primers VHB1baSfi (SEQ ID NO: 41), VH1B1fo-2, the VLB1 was amplified with the primers V1B1baLink5BstEII (SEQ ID NO: 42), Vk4foNot both from a scFv clone supplied by Prof. Kris Thielemans (Vrije Universiteit Brussel). The product of the VH PCR reaction was digested with restriction enzymes SfiI and BstEII, and the product of the VL PCR reaction was digested with restriction enzymes NotI and BstEII. The VH and the VL domain DNA was ligated into SfiI/NotI digested pUC119SfiNotmyc in a molar ratio 3:3:1

(VH:VL:pUC119SfiNotmyc) and the resulting ligation mix used to transform E. coli TG1 cells. The VH and the VL domain DNA was also ligated into pCANTAB6 FIG. 20 and the resulting ligation mix used to transform E. coli HB2151 cells. Recombinants were screened for inserts of correct size using B1 specific primers VHB1baSfi (SEQ ID NO: 41) and LMB2 (SEQ ID NO: 84) or VHB1baSfi (SEQ ID NO: 41) and fdseq for the pUC119SfiNotmyc and pCANTAB6 clones respectively.

Soluble diabody was expressed from the pUC119SfiNotmyc clone by growth at 37° C. Cells in log phase growth in 2 mL 2YT/0.1% glucose/100 μg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in ELISA using the protocol outlined below.

50 μL periplasmic supernatant+50 μL 3% BSA/PBS was added to ELISA wells coated with BCL-1 Ig (10 μg mL$^{-1}$ in PBS; Dr. Kris Thielemans) and blocked with 3% BSA/PBS. A standard ELISA protocol was followed (H. R. Hoogenboom et al., Nucl. Acids Res. 19, 4133–4137 1991) using detection of the myc-tag with the monoclonal antibody 9E10, and horseradish peroxidase conjugated anti mouse IgG. ELISA readings after 10 minutes were greater than 1.0.

The B1/5 diabody was purified by immobilized metal affinity chromatography (IMAC) from periplasmic preparations expressed from the pCANTAB6 clone using the manufacturer's protocol (Diagen). The material obtained bound to BCL-1 antigen on ELISA.

Both periplasmic fractions and IMAC purified B1/5 diabody was found to bind to BCL-1 lymphoma cells by FACS scan analysis, as described in Example 18. Binding of the B1/5 diabody to the lymphoma was detected by a shift in the cell population to a higher fluorescence reading.

Such bivalent anti-idiotype diabodies may prove useful for cross-linking cell surface antigen, triggering receptors and also triggering apoptosis. Bispecific diabodies cross-linking antigens on the surface of the same cell may likewise be used. The small size of diabodies may be particularly advantageous for cross-linking antigen on the same cell.

Example 20

Preparation and Characterisation of Bispecific Anti-HIV gp120 HIV V3 loop-antihumanFcR1 Diabody F58 is a mouse monoclonal antibody that binds to V3 loop of HIV 3B gp120. (ref. PCT/GB92 /01755). It has been cloned as a scFv fragment in the phagemid vector pUC119SfiNotmyc.

Construction of Bispecific Diabody 022/F58/0

The two antibody specificities 022 (anti-human FcRI) and F58 (anti-V3 loop HIV 3B gp120) were combined in the bispecific diabody format fusing the VH and VL directly with 0 linker in the orientation VH-VL in the phagemid vector pUC119SfiNotmyc. The linker sequence was incorporated into the primer Vkba-SacLink0BstEII used to amplify the 5' end of Vk and into the VH1fo-BstEIILink0Sac used to amplify the 3' end of VH. A restriction site for BstEII was incorporated 5' of the linker sequence of primer Vkba-SacLink5BstEII and a restriction site for SacI was incorporated 5' of the linker sequence of primer VH1fo-BstEIILink5Sac (SEQ ID NO: 53). This allowed the assembled VH-linker and linker-VL fragments to be cloned in a 2-way ligation reaction into the expression vector pUC119 022/5 BstEII/SacI.

VHF58 DNA was amplified with primers VH1fo-2 and VH1ba, the VkF58 DNA was amplified with the primers Vk4fo and Vk2ba. Intergenic region N2 including gIII leader (Example 1) was amplified with primers NterVHfo and CterVkba. The 3 fragments were gel-purified and then PCR assembled using standard conditions and the assembly product gel-purified and reamplified with the primers Vkba-SacLink5BstEII and VH1fo-BstEIILink5Sac.

The final product of the PCR reaction was digested with restriction enzymes SacI and BstEII. The recombinant diabody 022/5 in pCantab6 (see example 17) was cut with BstEII/SacI to give a 022/5 vector construct and the assembled VHF58 and the VLF58 DNA fragments were ligated with it in a molar ratio 3:1 (VLN2VH : pCantab6-022/5). The resulting ligation mix was used to transform E. coli HB2151 cells. Recombinants were screened for inserts of correct size by PCR amplification of recombinant colonies using primers LMB3 (SEQ ID NO: 85) and fdSeq.

Expression and Assay

For analysis by ELISA, periplasmic preparations of soluble diabody were made. The soluble diabody was expressed by growth at 37° C. Cells in log phase growth in 2 mL 2YT/0.1% glucose/100 μg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold TBS and sonicated for 10 minutes or until the cell suspension became translucent. The sonicated cell suspension was centrifuged (1000 g for 10 minutes) and the diabody-containing supernatant used in ELISA.

For assay of the bispecific diabody, ELISA was performed for the FcγRI receptor as described in example 17 and for the HIV gp120 V3 loop antibody the following protocol was used. 50 μL supernatant+50 μL 3% BSA/TBS was added to ELISA wells coated with gp120 (50 ng mL$^{-1}$ in PBS), blocked with 3% BSA/PBS. A standard ELISA protocol was followed (H. R. Hoogenboom et al., Nucl. Acids Res. 19, 4133–4137 1991) using detection of the myc-tag with the monoclonal antibody 9E10, and horseradish peroxidase conjugated anti mouse IgG. Positive ELISA readings were obtained (greater than 1.0 after 10 min.) for both antigens.

Purification of 022/F58/0 Diabody

To make purified diabody, soluble diabody was expressed by growth in IPTG induced cells, as described in example 3 and the diabody was purified from the culture supernatant. Purification was with imobilised Metal Affinity Chromatography (IMAC) using "Qiagen" nickel NTA agarose (cat no 30210) using the manufacturers instructions.

The purified protein bound strongly and specificially to both HIV 3B gp120 and HuFcRI (as determined by ELISA).

Example 21

Preparation and Characterisation of Bispecific Anti-2-phenyloxazol-5-one, Anti-mouse Lambda Light Chain Diabody A clone encoding a bispecific diabody directed against 2-phenyl-5-oxazolone and the mouse λ light chain with a zero amino acid linker was prepared from DNA encoding an antibody against 2-phenyl-5-oxazolone derived from hybridoma NQ11 (anti-mouse (see example 1) and from DNA derived from a hybridoma LS136 directed against a mouse lambda light chain using the methodology essentially as described in example 1. The bivalent antibody λ directed against the mouse lambda light chain was prepared as an intermediate step.

LS136 is a murine hybridoma directed against mouse antibody light chains. It has been cloned in a diabody format using a 5 residue linker in the orientation VH-GGGGS-VL in the phagemid vector pUC119SfiNotmyc. The linker sequence was incorporated into the primer (VkCbaLink5BstEII and primer 4 (Table 1 (SEQ ID NOS: 44 & 4, respectively)) used to amplify the 5' end of Vk. Primer 4 also introduces a SacI restriction site at the 5' end of the Vk. A restriction site for BstEII was incorporated 5' of the linker sequence of primer VkCbaLink5BstEII and primer 4 (SEQ ID NOS: 44 & 4, respectively) and also at the 3' end of VH1FOR-2 (E. S. Ward, D. Gussow, A. D. Griffiths, P. T. Jones and G. Winter, Nature 341, 544–546 1989). This allowed the VH and linker-VL fragments to be cloned in a 3-way ligation reaction into the expression vector pUC119SfiNotmyc.

RNA was extracted from LS136 hybridoma cells and used to prepare cDNA. LS136 VH and VL domain DNA was amplified by PCR from cDNA using primers pairs VH3Aba and VH1FOR-2, and VkCba and Vk4FOR (T. Clackson, H. R. Hoogenboom, A. D. Griffiths and G. Winter, Nature 352, 624–628 1991) respectively using standard conditions and reamplified by using VH3AbaSfi and VH1for-2 (for VH) and primer 4 (as described in the PNAS paper) and Vk4foNot (for Vk). The product of the VH PCR reaction was digested with restriction enzymes SfiI and BstEII, and the product of the Vk PCR reaction was digested with restriction enzymes NotI and BstEII. The VH and the VL domain DNA was simultaneously ligated into SfiI/NotI digested pUC119SfiNotmyc in a molar ratio 3:3:1 (VH:VL:pUC119SfiNotmyc or pCantab6) and the resulting ligation mix used to transform E. coli TG1 cells. The VH and VL domain DNA was also ligated into Sfi/Not digested pCANTAB6 vector (FIG. 20) in the same way and transformed into E.coli HB2151 cells. Recombinants were screened for inserts of correct size using primers LM92 and LM93 (SEQ ID NOS: 84 & 85, respectively) for recombinants in the vector pUC119SfiNotmyc or LMB3 (SEQ ID NO: 85) and fdSeq for recombinants in the vector pCANTAB6.

Expression of the LS136 Diabody

Soluble diabody was expressed by growth of the pUC119SfiNotmyc clone at 37° C. Cells in log phase growth in 2 mL 2YT/0.1% glucose/100 mg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in ELISA as below.

50 μL periplasmic supernatant and 50 μL 3% BA/PBS was added to ELISA wells coated with mouse IgM1 or mouse IgG2al (both from Sigma) (10 μg mL in PBS), blocked with 3% BSA/PBS. A standard ELISA protocol was followed (H. R. Hoogenboom et al., Nucl. Acids Res. 19, 4133–4137 1991) using detection of the myc-tag with the monoclonal antibody 9E10, and horseradish peroxidase conjugated anti mouse IgG (for IgMλ) and biotinylated anti mouse k chain and peroxidase-biotin-streptavidin complex (both Amersham) (for IgG2aλ). ELISA readings after 10 minutes were greater than 1.0.

Construction of Bispecific Diabody LS136/NQ11/5 and Bispecific Diabody LS136/NQ11/0

The two antibody specificities LS136 (anti-mouse 1 antibody light chain) and NQ11 (anti-phOx) were combined in the bispecific diabody format fusing the VH and VL with a 15 amino acid linker VH-GGGGS-VL or directly with 0 linker in the orientation VH-VL in the phagemid vector pUC119SfiNotmyc. The linker sequence was incorporated into the primers 4 and 5 (Table 1 (SEQ ID NOS: 4 & 5, respectively)) used to amplify the 5' end of Vk and into the primers 7 and 8 (Table 1 (SEQ ID NOS: 7 & 8, respectively)) used to amplify the 3' end of VH. A restriction site for BstEII was incorporated 5' of the linker sequence of primer 5 and a restriction site for SacI was incorporated 5' of the linker sequence of primer 8. This allowed the assembled VH-linker and linker-VL fragments to be cloned in a 3-way ligation reaction into the expression vector pUC19LS136/5 BstEII/SacI.

Construction of the Bispecific Diabody LS136/NQ11/5 (5 Amino Acid Linker)

VHNQ11 was amplified with primers 2 and 7 (Table 1 (SEQ ID NOS: 2 & 7, respectively)), the VkNQ11 was amplified with the primers 1 and 4 (SEQ ID NOS: 1 & 4, respectively) using scFvNQ11 cloned into fdDOG-1 as template. The product of the VH PCR reaction was digested with restriction enzymes AscI and SacI, and the product of the VL PCR reaction was digested with restriction enzymes AscI and BstEII. A vector fragment of diabody LS136/5 (see above) was cut with BstEII/SacI and the VH and the VL domain DNA were simultaneously ligated with it in a molar ratio 3:3:1 (VH:VL:pUC119-LS136/5). The resulting ligation mix used to transform E. coli TG1 cells. Recombinants were screened for inserts of correct size using primers LMB2 and LMB3 (SEQ ID NOS: 84 & 85, respectively) for PCR amplification of recombinant colonies.

Construction of the Bispecific Diabody LS136/NQ11/0 (Zero Amino Acid Linker)

VHNQ11 was amplified with primers 2 and 8 (Table 1 (SEQ ID NOS: 2 & 8, respectively)), the VkNQ11 was amplified with the primers 1 and 5 using scFvNQ11 cloned into fdDOG-1 as template. The product of the VH PCR reaction was digested with restriction enzymes AscI and SacI, and the product of the VL PCR reaction was digested with restriction enzymes AscI and BstEII. A vector fragment of diabody LS136/5 (see above) was cut with BstEII/SacI and the VH and the VL domain DNA were simultaneously ligated with it in a molar ratio 3:3:1 (VH:VL:pUC119-LS136/5). The resulting ligation mix used to transform E. coli TG1 cells. Recombinants were screened for inserts of correct size using primers LMB2 and LMB3 (SEQ ID NOS: 84 & 85, respectively) for PCR amplification of recombinant colonies.

Expression of Bispecific Diabody LS136/NQ11/5 and Bispecific Diabody LS136/NQ11/0

Soluble diabody was expressed by growth at 37° C. Cells in log phase growth in 2 mL 2YT/0.1% glucose/100 μg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing-supernatant used in ELISA for λ light chain as above or for phOx as in example 1. ELISA signals of greater than 1.0 were obtained after 10 minutes. This indicates that the diabody preparation contains both binding sites.

Such diabodies, binding to antibodies and also to other antigens, for example tumour cell markers, might be useful for recruiting antibody effector functions to tumour sites.

Example 22

Mutagenesis of Residues at the Interface Between the Two VH Domains of the NQ11/B1.8 Ox/NIP Diabody As noted earlier, we have examined the model of the (VH-VL) D1.3 diabody and selected residues at the interface of the VH domains to be modified for regulation of cooperativity and stability in the NQ11/B1.8 diabody whose construction and cooperative properties were described in examples 3 and 4.

The interface has been modified with various aims:

(i) introducing an ionic bond:

In mutation B1.8 T86K residue 86 of the B1.8 VH domain was converted from a threonine to a lysine, giving the potential to form ionic bonds with Asp88 of the NQ11 VH domain.

In mutation NQ11 K43E residue 43 of the NQ11 VH domain was converted into a glutamic acid, giving the potential to form an ionic bond with lysine 43 of the B1.8 VH domain.

(ii) introducing a disulphide bridge:

In mutation NQ11 K43C B1.8 R43C residue 43 of the NQ11 VH domain and residue 43 of the B1.8 VH domain were converted to a cysteine, giving the potential for forming a disulphide bridge between residues 43 of the two domains.

(iii) increasing the number of hydrogen bonds:

In mutation NQ11 R86Q residue 86 of the NQ11 VH domain was converted from an arginine to a glutamine, giving the potential for further hydrogen bonds.

(iv) increasing the number of hydrophobic interactions:

In mutation NQ11 K43L B1.8 R43I lysine 43 of the NQ11 VH domain was converted into a leucine and arginine 43 of the B1.8 VH domain was converted into an isoleucine, giving increased potential for hydrophobic packing at the interface between the two VH domains.

(v) increasing repulsive interactions:

In mutation B1.8 T86E threonine 86 of the B1.8VH domain was converted into a glutamate, leading to the potential for repulsive interactions with aspartate 88 of the NQ11 VH domain.

Mutagenesis Reactions

The NQ11/B1.8 Ox/NIP diabody clone described in example 3 was digested with HindIII and EcoRI and sub-cloned into the phagemid vector pBluescript II KS- (Stratagene) cut with HindIII and EcoRI. Single stranded DNA was prepared following rescue with M13K07 and in vitro mutagenesis was performed (Amersham). The following mutagenic oligonucleotides were used:

For mutation B1.8 T86K oligonucleotide T86K (Table 1 (SEQ ID NO: 54));

For mutation NQ11 K43E oligonucleotide K43E (SEQ ID NO: 55);

For mutation NQ11 K43C B1.8 R43C two oligonucleotides were used;:

K43C and R43C (SEQ ID NOS: 56 & 57, respectively);

For mutation NQ11 R86Q oligonucleotide R86Q (SEQ ID NO: 58);

For mutation NQ11 K43L B1.8 R43I two oligonucleotides were used;

K43L and R43I (SEQ ID NOS: 59 & 60, respectively);

For mutation B1.8 T86E oligonucleotide T86E (SEQ ID NO: 61).

Colonies generated by the mutagenesis procedure were analysed for the presence of mutations by cycle sequencing using Tag DNA polymerase (Boehringer) on template prepared by PCR. Mutant colonies were identified. Expression can then be measured at different temperatures and binding to both antigens studied by ELISA and BIACore analysis under various conditions. The effect of the mutations on the stability and allosteric binding properties (see Example 4) of the diabody will be determined.

Example 23

Construction and Characterisation of a NQ11 Diabody Directed Against 2-phenyloxazol-5-one With Cysteine at the C Terminus of the Light Chain to Introduce a Disulphide Bridge Crosslinking the Chains In this example a disulphide bridge is incorporated into a bivalent NQ11 diabody directed against 2-phenyloxazol-5-one (phOx), in the format with the VH domain N-terminal to the VL domain with a 5 aminoacid linker. The disulphide bridge is formed between cysteine residues incorporated at the C-terminus of the VL domain. This C-terminal region is relatively unconstrained in the diabody model. The two C-termini appear to be close in the diabody model. The aim of this experiment was to establish that disulphide bridges could be formed between these C-termini.

The construct made in this example incorporated a cysteine residue at the C-terminus of the VL chain directly after the C-terminal/lys-Arg sequence. A cysteine residue was inserted at the C-terminus of the VL domain by performing a PCR using PCR primers 10 (SEQ ID NO: 30) (which primes 5' to the DNA encoding the diabody molecule) and 11 (SEQ ID NO: 31) (which primes at the 3' end and incorporates the cysteine codon) on template of construct I (5 residue linker). The PCR fragment was digested with the restriction enzymes PstI and NotI, and cloning into a phagemid expression vector (pUC119SfiNotpolymyc). The diabody thus generated bound to phOx-BSA as shown by positive signals in ELISA on phOx-BSA coated plates (performed as in example 1).

The presence of disulphide bridges was established by purifying the bivalent diabody using affinity chromatography on phOx-BSA-Sepharose (T. Clackson et al Nature 352 624–628, 1991) and analysing the purified protein using SDS-polyacrylamide electrophoresis under reducing or non-reducing conditions. The parent NQ11 diabody without the C terminal cysteines migrates with a molecular mass of 25000 daltons under both reducing and non-reducing conditions. Under reducing conditions the NQ11 diabody with a C terminal cysteine migrated with a molecular mass of 25000 daltons while under non-reducing conditions about 30 to 50% of the protein now migrated with a molecular mass of 50000 daltons indicating that this proportion of the protein had formed a covalent disulphide bridge between the chains. The disulphide linked diabody copurified with non-linked diabody on affinity chromatography indicating that the disulphide linked diabody must be able to bind to phOx-BSA.

Example 24

Use of Self Splicing Introns in the Construction of Diabody Molecules

In the work described in this example, a self splicing intron was introduced between the VH and VL domain genes of two antibodies cloned in the diabody format, NQ11 and D1.3 directed against 2-phenyloxazol-5-one and hen egg lysozyme respectively. This self splicing intron was shown to be spliced out following expression, as determined by the expression of functional bivalent diabodies.

Construction of NQ11 and D1.3 Clones Containing a Self-splicing Intron, Excised to Leave a Five Amino Acid Linker Between VH and VL Domains of Bivalent Diabodies The self-splicing intron from Tetrahymena (T. R. Cech Ann. Rev. Biochem. 59 543–568, 1990) has been shown to be able to splice in the E.coli cytoplasm. Such a self-splicing intron, from clone ICE10 (Ian Eperon, University of Leicester) was inserted between the genes encoding the VH and VL domains of the antibodies D1.3 and NQ11 in such a way as to create upon splicing out an open reading frame encoding a diabody with linker VH-GLSSG-VL. Without splicing no functional diabody can be produced as the self splicing intron contains several stop codons in 3 reading frames.

A restriction site for BstEII was incorporated at the 5' end of the primer T1baBstEII (SEQ ID NO: 83) and a SacI restriction site introduced in the primer T1foSac. This allowed the self splicing intron fragment to be cloned in a 2-way ligation reaction into the expression vectors pUC119D1.3 (encoding the V domains of the D1.3 anti-lysozyme antibody) or pUC19NQ11 (encoding the V domainds of the anti-phOx antibody NQ11) each cut with BstEII and SacI.

T1baBstEII (SEQ ID NO: 83) primes at the 5' end of the self splicing intron and conserves the internal guidance sequence (IGS) required for splicing activity and inserts a extra glycine residue at the 3' end of the VH domain. T1foSac primes at the 3' end of the self splicing intron and conserves the thymidine base just 3' of the self splicing intron which, though not part of the intron, is present in Tetrahymena DNA. T1foSac inserts a extra Gly and Ser residue at the 5' end of the VL creating a 5 amino acid linker.

The self splicing intron was amplified with the primers T1baBstEII and T1foSacI (SEQ ID NOS: 83 & 82, respectively) using standard conditions (as in example 14). The product of the PCR reaction was digested with restriction enzymes SacI and BstEII and ligated into BstEII/SacI digested pUC119D1.3 or pUC19NQ11 in a molar ratio 4:1 (SSI:pUC119D1.3 or pUC19NQ11) and the resulting ligation mixes used to transform E. coli TG1 cells. Recombinants were screened for inserts of correct size using primers specific for self splicing intron, T1foSac and T1baBstEII (SEQ ID NO: 83).

Soluble diabody was expressed by growth at 37° C. Cells in log phase growth in 2 mL 2YT/0.1% glucose/100 µg mL$^{-1}$ ampicillin were induced by adding IPTG to a final concentration of 1 ml IPTG and Grown 3 hours 22° C. The cells were centrifuged (1000 g 10 minutes) and the cell pellet resuspended in 100 µl ice cold PBS/1 mM EDTA and left on ice, 60 minutes. The cell suspension was centrifuged (1000 g for 10 minutes) and the diabody-containing supernatant used in ELISA on lysozyme and phOx as described in example 1.

The ELISA signal was equivalent (greater than 1.0 after 10 min) for the spliced 5 amino acid linker D1.3 diabody to that obtained with the 5 amino acid linker D1.3 diabody (constructed in example 1). However for the spliced 5 amino acid linker NQ11 diabody the signal was much lower (0.2 compared to 2.0 after 20 min) when compared to the 5 amino acid linker diabody constructed in example 1. There two possible explanations for this:

the NQ11 diabody is not functional with the GLSSG linker sequence (SEQ ID NO: 103), although this appears unlikely;

self-splicing does not work properly in the case of the diabody NQ11 because the DNA sequence 3' of the intron (at the 5' of the VL domain) is not suitable for self splicing. Whereas the D1.3 sequence at 5' end of the VL domain gene is efficient at allowing self splicing, the NQ11 sequence in this region is poor.

Construction of NQ11 and D1.3 Clones Containing a Self-splicing Intron Including a loxP Site, Excised to Leave a Six Amino Acid Linker Between VH and VL Domains of Bivalent Diabodies The primers T1ba2BstEII (SEQ ID NO: 81) and T1fo2SacI were designed to introduce into the NQ11 construct sequences 3' of the self splicing intron which should enable efficient self splicing at the RNA level.

The self splicing intron was amplified with T1ba2BstEII (SEQ ID NO: 81) and T1fo2SacI by PCR. This intron was inserted between the VH and VL domain genes of antibody NQ11and creates upon splicing out an open reading frame encoding a diabody with linker VH-GSLKVG-VL (SEQ ID NO: 104). Without splicing no functional diabody can be produced as the self splicing intron contains several stop codons in 3 reading frames.

A restriction site for BstEII was incorporated at the 5' end of the primer T1ba2BstEII (SEQ ID NO: 81) and a SacI restriction site introduced in the primer T1fo2Sac (SEQ ID NO: 80). This allowed the self splicing intron fragment to be cloned in a 2-way ligation reaction into the expression vector pUC19NQ11 cut with BstEII and SacI. T1baBstEII (SEQ ID NO: 83) primes at the 5' end of the self splicing intron and conserves the internal guidance sequence (IGS) required for splicing activity and inserts a extra glycine residue at the 3' end of the VH. T1foSac primes at the 3' end of the self splicing intron and conserves the thymidine base just 3' of the self splicing intron which, though not part of the intron, is present in Tetrahymena DNA and inserts a extra Gly and Ser residue at the N-terminal end of the VL domain.

The self splicing intron used in this case contained a lox P site inserted between bp 236 and 237. It was amplified with the primers T1ba2BstEII (SEQ ID NO: 81) and T1fo2SacI using standard conditions. The product of the PCR reaction was digested with restriction enzymes SacI and BstEII and ligated into BstEII/SacI digested pUC19NQ11 in a molar ratio 4:1 (SSI:pUC19NQ11) and the resulting ligation mix used to transform E. coli TG1 cells. Recombinants were screened for inserts of correct size using the primers specific for self splicing intron, T1foSac and T1baBstEII (SEQ ID NO: 83).

Soluble diabody was expressed as above and assayed by ELISA. In this case an equivalent signal (greater than 1.0 after 10 min) was obtained with the 6 amino acid linker NQ11 diabody formed by self splicing as for the 5 amino acid linker diabody constructed in example 1. Thus this strategy allows more efficient self splicing in the NQ11 construct.

Example 25

Construction and Characterisation of Diabody Molecules Containing Fusions with Metallothionein For the imaging of tumours, it may be possible to incorporate a metallothionein peptide either as part of a linker between VH and VL domains or as an extension at the C terminus of the VL domains. This could then be labelled by introducing a radioactive metal ion which would be chelated by the metallothionein peptide.

If the metallothionein peptide was incorporated as part of the linker between the VH and VL domains of the diabody then the formation of the diabody rather than a scFv could still be possible. (A longer linker would normally favour scFv formation.) The incorporation of cysteines in the linker sequence to give disulphide bonds within linkers could promote pairing of the VH and VL domains from the same chain to favour diabody formation.

To investigate this, metallothionein sequences were used as linkers between antibody V domains in the diabody format. The metallothionein sequence was split into two peptides A: <u>GGG</u>DPNCSCAAGDSCTCA<u>GGS</u> (SEQ ID NO: 105) and B: <u>GGGG</u>SCKCKECKCTSCKG<u>GSG</u> (SEQ ID NO: 106) with the underlined sequences introduced as spacers (effective linker length 21 amino acids). A bispecific diabody was made in the format—chain 1: VHNQ11-A-VkD1.3, chain 2: VHD1.3-B-VkNQ11, the latter chain also having a C-terminal c-myc tag. The second bispecific diabody was constructed with the NQ11/D1.3 zero linker diabody with one of each of the metallothioein peptides at the C-terminus of each chain. Both constructs were expressed and demonstrated to bind to both lysozyme and BSA derivatized with 2-phenyl-5-oxazolone after purification on HEL-sepharose (example 1) indicating that the construct with cysteine residues in the linker is able to fold as a bispecific diabody.

TABLE 1

Oligonucleotides used

| | |
|---|---|
| Primer 1: | 5'-GAC TCA TTC TCG ACT GAG CTC ACT TGG CGC GCC TTA TTA CCG TTT GAT CTC GAG CTT GGT CCC- |
| Primer 2: | 5'-GTC CTC GCA ACT GGC GCG CCA CAA TTT CAC AGT AAG GAG GTT TAA CTT GTG AAA AAA TTA TTA TTC GCA ATT-3' |
| Primer 3: | 5'-GAG CCA TCA ATC GAT CTG GTC ACC GTC TCC TCA GAC ATT GAG CTC ACC CAG TCT CCA-3' |
| Primer 4: | 5'-GAG CCA TCA ATC GAT CTG GTC ACC GTC TCC TCA (GGC GGT GGC GGA TCG)$_2$ GAC ATT GAG CTC ACC CAG TCT CCA-3' |
| Primer 5: | 5'-GAG CCA TCA ATC GAT CTG GTC ACC GTC TCC TCA (GGC GGT GGC GGA TCG)$_2$ GAC ATT GAG CTC ACC CAG TCT CCA-3' |
| Primer 6: | 5'-GAG CCA TCA ATC TCG GAG CTC GAT GTC TGA GGA GAC GGT GAC CGT GGT CCC TTG GCC CC-3' |
| Primer 7: | 5'-GAG CCA TCA ATC TCG GAG CTC GAT GTC CGA TCC GCC ACC GCC TGA GGA GAC GGT GAC CGT GGT CCC TTG GCC CC-3' |
| Primer 8: | 5'-GAG CCA TCA ATC TCG GAG CTC GAT GTC (CGA TCC GCC ACC GCC)$_2$ TGA GGA GAC GGT GAC CGT GGT CCC TTG GCC CC |
| AJR21: | 5'-GC ACC CTG GTC ACC GTC TCG AGC GGC GGT GGC GGA TCG GAC ATT GTG ATG ACC CAG TCT CAC-3' |
| MAKVHBACKNCO: | 5'-ACT GCG GC CAG CCG GCC ATG GCC CAG GTG CAG CTG AAG GAG TCA GG-3' |
| FL-VL: | 5'-CAA GGG ACC ACG GTC ACC GTC TCG AGC GGG GGT GGC GGA TCC GAC ATT GAG CTC ACC CAG TCT-3' |
| ZL-VL: | 5'-CAA GGG ACC ACG GTC ACC GTC TCG AGC GAC ATT GAG CTC ACC CAG TCT-3' |
| fd-tet-seq24: | 5'-TTT GTC GTC TTT CCA GAC GTT AGT-3' |
| Mab32-VL-REV: | 5'-ACA CTT GAG CTG GCC CT-3'. |
| FL-VL-A2: | 5'-CAA GGG ACC ACG GTC ACC GTC TCG AGC GGG GGT GGC GGA TCC CAG TCT GTG CTG ACG CAG CCG-3' |
| ZL-VL: | 5'-CAA GGG ACC ACG GTC ACC GTC TCG AGC CAG TCT GTG CTG ACG CAG CCG-3' |
| VL-A2-REV: | 5'-GCT GCT TCC AGA GCA GG-3' |
| Primer 3 NQ11 VH-1 | 5'-CCA TCA ATC GAT CTG GTC ACC GTC TCC GAC ATT GAG CTC ACC CAG TCT CCA-3' |
| Primer 3 D1.3 VL-1 | 5'-CCA TCA ATC GAT CTG GTC ACC GTC TCC TCA ATT GAG CTC ACC CAG TCT CCA-3' |
| Primer 3 D1.3 VL-2 | 5'-CCA TCA ATC GAT CTG GTC ACC GTC TCC TCA GAG CTC ACC CAG TCT CCA GCC TCC-3' |
| Primer 3 NQ11 VH-1/ D1.3 VL-2: | 5'-CCA TCA ATC GAT CTG GTC ACC GTC TCC GAG CTC ACC CAG TCT CCA GCC TCC CTT-3' |
| Primer 6 D1.3 VH-1 | 5'-GAG CCA TCA ATC TCG GAG CTC GAT GTC GGA GAC GGT GAC CGT GGT CCC TTG GCC-3' |
| Primer 6 NQ11 VL-1 | 5'-GAG CCA TCA ATC TCG GAG CTC GAT TGA GGA GAC GGT GAC CGT GGT CCC TTG GCC-3' |
| Primer 6 D1.3 VH-2 | 5'-GAG CCA TCA ATC TCG GAG CTC GAT GTC GAC GGT GAC CGT GGT CCC TTG GCC CCA GTA GTC-3' |

TABLE 1-continued

Oligonucleotides used

| | |
|---|---|
| Primer 6 D1.3 VH-2/<br>NQ11 VL-1: | 5'-GAG CCA TCA ATC TCG GAG CTC GAT GAC GGT GAC CGT GGT CCC TTG GCC CCA GTA GTC-3' |
| PUC19rev: | 5-AAC AGC TAT GAC CAT G-3' |
| HuJH6ForLINK | 5-CGA TCC GCC ACC GCC TGA GGA GAC GGT GAC CGT GGT CCC-3' |
| FDTSEQ1 | 5'-GTC GTC TTT CCA GAC GTT AGT-3' |
| LINKHullBack | 5'-GGC GGT GGC GGA TCG CAG TCT GTG TTG ACG ACG CAG CCG CC-3' |
| Primer 10: | 5'-AAC AGC TAT GAC CAT G-3' |
| Primer 11: | 5'-GAG TCA TTC TCG ACT TGC GGC CGC ACA CCG TTT GAT CTC GAG CTT GGT CC-3' |
| VH022baSfi | 5'-CAT GCC ATG ACT CGC GGC CCA GCC GGC CAT GGC CGA GGT CCA ACT GGT GGA GAG CGG T-3' |
| VLB18baLink0BstE | 5'-CCA TCA ATC GAT CTG GTC ACC GTC TCC TCA CAG GCT GTT GGG ACA CAG GAA TCT GCA-31 |
| VlBl8foAsc | 5'-GAG TCA TTC TCG ACT TGG CGC GCC TTA TTA CCG TTT GAT CTC GAG GAC AGT CAG-3' |
| Vk022SacbaLink5BstEII: | 5'-GAG CCA TCA ATC GAT CTG GTC ACC GTC TCC TCA GGC GGT GGC GGA TCG GAC ATC GAG CTC ACC CAG AGC CCA-3' |
| Vk022foNot | 5'-GAG TCA TTC TCG ACT TGC GGC CGC ACG TTT GAT TTC CAC CTT GGT CCC-3' |
| VH2C11baSfi | 5'-CAT GCC ATG ACT CGC GGC CCA GCC GGC CAT GGC CGA GGT GCA GCT GGT GGA GTC TGG-3' |
| Vk2C11baLink5BstE: | 5'-GAG CCA TCA ATC GAT CTG GTC ACC GTC TCC TCA GGC GGT GGC GGA TCT GAC ATC AGA TG ACC CAG TCT CCA-3' |
| LinkbaAscI21: | 5'-GAG TCA TTC TCG ACT CTG TCG GGC GCG CCT CAT GAT TAC GCC CAG CTT GCA TGC-3' |
| VHB1fo: | 5'-CAG ATC TGA GGA GAC GGT GAC CGT GGT CCC TGC GCC CC-3' |
| VHBlbaSfi: | 5'-CAT GCC ATG ACT CGC GGC CCA GCC GGC CAT GGC CGA AGT GAA GCT GGT GGA GTC TGG-3' |
| VLB1baLink5BStE: | 5'-GAG CCA TCA ATC GAT CTG GTC ACC GTC TCC TCA GGC GGT GGC GGA TCG GAC ATT GAG CTC ACC CAG TCT CAA-3' |
| VH3Abafi | 5'-CAT GCC ATG ACT CGC GGC CCA GCC GGC CAT GGC CGA CSA GGT GAA GCT GGT GGA RTC TGG-3' |
| VKCbaLink5BstE | 5'-GAG CCA TCA ATC GAT CTG GTC ACC GTC TCC TCA GGC GGT GGC GGA TCG GAC ATT GTG CTR ACC CAG TCT CCA-3' |
| VH1foMTbSac | 5'-GAG CCA TCA ATC TCG GAG CTC GAT GTC CGA TCC GCC ACC GCC CTT GCA GGA GGT GCA TTT GCA CTC TTT GCA CTT GCA GGA GCC ACC GCC TGA GGA GAC GGT GAC CGT GGT CCC TTG GCC CC-3' |
| VkfoMTaAsc | 5'-GAC TCA TTC TCG ACT TGG CGC GCC TTA TTA GGC GCA GGT GCA GGA GTC ACC GGC GGC ACA GGA GCA GTT GGG ATC GCC ACC GCC GAT CTC GAG CTT GGT CCC TCC ACC-3' |
| VkbaMTaBstEII | 5'-GAG CCA TCA ATC GAT CTG GTC ACC GTC TCC TCA GGC GAT CCC AAC TGC TCC TGT GCC GCC GGT GAC TCC TGC ACC TGC GCC GGC GGT TCG GAC ATT GAG CTC ACC CAG TCT CCA-3' |
| VkfoMtbNot | 5'-GAG TCA TTC TCG ACT TGC GGC CGC TTG CA GGA GGT GCA TTT GCA CTC TTT GCA CTT GCA GGA GCC TCC ACC GCC GAT CTC GAG CTT GGT CCC TCC ACC-3' |
| VkCysfoNot16 | 5'-GAG TCA TTC TCG ACT TGC GGC CGC ACA CCG TTT GAT CTC GAG CTT GGT CCC-3' |
| NterVHfo: | 5'-GCC AGG TCC TGA CTC CTG CAG CTG CAC CTG-3' |
| CterVkba | 5'-GGT GGA GGC ACC AAG CTG GAG ATC AAA CGG-3' |
| VkbaLink5-SacBstE: | 5'-GAG CCA TCA ATC GAT CTG GTC ACC GTC TCC TCA GGC GGT GGC GGA TCG GAC ATT GAA CTC ACC CAG TCT CCA-3' |
| VH1fo-BstELink5Sac: | 5'-GAG CCA TCA ATC TCG GAG CTC GAT GTC CGA TCC GCC ACC GCC TGA GGA GAC AGT GAC CGT GGT CCC TTG GCC CC-3' |
| T86K | 5'-CTC AGC AGC CTG AAA TCT GAG GAC TCT GCG GTC 3' |
| K43E | 5'-GTC CGC CAG CCT CCA GGA GAG GCA CTT GAG TGG 3' |
| K43C | 5'-CGC CAG CCT CCA GGA TGC GCA CTT GAG TGG TTG GGT TCT GTT AGA AAC 3' |
| R43C | 5'-AAG CAG AGG CCT GGA TGC GGC CTT GAG TGG ATT GGA AGG ATT GAT CC 3' |
| R86Q | 5'-ATA AAC ACC CTG CAA ACT GAG GAC AGT GCC ACT 3' |

TABLE 1-continued

Oligonucleotides used

| | |
|---|---|
| K43L | 5'-GTC CGC CAG CCT CCA GGA TTG GCA CTT GAG TGG 3' |
| R43I | 5'-GTG AAG CAG AGG CCT GGA ATC GGC CTT GAG TGG 3' |
| T86E | 5'-CTC AGC AGC CTG GAA TCT GAG GAC TCT GCG GTC 3' |
| SfiVlBack: | 5'-GTC CTC GCA ACT GCG GCC CAG CCG GCC ATG GCC GAC ATC GAC CTC ACC CAA ACT CCA-3' |
| VhForNot: | 5'-GAG TCA TTC TCG ACT TGC GGC CGC TGA GGA GAC GGT GAC CGT GGT CCC TTG GCC CC-3' |
| VL/VHBackXhol: | 5'-CGT TCG GAG GGG GGA CCA AGC TCG AGA TCA AAC GGC AGG TGC AGC TGC AGG AGT CAG G-3' |
| VL/VHBackXholA: | 5'-CGT TCG GAG GGG GGA CCA AGC TCG AGA TCA AAC GGG GAG GCC AGG TGC AGC TGC AGG AGT CAG C-3' |
| B1.8VLPRO | 5'-CCA GAT CAT TTA CCC ACT GGT C-3' |
| LINK-FOR-XHOI: | 5'-TGG AGA CTG GGT GAG CTC AAT GTC GCT CGA GCC ACC GCC AGA GCC-3' |
| pUCReverse: | 5'-AGC GGA TAA CAA TTT CAC ACA GG-3' |
| MVKBBST: | 5-GGC CAA GGG ACC ACG GTC ACC GTC TCC TCA GAC ATT GAG CTC ACC CAG TCT CCA-3' |
| LBRBS 1: | 5-GGC ACC AAG CTG GAA ATC AAA CGG TAA TAA CCC TGC AGG TCG ACA AGG AGA CAG-3' |
| LBRBS 2: | 5'-GGG ACC AAG CTG GAA ATA AAA CGG TAA TAA CCC TGC AGG TCG ACA AGG AGA CAG-3' |
| LBRBS 4: | 5'-GGG ACA AAG TTG GAA ATA AAA CGG TAA TAA CCC TGC AGG TCG ACA AGG AGA CAG-3' |
| LBRBS 5: | 5'-GGG ACC AAG CTG GAG CTG AAA CGG TAA TAA CCC TGC AGG TCG ACA AGG AGA CAG-3' |
| LFRBS-2: | 5'-GGC CAT CGC TGG TTG GGC AGC CGC GG-3' |
| VH1BACKSfiKsp: | 5'-CAT GCC ATG ACT CAG GCC CAG CCG GCC ATG GCC TCC GCG GCT GCC CAA CCA GCG ATG GCC (C/G)AG GT(C/G) (A/C)A(A/G) CTG CAG-3' |
| VH1FOR-2Xho: | 5'-GCC TGA ACC GCC TCC ACC ACT CGA GAC GGT GAC CGT GGT CCC TTG GCC CCA-3' |
| VHTAG: | 5'-CAT GCC ATG ACT CAG GCC-3' |
| XhoTag: | 5'-AGC TGA ACC GCC TCC ACC GCT C-3' |
| BioGene3Lead | 5'-TTA TTA TTC GCA ATT CCT TTA GTT GTT CCT-3' |
| Tlfo2Sac | 5'-GAG CCA TCA ATC TCG AGC TC GAT GTC ACC TAC CTT ACG AGT ACT CCA AAA CTA ATC A-3' |
| Tlba2BstE | 5'-CCA TCA ATC GAT CTG GTC ACC GTC TCC TCA GGC TCT CTA AAT AGC AAT ATT TAC CT-3' |
| TlfoSacI: | 5'-GAG CCA TCA ATC TCG AGC TC GAT GTC ACC AGA CGA GTA CTC CAA AAC TAA TCG-3' |
| TlbaBstEII | 5'-CCA TCA ATC GAT CTG GTC ACC GTC TCC TCA GGT CTC TCT AAA TAG CAA TAT TTA CCT-3' |
| LMB2 | 5'-GTA AAA CGA CGG CCA GT-3' |
| LMB3 | 5'-CAG GAA ACA GCT ATG AC-3' |

TABLE 2

Binding activities of monomer and dimer fragments as determined by BIAcore and ELISA.

| | | | BIAcore and ELISA | | |
|---|---|---|---|---|---|
| Construct | Linkers | FPLC Oligomers | phOx | HEL | both‡ |
| I | 5/15 | D*/M* | +/+ | | −/− |
| II | 5/15 | D*/M&D*† | | +/+ | −/− |
| VI | 0/5/10/15 | all D*† | +/+/+/+ | +/+/+/+ | +/+/+/+ |
| VII | 5/10 | X*†/X*† | +/+ | +/+ | +/+ |
| VIII | 5/15 | D†/M† | −/− | −/− | |
| IX | 5/15 | D†/M† | −/− | −/− | |

As shown by FPLC and BIAcore of lysates by binding to antigen * or to 9E10 antibody †. M=mainly Monomer, D=mainly Dimer, M&D=both monomer and dimer clearly detectable, X=species running faster than M (seen with constructs VII) presumably due to equilibrium between the three chains. ‡by sandwich-ELISA and also by BIAcore, binding to HEL and then to phOx-BSA.

TABLE 3

Binding affinities and dissociation kinetics ($k_{off}$)

| Construct | $K_d$ (nM) for phOx | $k_{off}$ (s$^{-1}$) for phOx | $k_{off}$ (s$^{-1}$) for HEL |
|---|---|---|---|
| FVNQ11 (VH D97A) | 99 ± 21* | >0.05− | |
| IgG NQ11 | 110 | 10− | |
| FvD1.3 | | | 0.0028 |
| FabD1.3 | | | 0.0030 |
| IgG D1.3 | | | 0.0051$ |
| fragment VI (linker 15) | 110 ±12 | >0.04− | 0.0028 |
| fragment VI (linker 5) | 106 ±18 | >0.04− | 0.0022 |
| fragment VI (no linker) | 8 ±1.5 | 0.004 | 0.001 |

* from (21). $k_{off}$ too fast to measure by BIAcore, given values are slowest possible estimate.−value of $k_{off}$ measured from. Foote, J., et al. (1991) Nature (London) 352, 530–532 by stop-flow. $ value of $k_{off}=k_{on}\times K_d$ from Foote, J., et al. (1992) J. Mol. Biol. 224, 487–499 measured by stop-flow ($k_{on}$) and fluorescence quench ($K_d$).

Affinity constants (Kd) for phOx were determined by fluorescence quench, and dissociation kinetics ($k_{off}$) for HEL and phOx were determined by BIAcore. $k_{on}$ values are not presented (the active fraction can vary between different preparations (Griffiths, A. D., et al. (1993) EMBO J. 12, 725–734)). $k_{off}$ values for Fv, Fab and IgG D1.3 on HEL disagree with BIAcore data presented in Borrebaeck, C. A. K., et al. (1992) Bio/Technology 10, 697–698, for reasons to be discussed elsewhere.

TABLE 4

| CLONE | Primers for D1.3 VL PCR (NQ11 VH/D1.3 VL Junction) | Primers for D1.3 VL PCR (D1.3 VH/NQ11 VL Junction) | CONSTRUCT |
|---|---|---|---|
| NQ11/ D1.3 (0 link) | P1 + P3 | P2 + P6 | NQ11 VH/ D1.3 VL D1.3 VH/ NQ11 VL |
| Clone 1–3 (−1 link) | P1 + P3 NQ11 VH-1 | P2 + P6 D1.3 VH −1 | NQ11 VH − 1/ D1.3V D1.3 VH − 1/NQ11 V |
| Clone 1–4 (−1 link) | P1 + D1.3 VL-1 | P2 + P6 D1.3 VH −1 | NQ11 VH/ D1.3 VL − 1/ NQ11 V |
| Clone 2–3 (−1 link) | P1 + P3 NQ11 VH-1 | P2 + P6 NQ11 VL-1 | NQ11 VH − 1/ D1.3 V D1.3 VH/ NQ11 VL |
| Clone 2–4 (−1 link) | P1 + P3 D1.3 VL-1 | P2 + P6 NQ11 VL-1 | NQ11 VH D1.3 VL − 1 D1.3 VH/ NQ11 VL |
| Clone A E (−2 link) | P1 + P3 D1.3 VL-2 | P2 + P6 D1.3 VH-2 | NQ11 VH/ D1.3 VL − D1.3 VH − 2/NQ11 V |
| Clone C F (−3 link) | P1+ P3 NQ11 VH-1/D1.3 | P2+ P6 D1.3 VH2/NQ11 | NQ11VH −1/ D1.3 VL − D1.3 VH-2 NQ11 VL − |

TABLE 5

Cycling program for refolding of MAB 32 diabody

| Step | Time | Flow | % A | % B | % C |
|---|---|---|---|---|---|
| 1 | 0.0 | 2.00 | 100.0 | | 0.0 |
| 2 | 45.0 | 2.00 | 100.0 | | 0.0 |
| 3 | 46.0 | 2.00 | .0 | | 100.0 |
| 4 | 52.0 | 2.00 | .0 | | 100.0 |
| 5 | 60.0 | 2.00 | 100.0 | | 0.0 |
| 6 | 105.0 | 2.00 | 100.0 | | 0.0 |
| 7 | 106.0 | 2.00 | 4.0 | | 96.0 |
| 8 | 113.0 | 2.00 | 4.0 | | 96.0 |
| 9 | 120.0 | 2.00 | 100.0 | | 0.0 |
| 10 | 165.0 | 2.00 | 100.0 | | 0.0 |
| 11 | 166.0 | 2.00 | 8.0 | | 92.0 |
| 12 | 172.0 | 2.00 | 8.0 | | 92.0 |
| 13 | 180.0 | 2.00 | 100.0 | | 0.0 |
| 14 | 225.0 | 2.00 | 100.0 | | 0.0 |
| 15 | 226.0 | 2.00 | 12.0 | | 88.0 |
| 16 | 232.0 | 2.00 | 12.0 | | 88.0 |
| 17 | 240.0 | 2.00 | 100.0 | | 0.0 |
| 18 | 285.0 | 2.00 | 100.0 | | 0.0 |
| 19 | 286.0 | 2.00 | 16.0 | | 84.0 |
| 20 | 292.0 | 2.00 | 16.0 | | 84.0 |
| 21 | 300.0 | 2.00 | 100.0 | | 0.0 |
| 22 | 345.0 | 2.00 | 100.0 | | 0.0 |
| 23 | 346.0 | 2.00 | 20.0 | | 80.0 |
| 24 | 352.0 | 2.00 | 20.0 | | 80.0 |
| 25 | 360.0 | 2.00 | 100.0 | | 0.0 |
| 26 | 405.0 | 2.00 | 100.0 | | |
| 27 | 406.0 | 2.00 | 24.0 | | 76.0 |
| 28 | 412.0 | 2.00 | 24.0 | | 76.0 |
| 29 | 420.0 | 2.00 | 100.0 | | |
| 30 | 465.0 | 2.00 | 100.0 | | |
| 31 | 466.0 | 2.00 | 28.0 | | 72.0 |
| 32 | 472.0 | 2.00 | 28.0 | | 72.0 |
| 33 | 480.0 | 2.00 | 100.0 | | 0.0 |
| 34 | 525.0 | 2.00 | 100.0 | | |
| 35 | 526.0 | 2.00 | 32.0 | | 68.0 |
| 36 | 532.0 | 2.00 | 32.0 | | 68.0 |
| 37 | 540.0 | 2.00 | 100.0 | | |
| 38 | 585.0 | 2.00 | 100.0 | | |
| 39 | 586.0 | 2.00 | 36.0 | | 64.0 |
| 40 | 592.0 | 2.00 | 36.0 | | 64.0 |
| 41 | 600.0 | 2.00 | 100.0 | | |
| 42 | 645.0 | 2.00 | 100.0 | | |
| 43 | 646.0 | 2.00 | 40.0 | | 60.0 |
| 44 | 652.0 | 2.00 | 40.0 | | 60.0 |
| 45 | 660.0 | 2.00 | 100.0 | | |
| 46 | 705.0 | 2.00 | 100.0 | | |
| 47 | 706.0 | 2.00 | 44.0 | | 56.0 |
| 48 | 713.0 | 2.00 | 44.0 | | 56.0 |
| 49 | 720.0 | 2.00 | 100.0 | | |
| 50 | 765.0 | 2.00 | 100.0 | | |
| 51 | 766.0 | 2.00 | 48.0 | | 52.0 |
| 52 | 772.0 | 2.00 | 48.0 | | 52.0 |
| 53 | 780.0 | 2.00 | 100.0 | | |
| 54 | 825.0 | 2.00 | 100.0 | | |
| 55 | 826.0 | 2.00 | 52.0 | | 48.0 |
| 56 | 832.0 | 2.00 | 52.0 | | 48.0 |
| 57 | 840.0 | 2.00 | 100.0 | | |
| 58 | 885.0 | 2.00 | 100.0 | | |
| 59 | 886.0 | 2.00 | 56.0 | | 44.0 |
| 60 | 892.0 | 2.00 | 56.0 | | 44.0 |
| 61 | 900.0 | 2.00 | 100.0 | | |
| 62 | 945.0 | 2.00 | 100.0 | | |
| 63 | 946.0 | 2.00 | 60.0 | | 40.0 |
| 64 | 952.0 | 2.00 | 60.0 | | 40.0 |
| 65 | 960.0 | 2.00 | 100.0 | | |
| 66 | 1005.0 | 2.00 | 100.0 | | |
| 67 | 1006.0 | 2.00 | 64.0 | | 36.0 |
| 68 | 1012.0 | 2.00 | 64.0 | | 36.0 |
| 69 | 1020.0 | 2.00 | 100.0 | | |
| 70 | 1065.0 | 2.00 | 100.0 | | |
| 71 | 1066.0 | 2.00 | 68.0 | | 32.0 |
| 72 | 1072.0 | 2.00 | 68.0 | | 32.0 |
| 73 | 1080.0 | 2.00 | 100.0 | | |
| 74 | 1125.0 | 2.00 | 100.0 | | 0.0 |
| 75 | 1126.0 | 2.00 | 70.0 | | 30.0 |
| 76 | 1132.0 | 2.00 | 70.0 | | 30.0 |
| 77 | 1140.0 | 2.00 | 100.0 | | |
| 78 | 1185.0 | 2.00 | 100.0 | | |
| 79 | 1186.0 | 2.00 | 72.0 | | 28.0 |
| 80 | 1192.0 | 2.00 | 72.0 | | 28.0 |
| 81 | 1200.0 | 2.00 | 100.0 | | |
| 82 | 1245.0 | 2.00 | 100.0 | | |
| 83 | 1246.0 | 2.00 | 75.0 | | 25.0 |
| 84 | 1252.0 | 2.00 | 75.0 | | 25.0 |
| 85 | 1260.0 | 2.00 | 100.0 | | |
| 86 | 1305.0 | 2.00 | 100.0 | | |
| 87 | 1306.0 | 2.00 | 80.0 | | 20.0 |
| 88 | 1312.0 | 2.00 | 80.0 | | 20.0 |
| 89 | 1319.0 | 2.00 | 100.0 | | |
| 90 | 1364.0 | 2.00 | 100.0 | | |
| 91 | 1365.0 | 2.00 | 85.0 | | 15.0 |
| 92 | 1371.0 | 2.00 | 85.0 | | 15.0 |
| 93 | 1378.0 | 2.00 | 100.0 | | |
| 94 | 1423.0 | 2.00 | 100.0 | | |
| 95 | | | | | |

TABLE 6

Agglutination by bivalent and bispecific diabodies

| Clone | Coating protein on RBC's | Haemagglutination Dilution of periplasm | | | |
|---|---|---|---|---|---|
| | | Neat | 1:5 | 1:25 | 1:125 |
| D1.3 scFv | Lysozyme | − | − | − | − |
| | phOx-BSA | − | − | − | − |
| | Uncoated | − | − | − | − |
| D1.3/5 | Lysozyme | + | + | − | − |
| | phOx-BSA | − | − | − | − |
| | Uncoated | − | − | − | − |
| D1.3/0 | Lysozyme | + | + | − | − |
| | phOx-BSA | − | − | − | − |
| | Uncoated | − | − | − | − |
| NQ11/D1.3/0 | Lysozyme only | − | − | − | − |
| | phOx-BSA | − | − | − | − |
| | Lysozyme coated and phOx-BSA coated | + | + | − | − |
| | Uncoated | − | − | − | − |

D1.3scFv = Monovalent lysozyme specific scFv
D1.3/5 = Bivalent, lysozyme specific, 5 linker diabody
D1.3/0 = Bivalent, lysozyme specific, 0 linker diabody
NQ11/D1.3/0 = Bispecific (phOx/lysozyme) 0 linker diabody

ADDITIONAL KEY TO FIGURES

FIG. 6:
Vertical arrows indicate restriction sites.
x—scFv linker.
y—10-residue linker.
z—5-residue linker.
A—cloning via PCR assembly.
B—cloning via restriction sites.

FIG. 7:
Vertical arrows indicate restriction sites.
x—scFv linker.
y—diabody linker junction (0–10 residues).
1—PCR.
2—Cloning after PCR assembly and restriction digestion.
3—Cloning entirely via restriction sites.
Route A—select binders as diabody fragments, the initial repertoires having one constant specificity (C).
Route B—construct bispecific diabody repertoire directly.
Route C—Select binders as scFv fragments.

FIG. 8:
1—Standard cloning.
2—Cre-mediated in vivo recombination via the LoxP recognition sites.
3—Self splicing of the RNA.
x—LoxP recognition sites.
y—Splice recognition sites (some part will form diabody linker sequence).
z—Self-splicing intron (Class I).
A—VH gene repertoire.
B—VL gene repertoire.
C—Large repertoire of VH and VL genes.
D—Diabody repertoire (RNA).

FIG. 9:
I and II—scFv fragments and bivalent fragments.
III, IV and V—Vectors for constructions.
VI—bispecific fragments.
VII—three chain fragments.

FIG. 10:
The graphs are of Relative response (RU) against Time (s).

FIG. 11:
The graph is of dR/dt (RU/s) against effluent time (s).

FIG. 15:
The graph is off ln(R1/Rt) vs time. Off-rate curves, beginning from 3000 ru on surface. Apparent koff (0–21s); s1: 0.0045, s2: 0.0047, s3: 0.0069, s4: 0.0071

| | pre incubation | elution buffer |
|---|---|---|
| 1 | PBS | PBS |
| 2 | NIP/PBS | PBS |
| 3 | PBS | NIP/PBS |
| 4 | NIP/PBS | NIP/PBS |

FIG. 16:
Biacore analysis of B1.8/NQ11 diabody to BSA-Ox surfaces in the presence and absence of 1 $\mu$M NIP. The graphs show Req against $\mu$M antibody.
x—control
y—+1 $\mu$M NIP FIG. 17:
Scatchard analysis of binding to surface 2. The graphs are Req against Req/$\mu$M.
A—control. y=−0.275x+510.444 $r^2$=0.977 Kd=275nM Rmax=510RU
B—+1 $\mu$M NIP. y=−0.425x+461.316 $r^2$=0.992 Kd=425nM Rmax=461RU FIG. 18:
Scatchard analysis of binding to surface 3. The graphs are Req against Req/$\mu$M
A—control. y=−0.275x+355.052 $r^2$=0.951 Kd=275nM Rmax=355RU
B—+1 $\mu$M NIP. y=−0.418x+348.166 $r^2$=0.968 Kd=418nM Rmax=348RU FIG. 31:
x—CBM-1 1 $\mu$M/ml
y—CBM-1 10 ng/ml
z—w/0 CBM-1

FIG. 33:
Cloning of a bispecific repertoire (Example 14)
1—PCR assembly with pUCreverse and LFRBS-2
2—Cut with KspI, ligate
3—PCR with pUCreverse and XhoTag
4—Cut with XhoI, ligate
5—PCR with BioGene3Lead and fd-tet-seq24
6—Clone as SfiI-NotI fragment into pCANTAB5myc phagemid vector to produce bispecific diabody repertoire FIG. 34:
Repertoires:
Plates 1, 4 and 7—phage from unselected clones.
Plates 2, 5 and 8—phage from clones selected on phOx-BSA
Plates 3, 6 and 9—soluble diabodies from clones selected on phOx-BSA.
ELISA:
Plates 1, 2 and 3—Dig-BSA.
Plates 4, 5 and 6—phOx-BSA.
Plates 7, 8 and 9—BSA.

What is claimed is:

1. A dimer of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker; and
(ii) a second polypeptide which has a first domain which comprises a binding region of an immunoglobulin heavy chain variable region, a second domain which comprises a binding region of an immunoglobulin light chain variable region, the first and second domains of the second polypeptide being linked by a polypeptide linker;

the first domain of the first polypeptide and the second domain of the second polypeptide associating to form a first antigen binding site; and the second domain of the first polypeptide and the first domain of the second polypeptide associating to form a second antigen binding site;

said first antigen binding site being different from said second antigen binding site;

the polypeptide linker of the first polypeptide being of a length such that said first and second domains of said first polypeptide are incapable of associating with each other to form an antigen binding site.

2. A dimer of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker having a length selected from the group consisting of 9, 8, 7 and 6 amino acids; and
(ii) a second polypeptide which has a first domain which comprises a binding region of an immunoglobulin heavy chain variable region, a second domain which comprises a binding region of an immunoglobulin light chain variable region, the first and second domains of the second polypeptide being linked by a polypeptide linker;

the first domain of the first polypeptide and the second domain of the second polypeptide associating to form a first antigen binding site; and the second domain of the first polypeptide and the first domain of the second polypeptide associating to form a second antigen binding site;

said first antigen binding site being different from said second antigen binding site.

3. A dimer according to claim 2 wherein said polypeptide linker of the second polypeptide is a length selected from the group consisting of 9, 8, 7, 6, 5, 4, 3, 2 and 1 amino acids.

4. A dimer of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker; and
(ii) a second polypeptide which has a first domain which comprises a binding region of an immunoglobulin heavy chain variable region, a second domain which comprises a binding region of an immunoglobulin light chain variable region, the first and second domains of the second polypeptide being linked by a polypeptide linker having a length selected from the group consisting of 9, 8, 7 and 6 amino acids;

the first domain of the first polypeptide and the second domain of the second polypeptide associating to form a first antigen binding site; and the second domain of the first polypeptide and the first domain of the second polypeptide associating to form a second antigen binding site;

said first antigen binding site being different from said second antigen binding site;

the polypeptide linker of the first polypeptide being of a length such that said first and second domains of said first polypeptide are incapable of associating with each other to form an antigen binding site.

5. A dimer of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker of 6 amino acids; and
(ii) a second polypeptide which has a first domain, which comprises a binding region of an immunoglobulin heavy chain variable region, a second domain, which comprises a binding region of an immunoglobulin light chain variable region, the first and second domains of the second polypeptide being linked by a polypeptide linker of 6 amino acids;

the first domain of the first polypeptide and the second domain of the second polypeptide associating to form a first antigen binding site; and the second domain of the first polypeptide and the first domain of the second polypeptide associating to form a second antigen binding site;

said first antigen binding site being different from said second antigen binding site.

6. A dimer of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker of 7 amino acids; and
(ii) a second polypeptide which has a first domain, which comprises a binding region of an immunoglobulin heavy chain variable region, a second domain, which comprises a binding region of an immunoglobulin light chain variable region, the first and second domains of the second polypeptide being linked by a polypeptide linker of 7 amino acids;

the first domain of the first polypeptide and the second domain of the second polypeptide associating to form a first antigen binding site; and the second domain of the first polypeptide and the first domain of the second polypeptide associating to form a second antigen binding site;

said first antigen binding site being different from said second antigen binding site.

7. A dimer according to claim 1 wherein the first polypeptide is fused to additional amino acid residues at its N- or C-terminus.

8. A dimer according to claim 1 having an antigen binding site which binds to an antigen selected from the group consisting of:

a virus, human immunodeficiency virus 1 (HIV 1), a hormone, a cytokine, tumour necrosis factor alpha (TNFα), an antibody, the idiotope of an antibody, a cell surface protein, a Fc receptor, a tumour specific marker, and carcinoembryonic antigen (CEA).

9. A dimer according to claim 1, wherein the first domains of the first and second polypeptides are located N-terminal to the second domains of said first and second polypeptides.

10. A dimer according to claim 1, wherein the first domains of the first and second polypeptides are located C-terminal to the second domains of said first and second polypeptides.

11. A dimer according to claim 1 which binds to antigens on two different cell surfaces.

12. A population of dimers wherein each dimer is of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker; and
(ii) a second polypeptide which has a first domain which comprises a binding region of an immunoglobulin heavy chain variable region, a second domain which comprises a binding region of an immunoglobulin light chain variable region, the first and second domains of the second polypeptide being linked by a polypeptide linker;
the first domain of the first polypeptide and the second domain of the second polypeptide associating to form a first antigen binding site; and
the second domain of the first polypeptide and the first domain of the second polypeptide associating to form a second antigen binding site;
said first antigen binding site being different from said second antigen binding site;
the polypeptide linker of the first polypeptide being of a length such that said first and second domains of said first polypeptide are incapable of associating with each other to form an antigen binding site, wherein said population has a diverse repertoire of antigen binding activities.

13. An assay for an antigen using a dimer according to claim 1 comprising the steps:
(a) incubating the dimer and an antigen, wherein said antigen binds to either or both the first and second antigen binding site of the dimer, under conditions which permit binding of the dimer to the antigen, and
(b) detecting the antigen-dimer binding.

14. An assay according to claim 12 which is a diagnostic assay.

15. An assay according to claim 12 comprising the crosslinking of two antigens.

16. An assay according to claim 12 comprising agglutination of two cells.

17. An assay according to claim 12 wherein one antigen is on a surface and the other antigen is in solution.

18. An assay for an antigen using a dimer comprising the steps:
(a) incubating the dimer and an antigen, wherein said antigen binds to either or both of the first and second antigen binding sites of the dimer, under conditions which permit binding of the dimer to the antigen, and
(b) detecting the antigen-dimer binding using surface plasmon resonance;
said dimer being of
(i) a first polypeptide comprising a first domain which comprises a binding region of an immunoglobulin heavy chain variable region, and a second domain which comprises a binding region of an immunoglobulin light chain variable region, the first and second domains of the first polypeptide being linked by a polypeptide linker; and
(ii) a second polypeptide which has a first domain which comprises a binding region of an immunoglobulin heavy chain variable region, a second domain which comprises a binding region of an immunoglobulin light chain variable region, the first and second domains of the second polypeptide being linked by a polypeptide linker;
the first domain of the first polypeptide and the second domain of the second polypeptide associating to form a first antigen binding site; and
the second domain of the first polypeptide and the first domain of the second polypeptide associating to form a second antigen binding site;
said first antigen binding site being different from said second antigen binding site;
the polypeptide linker of the first polypeptide being of a length such that said first and second domains of said first polypeptide are incapable of associating with each other to form an antigen binding site.

19. A pharmaceutical preparation comprising, as its active ingredient, a dimer according to claim 1.

20. A dimer according to claim 2 wherein the first polypeptide is fused to additional amino acid residues at its N- or C-terminus.

21. A dimer according to claim 3 wherein the first polypeptide is fused to additional amino acid residues at its N- or C-terminus.

22. A dimer according to claim 2 having an antigen binding site which binds to an antigen selected from the group consisting of:
a virus, human immunodeficiency virus 1 (HIV 1), a hormone, a cytokine,
tumour necrosis factor alpha (TNFα), an antibody, the idiotope of an antibody, a cell surface protein, a Fc receptor, a tumour specific marker, and carcinoembryonic antigen (CEA).

23. A dimer according to claim 3 having an antigen binding site which binds to an antigen selected from the group consisting of:
a virus, human immunodeficiency virus 1 (HIV 1), a hormone, a cytokine,
tumour necrosis factor alpha (TNFα), an antibody, the idiotope of an antibody, a cell surface protein, a Fc receptor, a tumour specific marker, and carcinoembryonic antigen (CEA).

24. A dimer according to claim 2, wherein the first domains of the first and second polypeptides are located N-terminal to the second domains of said first and second polypeptides.

25. A dimer according to claim 3, wherein the first domains of the first and second polypeptides are located N-terminal to the second domains of said first and second polypeptides.

26. A dimer according to claim 2, wherein the first domains of the first and second polypeptides are located C-terminal to the second domains of said first and second polypeptides.

27. A dimer according to claim 3, wherein the first domains of the first and second polypeptides are located C-terminal to the second domains of said first and second polypeptides.

28. A dimer according to claim 2 which binds to antigens on two different cell surfaces.

29. A dimer according to claim 3 which binds to antigens on two different cell surfaces.

30. An assay for an antigen using a dimer according to claim 2 comprising the steps:
(a) incubating the dimer and an antigen, wherein said antigen binds to either or both the first and second antigen binding site of the dimer, under conditions which permit binding of the dimer to the antigen, and (b) detecting the antigen-dimer binding.

31. An assay for an antigen using a dimer according to claim 3 comprising the steps:
   (a) incubating the dimer and an antigen, wherein said antigen binds to either or both the first and second antigen binding site of the dimer, under conditions which permit binding of the dimer to the antigen, and
   (b) detecting the antigen-dimer binding.

32. A pharmaceutical preparation comprising, as its active ingredient, a dimer according to claim 2.

33. A pharmaceutical preparation comprising, as its active ingredient, a dimer according to claim 3.

* * * * *

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:1:

GACTCATTCT CGACTGAGCT CACTTGGCGC GCCTTATTAC CGTTTGATCT CGAGCTTGGT      60

CCC                                                                   63

(2) INFORMATION FOR SEQ ID NO:2:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:2:

GTCCTCGCAA CTGGCGCGCC ACAATTTCAC AGTAAGGAGG TTTAACTTGT GAAAAAATTA      60

TTATTCGCAA TT                                                         72

(2) INFORMATION FOR SEQ ID NO:3:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:3:

GAGCCATCAA TCGATCTGGT CACCGTCTCC TCAGACATTG AGCTCACCCA GTCTCCA        57

(2) INFORMATION FOR SEQ ID NO:4:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:4:

GAGCCATCAA TCGATCTGGT CACCGTCTCC TCAGGCGGTG GCGGATCGGA CATTGAGCTC      60

ACCCAGTCTC CA                                                         72

(2) INFORMATION FOR SEQ ID NO:5:

(i) SEQUENCE CHARACTERISTICS:
        (A) LENGTH: 87 base pairs
        (B) TYPE: nucleic acid (C) STRANDEDNESS: single
        (D) TOPOLOGY: linear (ii) MOLECULE TYPE: DNA primer (xi) SEQUENCE DESCRIPTION: SEQ ID NO:5:

GAGCCATCAA TCGATCTGGT CACCGTCTCC TCAGGCGGTG GCGGATCGGG CGGTGGCGGA        60

TCGGACATTG AGCTCACCCA GTCTCCA        87

(2) INFORMATION FOR SEQ ID NO:6:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:6:

GAGCCATCAA TCTCGGAGCT CGATGTCTGA GGAGACGGTG ACCGTGGTCC CTTGGCCCC        59

(2) INFORMATION FOR SEQ ID NO:7:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:7:

GAGCCATCAA TCTCGGAGCT CGATGTCCGA TCCGCCACCG CCTGAGGAGA CGGTGACCGT        60

GGTCCCTTGG CCCC        74

(2) INFORMATION FOR SEQ ID NO:8:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:8:

GAGCCATCAA TCTCGGAGCT CGATGTCCGA TCCGCCACCG CCCGATCCGC CACCGCCTGA        60

GGAGACGGTG ACCGTGGTCC CTTGGCCCC        89

(2) INFORMATION FOR SEQ ID NO:9:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:9:

GCACCCTGGT CACCGTCTCG AGCGGCGGTG GCGGATCGGA CATTGTGATG ACCCAGTCTC        60

AC        62

(2) INFORMATION FOR SEQ ID NO:10:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA primer (xi) SEQUENCE DESCRIPTION: SEQ ID NO:10:

ACTGCGGCCA GCCGGCCATG GCCCAGGTGC AGCTGAAGGA GTCAGG     46

(2) INFORMATION FOR SEQ ID NO:11:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:11:

CAAGGGACCA CGGTCACCGT CTCGAGCGGG GGTGGCGGAT CCGACATTGA GCTCACCCAG     60
TCT                                                                  63

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:12:

CAAGGGACCA CGGTCACCGT CTCGAGCGAC ATTGAGCTCA CCCAGTCT     48

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:13:

TTTGTCGTCT TTCCAGACGT TAGT     24

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:14:

ACACTTGAGC TGGCCCT     17

(2) INFORMATION FOR SEQ ID NO:15:

(i) SEQUENCE CHARACTERISTICS:

(A) LENGTH: 63 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:15:

CAAGGGACCA CGGTCACCGT CTCGAGCGGG GGTGGCGGAT CCCAGTCTGT GCTGACGCAG      60

CCG      63

(2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:16:

CAAGGGACCA CGGTCACCGT CTCGAGCCAG TCTGTGCTGA CGCAGCCG      48

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:17:

GCTGCTTCCA GAGCAGG      17

(2) INFORMATION FOR SEQ ID NO:18:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:18:

CCATCAATCG ATCTGGTCAC CGTCTCCGAC ATTGAGCTCA CCCAGTCTCC A      51

(2) INFORMATION FOR SEQ ID NO:19:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:19:

CCATCAATCG ATCTGGTCAC CGTCTCCTCA ATTGAGCTCA CCCAGTCTCC A      51

(2) INFORMATION FOR SEQ ID NO:20:

(i) SEQUENCE CHARACTERISTICS:
        (A) LENGTH: 54 base pairs
        (B) TYPE: nucleic acid (C) STRANDEDNESS: single
        (D) TOPOLOGY: linear (ii) MOLECULE TYPE: DNA primer (xi) SEQUENCE DESCRIPTION: SEQ ID NO:20:

CCATCAATCG ATCTGGTCAC CGTCTCCTCA GAGCTCACCC AGTCTCCAGC CTCC        54

(2) INFORMATION FOR SEQ ID NO:21:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:21:

CCATCAATCG ATCTGGTCAC CGTCTCCGAG CTCACCCAGT CTCCAGCCTC CCTT        54

(2) INFORMATION FOR SEQ ID NO:22:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:22:

GAGCCATCAA TCTCGGAGCT CGATGTCGGA GACGGTGACC GTGGTCCCTT GGCC        54

(2) INFORMATION FOR SEQ ID NO:23:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:23:

GAGCCATCAA TCTCGGAGCT CGATTGAGGA GACGGTGACC GTGGTCCCTT GGCC        54

(2) INFORMATION FOR SEQ ID NO:24:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:24:

GAGCCATCAA TCTCGGAGCT CGATGTCGAC GGTGACCGTG GTCCCTTGGC CCCAGTAGTC        60

(2) INFORMATION FOR SEQ ID NO:25:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:25:

GAGCCATCAA TCTCGGAGCT CGATGACGGT GACCGTGGTC CCTTGGCCCC AGTAGTC        57

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:26:

AACAGCTATG ACCATG        16

(2) INFORMATION FOR SEQ ID NO:27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:27:

CGATCCGCCA CCGCCTGAGG AGACGGTGAC CGTGGTCCC        39

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:28:

GTCGTCTTTC CAGACGTTAG T        21

(2) INFORMATION FOR SEQ ID NO:29:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:29:

GGCGGTGGCG GATCGCAGTC TGTGTTGACG ACGCAGCCGC C        41

(2) INFORMATION FOR SEQ ID NO:30:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:30:

AACAGCTATG ACCATG        16

(2) INFORMATION FOR SEQ ID NO:31:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:31:

```
GAGTCATTCT CGACTTGCGG CCGCACACCG TTTGATCTCG AGCTTGGTCC            50
```

(2) INFORMATION FOR SEQ ID NO:32:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:32:

```
CATGCCATGA CTCGCGGCCC AGCCGGCCAT GGCCGAGGTC CAACTGGTGG AGAGCGGT   58
```

(2) INFORMATION FOR SEQ ID NO:33:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:33:

```
CCATCAATCG ATCTGGTCAC CGTCTCCTCA CAGGCTGTTG GGACACAGGA ATCTGCA    57
```

(2) INFORMATION FOR SEQ ID NO:34:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:34:

```
GAGTCATTCT CGACTTGGCG CGCCTTATTA CCGTTTGATC TCGAGGACAG TCAG       54
```

(2) INFORMATION FOR SEQ ID NO:35:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:35:

```
GAGCCATCAA TCGATCTGGT CACCGTCTCC TCAGGCGGTG GCGGATCGGA CATCGAGCTC   60
ACCCAGAGCC CA                                                       72
```

(2) INFORMATION FOR SEQ ID NO:36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:36:

GAGTCATTCT CGACTTGCGG CCGCACGTTT GATTTCCACC TTGGTCCC         48

(2) INFORMATION FOR SEQ ID NO:37:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:37:

CATGCCATGA CTCGCGGCCC AGCCGGCCAT GGCCGAGGTG CAGCTGGTGG AGTCTGG     57

(2) INFORMATION FOR SEQ ID NO:38:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:38:

GAGCCATCAA TCGATCTGGT CACCGTCTCC TCAGGCGGTG GCGGATCTGA CATCCAGATG    60

ACCCAGTCTC CA                                                       72

(2) INFORMATION FOR SEQ ID NO:39:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:39:

GAGTCATTCT CGACTCTGTC GGGCGCGCCT CATGATTACG CCCAGCTTGC ATGC       54

(2) INFORMATION FOR SEQ ID NO:40:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:40:

CAGATCTGAG GAGACGGTGA CCGTGGTCCC TGCGCCCC                         38

(2) INFORMATION FOR SEQ ID NO:41:

(i) SEQUENCE CHARACTERISTICS:
    (A) LENGTH: 57 base pairs
    (B) TYPE: nucleic acid
    (C) STRANDEDNESS: single
    (D) TOPOLOGY: linear (ii) MOLECULE TYPE: DNA primer (xi) SEQUENCE DESCRIPTION: SEQ ID NO:41:

CATGCCATGA CTCGCGGCCC AGCCGGCCAT GGCCGAAGTG AAGCTGGTGG AGTCTGG       57

(2) INFORMATION FOR SEQ ID NO:42:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:42:

GAGCCATCAA TCGATCTGGT CACCGTCTCC TCAGGCGGTG GCGGATCGGA CATTGAGCTC       60

ACCCAGTCTC AA       72

(2) INFORMATION FOR SEQ ID NO:43:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:43:

CATGCCATGA CTCGCGGCCC AGCCGGCCAT GGCCSAGGTG AAGCTGGTGG ARTCTGG       57

(2) INFORMATION FOR SEQ ID NO:44:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:44:

GAGCCATCAA TCGATCTGGT CACCGTCTCC TCAGGCGGTG GCGGATCGGA CATTGTGCTR       60

ACCCAGTCTC CA       72

(2) INFORMATION FOR SEQ ID NO:45:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:45:

GAGCCATCAA TCTCGGAGCT CGATGTCCGA TCCGCCACCG CCCTTGCAGG AGGTGCATTT       60

GCACTCTTTG CACTTGCAGG AGCCACCGCC TGAGGAGACG GTGACCGTGG TCCCTTGGCC       120

CC       122

(2) INFORMATION FOR SEQ ID NO:46:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:46:

```
GACTCATTCT CGACTTGGCG CGCCTTATTA GGCGCAGGTG CAGGAGTCAC CGGCGGCACA      60
GGAGCAGTTG GGATCGCCAC CGCCGATCTC GAGCTTGGTC CCTCCACC                 108
```

(2) INFORMATION FOR SEQ ID NO:47:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:47:

```
GAGCCATCAA TCGATCTGGT CACCGTCTCC TCAGGCGATC CCAACTGCTC CTGTGCCGCC      60
GGTGACTCCT GCACCTGCGC CGGCGGTTCG GACATTGAGC TCACCCAGTC TCCA           114
```

(2) INFORMATION FOR SEQ ID NO:48:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:48:

```
GAGTCATTCT CGACTTGCGG CCGCCTTGCA GGAGGTGCAT TTGCACTCTT TGCACTTGCA      60
GGAGCCTCCA CCGCCGATCT CGAGCTTGGT CCCTCCACC                            99
```

(2) INFORMATION FOR SEQ ID NO:49:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:49:

```
GAGTCATTCT CGACTTGCGG CCGCACACCG TTTGATCTCG AGCTTGGTCC C               51
```

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:50:

GCCAGGTCCT GACTCCTGCA GCTGCACCTG                                                30

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:51:

GGTGGAGGCA CCAAGCTGGA GATCAAACGG                                                30

(2) INFORMATION FOR SEQ ID NO:52:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:52:

GAGCCATCAA TCGATCTGGT CACCGTCTCC TCAGGCGGTG GCGGATCGGA CATTGAACTC               60

ACCCAGTCTC CA                                                                   72

(2) INFORMATION FOR SEQ ID NO:53:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:53:

GAGCCATCAA TCTCGGAGCT CGATGTCCGA TCCGCCACCG CCTGAGGAGA CAGTGACCGT               60

GGTCCCTTGG CCCC                                                                 74

(2) INFORMATION FOR SEQ ID NO:54:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:54:

CTCAGCAGCC TGAAATCTGA GGACTCTGCG GTC                                            33

(2) INFORMATION FOR SEQ ID NO:55:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:55:

```
GTCCGCCAGC CTCCAGGAGA GGCACTTGAG TGG                              33

(2) INFORMATION FOR SEQ ID NO:56:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:56:

CGCCAGCCTC CAGGATGCGC ACTTGAGTGG TTGGGTTCTG TTAGAAAC              48

(2) INFORMATION FOR SEQ ID NO:57:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:57:

AAGCAGAGGC CTGGATGCGG CCTTGAGTGG ATTGGAAGGA TTGATCC               47

(2) INFORMATION FOR SEQ ID NO:58:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:58:

ATAAACACCC TGCAAACTGA GGACAGTGCC ACT                              33

(2) INFORMATION FOR SEQ ID NO:59:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:59:

GTCCGCCAGC CTCCAGGATT GGCACTTGAG TGG                              33

(2) INFORMATION FOR SEQ ID NO:60:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:60:

GTGAAGCAGA GGCCTGGAAT CGGCCTTGAG TGG                              33
```

```
(2) INFORMATION FOR SEQ ID NO:61:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:61:

CTCAGCAGCC TGGAATCTGA GGACTCTGCG GTC                                33

(2) INFORMATION FOR SEQ ID NO:62:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:62:

GTCCTCGCAA CTGCGGCCCA GCCGGCCATG GCCGACATCG ACCTCACCCA AACTCCA      57

(2) INFORMATION FOR SEQ ID NO:63:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:63:

GAGTCATTCT CGACTTGCGG CCGCTGAGGA GACGGTGACC GTGGTCCCTT GGCCCC        56

(2) INFORMATION FOR SEQ ID NO:64:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:64:

CGTTCGGAGG GGGGACCAAG CTCGAGATCA AACGGCAGGT GCAGCTGCAG GAGTCAGG     58

(2) INFORMATION FOR SEQ ID NO:65:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:65:

CGTTCGGAGG GGGGACCAAG CTCGAGATCA AACGGGGAGG CCAGGTGCAG CTGCAGGAGT   60
CAGG                                                                64

(2) INFORMATION FOR SEQ ID NO:66:
```

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA primer (xi) SEQUENCE DESCRIPTION: SEQ ID NO:66:

CCAGATCATT TACCCACTGG TC                                          22

(2) INFORMATION FOR SEQ ID NO:67:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:67:

TGGAGACTGG GTGAGCTCAA TGTCGCTCGA GCCACCGCCA GAGCC                 45

(2) INFORMATION FOR SEQ ID NO:68:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:68:

AGCGGATAAC AATTTCACAC AGG                                         23

(2) INFORMATION FOR SEQ ID NO:69:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:69:

GGCCAAGGGA CCACGGTCAC CGTCTCCTCA GACATTGAGC TCACCCAGTC TCCA       54

(2) INFORMATION FOR SEQ ID NO:70:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:70:

GGCACCAAGC TGGAAATCAA ACGGTAATAA CCCTGCAGGT CGACAAGGAG ACAG       54

(2) INFORMATION FOR SEQ ID NO:71:

(i) SEQUENCE CHARACTERISTICS:
        (A) LENGTH: 54 base pairs
        (B) TYPE: nucleic acid
        (C) STRANDEDNESS: single (D) TOPOLOGY: linear (ii) MOLECULE TYPE: DNA primer (xi) SEQUENCE DESCRIPTION: SEQ ID NO:71:

GGGACCAAGC TGGAAATAAA ACGGTAATAA CCCTGCAGGT CGACAAGGAG ACAG          54

(2) INFORMATION FOR SEQ ID NO:72:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA primer (xi) SEQUENCE DESCRIPTION: SEQ ID NO:72:

GGGACAAAGT TGGAAATAAA ACGGTAATAA CCCTGCAGGT CGACAAGGAG ACAG          54

(2) INFORMATION FOR SEQ ID NO:73:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA primer (xi) SEQUENCE DESCRIPTION: SEQ ID NO:73:

GGGACCAAGC TGGAGCTGAA ACGGTAATAA CCCTGCAGGT CGACAAGGAG ACAG          54

(2) INFORMATION FOR SEQ ID NO:74:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA primer (xi) SEQUENCE DESCRIPTION: SEQ ID NO:74:

GGCCATCGCT GGTTGGGCAG CCGCGG                                         26

(2) INFORMATION FOR SEQ ID NO:75:

(i) SEQUENCE CHARACTERISTICS:
         (A) LENGTH: 75 base pairs
         (B) TYPE: nucleic acid
         (C) STRANDEDNESS: single
         (D) TOPOLOGY: linear (ii) MOLECULE TYPE: DNA primer (xi) SEQUENCE DESCRIPTION: SEQ ID NO:75:

CATGCCATGA CTCAGGCCCA GCCGGCCATG GCCTCCGCGG CTGCCCAACC AGCGATGGCC    60

SAGGTSMARC TGCAG                                                    75

(2) INFORMATION FOR SEQ ID NO:76:

(i) SEQUENCE CHARACTERISTICS:
         (A) LENGTH: 51 base pairs
         (B) TYPE: nucleic acid
         (C) STRANDEDNESS: single
         (D) TOPOLOGY: linear (ii) MOLECULE TYPE: DNA primer (xi) SEQUENCE DESCRIPTION: SEQ ID NO:76:

GCCTGAACCG CCTCCACCAC TCGAGACGGT GACCGTGGTC CCTTGGCCCC A           51

(2) INFORMATION FOR SEQ ID NO:77:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA primer (xi) SEQUENCE DESCRIPTION: SEQ ID NO:77:

CATGCCATGA CTCAGGCC                                                18

(2) INFORMATION FOR SEQ ID NO:78:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: DNA primer (xi) SEQUENCE DESCRIPTION: SEQ ID NO:78:

AGCTGAACCG CCTCCACCGC TC                                           22

(2) INFORMATION FOR SEQ ID NO:79:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA primer (xi) SEQUENCE DESCRIPTION: SEQ ID NO:79:

TTATTATTCG CAATTCCTTT AGTTGTTCCT                                   30

(2) INFORMATION FOR SEQ ID NO:80:

(i) SEQUENCE CHARACTERISTICS:
           (A) LENGTH: 58 base pairs
           (B) TYPE: nucleic acid
           (C) STRANDEDNESS: single
           (D) TOPOLOGY: linear (ii) MOLECULE TYPE: DNA primer (xi) SEQUENCE DESCRIPTION: SEQ ID NO:80:

GAGCCATCAA TCTCGGAGCT CGATGTCACC TACCTTACGA GTACTCCAAA ACTAATCA    58

(2) INFORMATION FOR SEQ ID NO:81:

(i) SEQUENCE CHARACTERISTICS:
           (A) LENGTH: 56 base pairs
           (B) TYPE: nucleic acid
           (C) STRANDEDNESS: single
           (D) TOPOLOGY: linear (ii) MOLECULE TYPE: DNA primer (xi) SEQUENCE DESCRIPTION: SEQ ID NO:81:

```
CCATCAATCG ATCTGGTCAC CGTCTCCTCA GGCTCTCTAA ATAGCAATAT TTACCT            56
```

(2) INFORMATION FOR SEQ ID NO:82:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:82:

```
GAGCCATCAA TCTCGGAGCT CGATGTCACC AGACGAGTAC TCCAAAACTA ATCG              54
```

(2) INFORMATION FOR SEQ ID NO:83:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:83:

```
CCATCAATCG ATCTGGTCAC CGTCTCCTCA GGTCTCTCTA AATAGCAATA TTTACCT           57
```

(2) INFORMATION FOR SEQ ID NO:84:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:84:

```
GTAAAACGAC GGCCAGT                                                       17
```

(2) INFORMATION FOR SEQ ID NO:85:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:85:

```
CAGGAAACAG CTATGAC                                                       17
```

(2) INFORMATION FOR SEQ ID NO:86:

(i) SEQUENCE CHARACTERISTICS:
        (A) LENGTH: 5 amino acids
        (B) TYPE: amino acid
        (D) TOPOLOGY: linear (ii) MOLECULE TYPE: peptide linker (xi) SEQUENCE DESCRIPTION: SEQ ID NO:86:

```
Gly Gly Gly Gly Ser
1               5
```

(2) INFORMATION FOR SEQ ID NO:87:

(i) SEQUENCE CHARACTERISTICS:
           (A) LENGTH: 4 amino acids
           (B) TYPE: amino acid
           (D) TOPOLOGY: linear (ii) MOLECULE TYPE: peptide linker (xi) SEQUENCE DESCRIPTION: SEQ ID NO:87:

Ser Ser Asp Ile
1

(2) INFORMATION FOR SEQ ID NO:88:

(i) SEQUENCE CHARACTERISTICS:
           (A) LENGTH: 9 amino acids
           (B) TYPE: amino acid
           (D) TOPOLOGY: linear (ii) MOLECULE TYPE: peptide linker (xi) SEQUENCE DESCRIPTION: SEQ ID NO:88:

Ser Ser Gly Gly Gly Gly Ser Asp Ile
1               5

(2) INFORMATION FOR SEQ ID NO:89:

(i) SEQUENCE CHARACTERISTICS:
           (A) LENGTH: 14 amino acids
           (B) TYPE: amino acid
           (D) TOPOLOGY: linear (ii) MOLECULE TYPE: peptide linker (xi) SEQUENCE DESCRIPTION: SEQ ID NO:89:

Ser Ser Gly Gly Gly Gly Ser Gly Gly Gly Gly Ser Asp Ile
1               5                   10

(2) INFORMATION FOR SEQ ID NO:90:

(i) SEQUENCE CHARACTERISTICS:
           (A) LENGTH: 19 amino acids
           (B) TYPE: amino acid
           (D) TOPOLOGY: linear (ii) MOLECULE TYPE: peptide linker (xi) SEQUENCE DESCRIPTION: SEQ ID NO:90:

Ser Ser Gly Gly Gly Gly Ser Gly Gly Gly Gly Ser Gly Gly Gly Gly
1               5                   10                  15

Ser Asp Ile (2) INFORMATION FOR SEQ ID NO:91:

(i) SEQUENCE CHARACTERISTICS:
           (A) LENGTH: 48 base pairs
           (B) TYPE: nucleic acid
           (C) STRANDEDNESS: double
           (D) TOPOLOGY: circular (ii) MOLECULE TYPE: DNA (xi) SEQUENCE DESCRIPTION: SEQ ID NO:91:

CGGTAATAAG GCGCGCCACA ATTTCACACT AAGGAGGTTT AACTTGTG                    48

(2) INFORMATION FOR SEQ ID NO:92:

(i) SEQUENCE CHARACTERISTICS:

(A) LENGTH: 16 base pairs
            (B) TYPE: nucleic acid
            (C) STRANDEDNESS: double
            (D) TOPOLOGY: circular (ii) MOLECULE TYPE: DNA (xi) SEQUENCE DESCRIPTION: SEQ ID NO:92:

TTCTATGCGG CCCAGC                                                16

(2) INFORMATION FOR SEQ ID NO:93:

(i) SEQUENCE CHARACTERISTICS:
            (A) LENGTH: 16 base pairs
            (B) TYPE: nucleic acid
            (C) STRANDEDNESS: double
            (D) TOPOLOGY: circular (ii) MOLECULE TYPE: DNA (xi) SEQUENCE DESCRIPTION: SEQ ID NO:93:

GGCCGCAGAA ACTGTT                                                16

(2) INFORMATION FOR SEQ ID NO:94:

(i) SEQUENCE CHARACTERISTICS:
            (A) LENGTH: 162 base pairs
            (B) TYPE: nucleic acid
            (C) STRANDEDNESS: double
            (D) TOPOLOGY: circular (ii) MOLECULE TYPE: DNA (ix) FEATURE:
            (A) NAME/KEY: CDS
            (B) LOCATION: 1..162
            (D) OTHER INFORMATION: /transl_except= (pos: 151 .. 153, aa:
                Glu)

(ix) FEATURE:
            (A) NAME/KEY: misc_difference
            (B) LOCATION: replace(151..153, "")
            (D) OTHER INFORMATION: /standard_name= "Suppresible stop"

(xi) SEQUENCE DESCRIPTION: SEQ ID NO:94:

GTG AAA AAA TTA TTA TTC GCA ATT CCT TTA GTT GTT TTC TAT GCG GCC        48
Val Lys Lys Leu Leu Phe Ala Ile Pro Leu Val Val Phe Tyr Ala Ala
 1               5                  10                  15

CAG CCG GCC ATG GCC CAG GTC CAA CTG CAG GTC GAC CTC GAG ATC AAA        96
Gln Pro Ala Met Ala Gln Val Gln Leu Gln Val Asp Leu Glu Ile Lys
                20                  25                  30

CGG GCG GCC GCA GAA CAA AAA CTC ATC TCA GAA GAG GAT CTG AAT GGG       144
Arg Ala Ala Ala Glu Gln Lys Leu Ile Ser Glu Glu Asp Leu Asn Gly
         35                  40                  45

GCC GCA TAG ACT GTT GAA                                              162
Ala Ala Glu Thr Val Glu
         50

(2) INFORMATION FOR SEQ ID NO:95:

(i) SEQUENCE CHARACTERISTICS:
            (A) LENGTH: 54 amino acids
            (B) TYPE: amino acid
            (D) TOPOLOGY: linear (ii) MOLECULE TYPE: protein (xi) SEQUENCE DESCRIPTION: SEQ ID NO:95:

Val Lys Lys Leu Leu Phe Ala Ile Pro Leu Val Val Phe Tyr Ala Ala

```
                1               5                      10                        15
Gln Pro Ala Met Ala Gln Val Gln Leu Gln Val Asp Leu Glu Ile Lys
                        20                    25                30

Arg Ala Ala Glu Gln Lys Leu Ile Ser Glu Glu Asp Leu Asn Gly
        35                        40                    45

Ala Ala Glu Thr Val Glu
    50
```

(2) INFORMATION FOR SEQ ID NO:96:

(i) SEQUENCE CHARACTERISTICS:
        (A) LENGTH: 274 base pairs
        (B) TYPE: nucleic acid
        (C) STRANDEDNESS: double
        (D) TOPOLOGY: circular (ii) MOLECULE TYPE: DNA (ix) FEATURE:
        (A) NAME/KEY: CDS
        (B) LOCATION: 35..271
        (D) OTHER INFORMATION: /transl_except= (pos: 215 .. 217, aa: Glu)

(ix) FEATURE:
        (A) NAME/KEY: misc_difference
        (B) LOCATION: replace(215..217, "")
        (D) OTHER INFORMATION: /standard_name= "Amber"

(xi) SEQUENCE DESCRIPTION: SEQ ID NO:96:

```
AAGCTTTGGA GCCTTTTTTT TGGAGATTTT CAAC GTG AAA AAA TTA TTA TTC          52
                                     Val Lys Lys Leu Leu Phe
                                      1               5

GCA ATT CCT TTA GTT GTT CCT TTC TAT GCG GCC CAG CCG GCC ATG GCC       100
Ala Ile Pro Leu Val Val Pro Phe Tyr Ala Ala Gln Pro Ala Met Ala
             10                  15                  20

CAG GTC CAA CTG CAG GTC GAC CTC GAG ATC AAA CGG GCG GCC GCA CAT       148
Gln Val Gln Leu Gln Val Asp Leu Glu Ile Lys Arg Ala Ala Ala His
         25                  30                  35

CAT CAT CAC CAT CAC GGG GCC GCA GAA CAA AAA CTC ATC TCA GAA GAG       196
His His His His His Gly Ala Ala Glu Gln Lys Leu Ile Ser Glu Glu
     40                      45                  50

GAT CTG AAT GGG GCC GCA TAG ACT GTT GAA AGT TGT TTA GCA AAA CCT       244
Asp Leu Asn Gly Ala Ala Glu Thr Val Glu Ser Cys Leu Ala Lys Pro
 55              60                  65                      70

CAT ACA GAA AAT TCA TTT ACT AAC GTC TGG                               274
His Thr Glu Asn Ser Phe Thr Asn Val
                 75
```

(2) INFORMATION FOR SEQ ID NO:97:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO:97:

```
Val Lys Lys Leu Leu Phe Ala Ile Pro Leu Val Val Pro Phe Tyr Ala
 1               5                  10                  15

Ala Gln Pro Ala Met Ala Gln Val Gln Leu Gln Val Asp Leu Glu Ile
                 20                  25                  30

Lys Arg Ala Ala Ala His His His His His Gly Ala Ala Glu Gln
         35                  40                      45
```

Lys Leu Ile Ser Glu Glu Asp Leu Asn Gly Ala Ala Glu Thr Val Glu
    50                  55                  60

Ser Cys Leu Ala Lys Pro His Thr Glu Asn Ser Phe Thr Asn Val
65                  70                  75

(2) INFORMATION FOR SEQ ID NO:98:

(i) SEQUENCE CHARACTERISTICS:
        (A) LENGTH: 15 amino acids
        (B) TYPE: amino acid
        (D) TOPOLOGY: linear (ii) MOLECULE TYPE: peptide linker (xi) SEQUENCE DESCRIPTION: SEQ ID NO:98:

Gly Gly Gly Gly Ser Gly Gly Gly Ser Gly Gly Gly Ser
1               5                  10                  15

(2) INFORMATION FOR SEQ ID NO:99:

(i) SEQUENCE CHARACTERISTICS:
        (A) LENGTH: 6 amino acids
        (B) TYPE: amino acid
        (D) TOPOLOGY: linear (ii) MOLECULE TYPE: peptide linker (xi) SEQUENCE DESCRIPTION: SEQ ID NO:99:

Gly Ser Ile Glu Gly Arg
  1               5

(2) INFORMATION FOR SEQ ID NO:100:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:100:

Met Gly Ser His His His His His His Ser Ile Glu Gly Arg
1               5                  10

(2) INFORMATION FOR SEQ ID NO:101:

(i) SEQUENCE CHARACTERISTICS:
        (A) LENGTH: 14 amino acids
        (B) TYPE: amino acid
        (D) TOPOLOGY: linear (ii) MOLECULE TYPE: peptide linker (xi) SEQUENCE DESCRIPTION: SEQ ID NO:101:

Gly Gly Gly Gly Ser Gly Gly Gly Ser Gly Gly Ser Ser
1               5                  10

(2) INFORMATION FOR SEQ ID NO:102:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:102:

```
TAATAACCCT GCAGGTCGAC AAGGAGACAG TCAGTGAAAA AACTCCTCTT TGCCATACCA        60
CTCGTGGTGC CATTTTACTC CGCGGCTGCC CAACCAGCGA TGGCC                       105
```

(2) INFORMATION FOR SEQ ID NO:103:

(i) SEQUENCE CHARACTERISTICS:
        (A) LENGTH: 5 amino acids
        (B) TYPE: amino acid
        (D) TOPOLOGY: linear (ii) MOLECULE TYPE: peptide linker (xi) SEQUENCE DESCRIPTION: SEQ ID NO:103:

```
Gly Leu Ser Ser Gly
1               5
```

(2) INFORMATION FOR SEQ ID NO:104:

(i) SEQUENCE CHARACTERISTICS:
        (A) LENGTH: 6 amino acids
        (B) TYPE: amino acid
        (D) TOPOLOGY: linear (ii) MOLECULE TYPE: peptide linker (xi) SEQUENCE DESCRIPTION: SEQ ID NO:104:

```
Gly Ser Leu Lys Val Gly
1               5
```

(2) INFORMATION FOR SEQ ID NO:105:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:105:

```
Gly Gly Gly Asp Pro Asn Cys Ser Cys Ala Ala Gly Asp Ser Cys Thr
1               5                   10                  15
Cys Ala Gly Gly Ser
                20
```

(2) INFORMATION FOR SEQ ID NO:106:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:106:

```
Gly Gly Gly Gly Ser Cys Lys Cys Lys Glu Cys Lys Cys Thr Ser Cys
1               5                   10                  15
Lys Gly Gly Ser Gly
                20
```